US011332521B2

(12) United States Patent
Kim et al.

(10) Patent No.: US 11,332,521 B2
(45) Date of Patent: May 17, 2022

(54) ANTI-FAMILY WITH SEQUENCE SIMILARITY 19, MEMBER A5 ANTIBODIES AND METHOD OF USE THEREOF

(71) Applicant: NEURACLE SCIENCE CO., LTD., Seoul (KR)

(72) Inventors: Bongcheol Kim, Seongnam-si (KR); Jae Young Seong, Seoul (KR); Jong Ik Hwang, Seoul (KR); Eun Bee Cho, Seoul (KR); Junho Chung, Seongnam-si (KR); Junyeong Jin, Gwachun-si (KR); Tae Young Yune, Seoul (KR); Jee Youn Lee, Seoul (KR)

(73) Assignee: Neuracle Science Co., Ltd., Seoul (KR)

( * ) Notice: Subject to any disclaimer, the term of this patent is extended or adjusted under 35 U.S.C. 154(b) by 70 days.

(21) Appl. No.: 16/348,058

(22) PCT Filed: Nov. 7, 2017

(86) PCT No.: PCT/IB2017/001490
§ 371 (c)(1),
(2) Date: May 7, 2019

(87) PCT Pub. No.: WO2018/083538
PCT Pub. Date: May 11, 2018

(65) Prior Publication Data
US 2019/0300599 A1  Oct. 3, 2019

Related U.S. Application Data

(60) Provisional application No. 62/418,674, filed on Nov. 7, 2016.

(51) Int. Cl.
*C07K 16/18* (2006.01)
*C07K 7/00* (2006.01)
*A61K 39/00* (2006.01)
*G01N 33/563* (2006.01)

(52) U.S. Cl.
CPC ............... *C07K 16/18* (2013.01); *C07K 7/00* (2013.01); *G01N 33/563* (2013.01); *A61K 2039/505* (2013.01); *C07K 2317/23* (2013.01); *C07K 2317/33* (2013.01); *C07K 2317/34* (2013.01); *C07K 2317/622* (2013.01); *C07K 2317/92* (2013.01)

(58) Field of Classification Search
CPC ............... C07K 16/18; A61K 39/3955; A61K 2039/505
See application file for complete search history.

(56) References Cited

U.S. PATENT DOCUMENTS

| 4,044,126 | A | 8/1977 | Cook et al. |
|---|---|---|---|
| 4,364,923 | A | 12/1982 | Cook et al. |
| 4,414,209 | A | 11/1983 | Cook et al. |
| 5,693,780 | A | 12/1997 | Newman et al. |
| 5,709,874 | A | 1/1998 | Hanson et al. |
| 5,759,542 | A | 6/1998 | Gurewich |
| 5,840,674 | A | 11/1998 | Yatvin et al. |
| 5,860,957 | A | 1/1999 | Jacobsen et al. |
| 5,900,252 | A | 5/1999 | Calanchi et al. |
| 5,948,433 | A | 9/1999 | Burton et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |

(Continued)

FOREIGN PATENT DOCUMENTS

| KR | 20160101786 A | 8/2016 |
|---|---|---|
| WO | WO-9712622 A1 | 4/1997 |

(Continued)

OTHER PUBLICATIONS

Burda et al. Reactive Gliosis and the Multicellular Response to CNS Damage and Disease. Neuron, 2014; 81(2): 229-248 (Year: 2014).*
Altschul, S.F., et al., "Gapped BLAST and PSI-BLAST: A New Generation of Protein Database Search Programs," Nucleic Acids Research 25(17):3389-3402, Oxford University Press, England (Sep. 1997).
An, Z., et al., "IgG2m4, an Engineered Antibody Isotype with Reduced Fc function," Mabs 1(6):572-579, Philadelphia, PA : Taylor & Francis, United States (Nov.-Dec. 2009).
Bataller R. et al., "Liver fibrosis", The Journal of Clinical Investigation 115(2): 209-218, BMC, England (Feb. 2005).
Bird, R.E., et al., "Single-chain Antigen-binding Proteins," Science 242(4877):423-426, Association for the Advancement of Science, United States (Oct. 1988).

(Continued)

*Primary Examiner* — Vanessa L. Ford
*Assistant Examiner* — Sandra Dillahunt
(74) *Attorney, Agent, or Firm* — Sterne, Kessler, Goldstein & Fox P.L.L.C.

(57) ABSTRACT

The present disclosure provides antibodies that specifically bind to human FAM19A5 and compositions comprising such antibodies. In a specific aspect, the antibodies specifically bind to human FAM19A5 and modulate FAM19A5 activity, e.g., inhibit, suppress, reduce, or reverse the onset of reactive gliosis and/or excessive proliferation of reactive astrocytes, utilizing such antibodies. The present disclosure also provides methods for treating disorders, such as central nervous system damage, a degenerative brain disorder, or a neuropathic pain, by administering an antibody that specifically binds to human FAM19A5.

20 Claims, 23 Drawing Sheets

Specification includes a Sequence Listing.

(56) References Cited

U.S. PATENT DOCUMENTS

| | | | |
|---|---|---|---|
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 9,579,398 | B2 | 2/2017 | Seong et al. |
| 2004/0014194 | A1 | 1/2004 | Beyer et al. |
| 2009/0221670 | A1 | 9/2009 | Borglum et al. |
| 2012/0100140 | A1 | 4/2012 | Reyes et al. |
| 2012/0261568 | A1 | 10/2012 | Coon et al. |
| 2015/0118230 | A1* | 4/2015 | Seong ............... A61K 38/1709 424/135.1 |
| 2016/0060705 | A1 | 3/2016 | O'Donnel et al. |

FOREIGN PATENT DOCUMENTS

| | | |
|---|---|---|
| WO | WO-9817815 A1 | 4/1998 |
| WO | WO-9817816 A1 | 4/1998 |
| WO | WO-9818934 A1 | 5/1998 |
| WO | WO-9931251 A1 | 6/1999 |
| WO | WO-2006005586 A2 | 1/2006 |
| WO | WO-2015015000 A1 | 2/2015 |
| WO | WO-2018083538 A1 | 5/2018 |

OTHER PUBLICATIONS

Bricogne, G., "Bayesian Statistical Viewpoint on Structure Determination: Basic Concepts and Examples," Methods in Enzymology 276:361-423, Academic Press, United States (1997).

Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (Jan. 1993).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (Feb. 1993).

Burks, E.A., et al., "In vitro Scanning Saturation Mutagenesis of an Antibody Binding Pocket," Proceedings of the National Academy of Sciences USA 94(2):412-417, Plenum Publishing Corporation , United States (Jan. 1997).

Champe, M., et al., "Monoclonal Antibodies that Block the Activity of Leukocyte Function-Associated Antigen 1 Recognize Three Discrete Epitopes in the Inserted Domain of CD11a," The Journal of Biological Chemistry 270 (3):1388-1394, American Society for Biochemistry and Molecular Biology, United States (Jan. 1995).

Chayen, N.E., et al., "The Role of Oil in Macromolecular Crystallization," Structure 5(10):1269-1274, Cell Press, United States (Oct. 1997).

Cheung, R.C., et al., "Epitope-specific Antibody Response to the Surface Antigen of Duck Hepatitis B Virus in Infected Ducks," Virology 176(2):546-552, Academic Press, United States (Jun. 1990).

Chothia, C. and Lesk, A.M., "Canonical Structures for the Hypervariable Regions of Immunoglobulins," Journal of Molecular Biology 196(4):901-917, Elsevier Science, United States (Aug. 1987).

Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).

Diegelmann, R.F and Evans, M.C., "Wound Healing: An Overview of Acute, Fibrotic and Delayed Healing, " Frontiers in Bioscience 9:283-289, Frontiers in Bioscience, United States (Jan. 2004).

Edelman, G.M. et al., "The Covalent Structure of an Entire gammaG Immunoglobulin Molecule," Proceedings of the National Academy of Sciences USA 63(1):78-85, National Academy of Sciences, United States (May 1969).

Firth, B.G and Dunnmon, P.M., "Left Ventricular Dilatation and Failure Post-Myocardial Infarction: Pathophysiology and Possible Pharmacologic Interventions, " Cardiovascular Drugs and Therapy 4(5):1363-1374, Kluwer Academic for the International Society for Cardiovascular Pharmacotherapy, United States (Oct. 1990).

GenBank: AAF32220.1: scFV antibody V region, partial [synthetic construct] (Jul. 26, 2016).

GenBank: AJQ23617.1: immunoglobulin light chain variable region, partial [Gallus gallus] (Dec. 31, 2016).

Giannini, E., et al., "Validity and Clinical Utility of the Aspartate Aminotransferase-alanine Aminotransferase Ratio in Assessing Disease Severity and Prognosis in Patients With Hepatitis C Virus-related Chronic Liver Disease, " 163(2):218-224, American Medical Association, United States (Jan. 2003).

Gieger, R., et al., "Crystallogenesis of Biological Macromolecules: Facts and Perspectives," Acta Crystallographica. Section D, Biological Crystallography 50(Pt4):339-350, Wiley-Blackwell, United States (Jul. 1994).

Goodman, Z.D., "Grading and Staging Systems for Inflammation and Fibrosis in Chronic Liver Diseases, " Journal of Hepatology 47(4):598-607, Elsevier, Netherlands (Oct. 2007).

Gowda, S., et al., "A Review on Laboratory Liver Function Tests," The Pan African Medical Journal 3:17, African Field Epidemiology Network, Uganda (Nov. 2009).

Harmsen, M.M., et al.," Properties, Production, and Applications of Camelid Single-Domain Antibody Fragments," Applied Microbiology and Biotechnology 77(1),13-22, Springer International, Germany (Nov. 2007).

Huston, J.S., et al., "Protein Engineering of Antibody Binding Sites: Recovery of Specific Activity in an Anti-digoxin Single-chain Fv Analogue Produced in *Escherichia coli*," Proceedings of the National Academy of Sciences USA 85(16):5879-5883, National Academy of Sciences, United States (Aug. 1988).

International Search Report and Written Opinion for International Application No. PCT/IB2017/001490, Australian Patent Office, Australia, dated Dec. 21, 2017, 11 pages.

Jefferis, R., et al., "Human Immunoglobulin Allotypes: Possible Implications for Immunogenicity," Mabs 1(4):332-338, Taylor & Francis, United States (Jul.-Aug. 2009).

Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (Dec. 1971).

Kabat, E.A., et al., "Sequences of Proteins of Immunological Interest," 5th Edition, U.S. Department of Public Health and Human Services, Public Health Service, NIH publication No. 91-3242, National Institutes of Health, Bethesda (1991).

Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (Dec. 1986).

Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (Oct. 1999).

Kostelny, S.A., et al., "Formation of a Bispecific Antibody by the Use of Leucine Zippers," The Journal of Immunology 148(5):1547-1553, American Association of Immunologists, United States (Mar. 1992).

Kountouras J. et al., "Prolonged bile duct obstruction: a new experimental model for cirrhosis in the rat", Journal of Experimental Pathology 65(3):305-311, Blackwell, England (Jun. 1984).

Lau, et al., "Chimeric Anti-CD14 IGG2/4 Hybrid Antibodies for Therapeutic Intervention in Pig and Human Models of Inflammation", Journal of Immunology, vol. 191 (9), pp. 4769-4777 (Nov. 2013).

Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).

Lonberg N, et al., "Human antibodies from transgenic animals," Nature biotechnology, vol. 23 (9), pp. 1117-1125, (Sep. 2005).

(56) References Cited

OTHER PUBLICATIONS

McCafferty, J., et al., "Phage Antibodies: Filamentous Phage Displaying Antibody Variable Domains," Nature 348(6301):552-554, Nature Publishing Group, London (Dec. 1990).

McPherson, A., "Crystallization of Proteins From Polyethylene Glycol," The Journal of Biological Chemistry 251 (20):6300-6303, American Society for Biochemistry and Molecular Biology, United States (Oct. 1976).

McPherson A, et al., "Current approaches to macromolecular crystallization", European Journal of Biochemistry, 189(1): 1-23, (Apr. 1990).

Moldenhauer G, et al., "Identity of HML-1 antigen on intestinal intraepithelial T cells and of B-Iy7 antigen on hairy cell leukaemia", Scand J Immunol, vol. 32 (2), pp. 77-82, (Aug. 1990).

Morel, G.A., et al., "Monoclonal Antibodies to Bovine Serum Albumin: Affinity and Specificity Determinations," Molecular Immunology 25(1):7-15, Pergamon Press, England (Jan. 1988).

Needleman, S.B., et al., "A general method applicable to the search for similarities in the amino acid sequence of two proteins," J. Mol Biol 48 (3): 443-53, Elsevier, Netherlands (Mar. 1970).

Roux, K.H., et al., "Comparisons ofthe Ability of Human IgG3 Hinge Mutants, IgM, IgE, and IgA2, to form Small Immune Complexes: A Role for Flexibility and Geometry," The Journal of Immunology 161 (8):4083-4090, American Association of Immunologists, United States (Oct. 1998).

Roversi, p., et al., "Modelling Prior Distributions of Atoms for Macromolecular Refinement and Completion," Acta Crystallographica. Section D, Biological Crystallography 56(Pt10):1316-1323, International Union of Crystallography by Munksgaard, United States (Oct. 2000).

Songsivilai, S. and Lachmann, P.J., "Bispecific Antibody: A Tool for Diagnosis and Treatment of Disease," Clinical and Experimental Immunology 79(3):315-321, Blackwell Scientific Publications, England (Mar. 1990).

Stahli, C., et al., "Distinction of Epitopes by Monoclonal Antibodies.," Methods in Enzymology 92:242-253, Academic Press, United States (1983).

Talman V, et al., "Cardiac fibrosis in myocardial infarction-from repair and remodeling to regeneration", Cell and tissue research, vol. 365 (3), pp. 563-581 (Sep. 2016).

Tang, T., et al., "TAFA: a novel secreted family with conserved cysteine residues and restricted expression in the brain," Genomics 83:727-734, Elsevier, Netherlands (2004).

TSUKADA, S., et al., "Mechanisms of Liver Fibrosis," Clinica Chimica Acta, 364(1-2):33-60, Elsevier, Netherlands (Feb. 2006).

Vidarsson G, et al., "Igg Subclasses and Allotypes: From Structure to Effector Functions," Front Immunology 5:520, Frontiers Research Foundation, Switzerland (Oct. 2014).

Ward, E.S., et al., "Binding Activities of a Repertoire of Single Immunoglobulin Variable Domains Secreted from *Escherichia coli*," Nature 341(6242):544-546, Nature Publishing Group, England (Oct. 1989).

Wynn, T.A. and Ramalingam, T.R., "Mechanisms of Fibrosis: Therapeutic Translation for Fibrotic Disease," Nature Medicine 18(7):1028-1040, Nature Publishing Company, United States (Jul. 2012).

* cited by examiner

FIG. 6
TBI5D-HCl (0.1, 0.3, 1, 3, 5, 10 μg)
GFAP/Hoechst
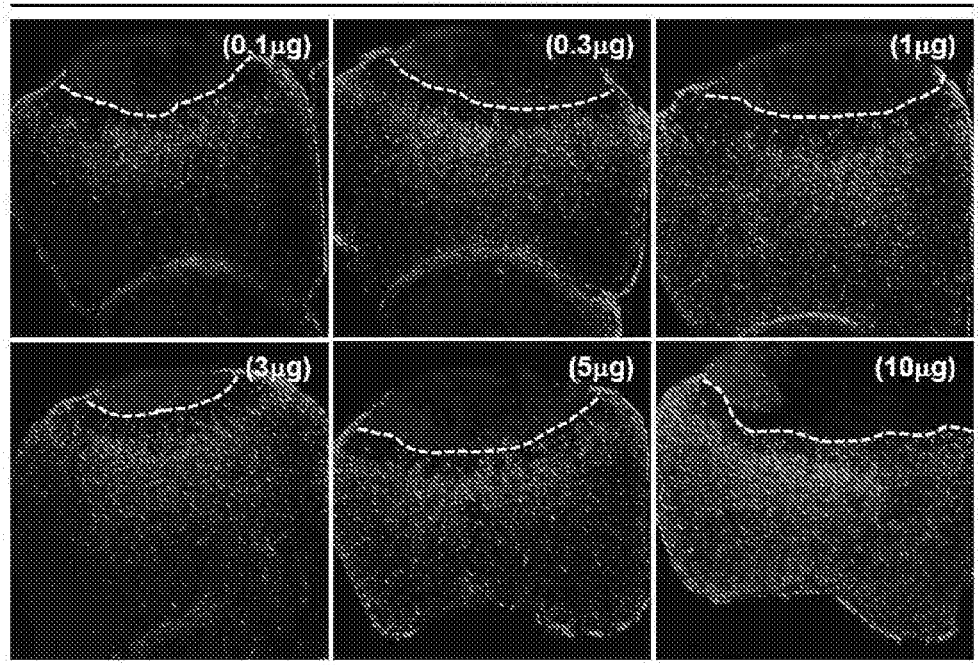
TBI5D-α-FAM19A5 monoclonal Ab (0.1, 0.3, 1, 3, 5, 10 μg)
GFAP/Hoechst
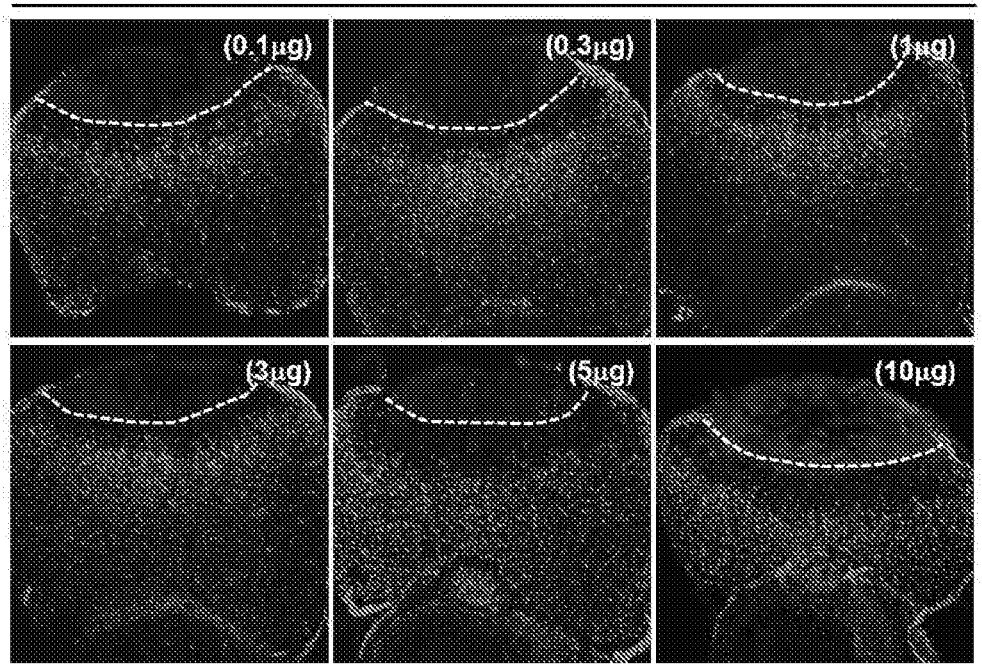

FIG. 8
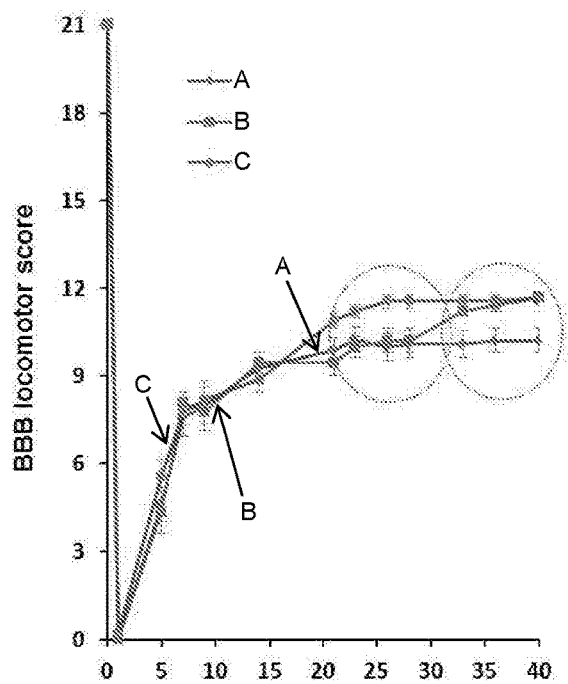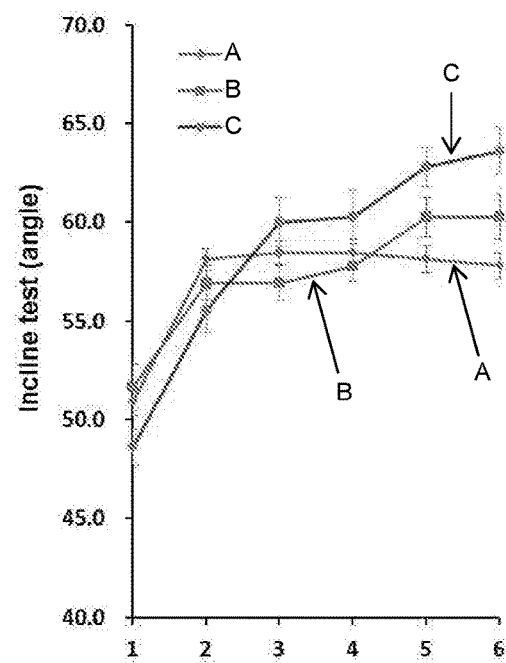

FIG. 10

QFLKEGQLAAGTCEIVTLDRDSSQPRRTIARQTARCACRKGQIAGTTRARPACVDARIIKTKQWCDMLPCLEGEGCDLLINRSGWTCTQPGGRIKTTTVS

QFLKEGQLAAGTSEIVTLDRDSSQPRRTIARQTARSASRKGQIAGTTRARPASVDARIIKTKQWSDMLPSLEGEGSDLLINRSGWTSTQPGGRIKTTTVS

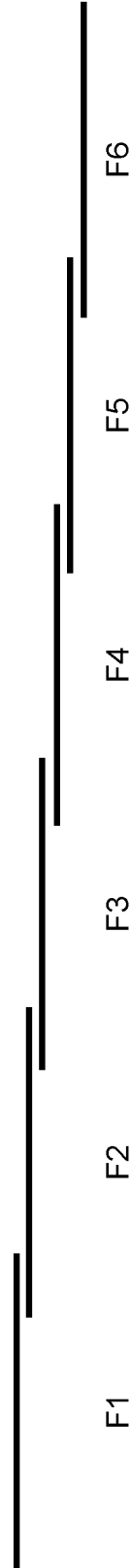

| F1 | F2 | F3 | F4 | F5 | F6 |

F1 : QFLKEGQLAAGTSEIVTLDRGGGSC-BSA (2.54 kDa)
F2 : TLDRDSSQPRRTIARQTARSGGGSC-BSA (2.68 kDa)
F3 : TARSASRKGQIAGTTRARPAGGGSC-BSA (2.42 kDa)
F4 : ARPASVDARIIKTKQWSDMLGGGSC-BSA (2.65 kDa)
F5 : SDMLPSLEGEGSDLLINRSGGGGSC-BSA (2.45 kDa)
F6 : NRSGWTSTQPGGRIKTTTVSGGGSC-BSA (2.50 kDa)

| Capture antibody | 1-65 | | | | P2-A03 | | | | P2-F11 | | | | 13B4 | | | | 2-13 | | | | 3-2 | | | |
|---|---|---|---|---|---|---|---|---|---|---|---|---|---|---|---|---|---|---|---|---|---|---|---|---|
| Detection antibody | 100 | 10 | 0 | S/N | 100 | 10 | 0 | S/N | 100 | 10 | 0 | S/N | 100 | 10 | 0 | S/N | 100 | 10 | 0 | S/N | 100 | 10 | 0 | S/N |
| 1-65 | 0.16 | 0.15 | 0.15 | | 0.16 | 0.11 | 0.1 | 1.1 | 1.61 | 0.33 | 0.19 | 1.7 | 0.19 | 0.15 | 0.15 | 1.0 | 1.73 | 1.81 | 0.55 | 3.3 | 1.98 | 1.83 | 0.28 | 6.5 |
| P2-A03 | 1.25 | 0.2 | 0.12 | 1.7 | | | | | 0.15 | 0.15 | 0.14 | 1.1 | 0.27 | 0.22 | 0.22 | 1.0 | 1.88 | 1.72 | 0.22 | 7.8 | 1.91 | 1.66 | 0.16 | 10 |
| P2-F11 | 0.12 | 0.12 | 0.12 | 1.0 | 0.09 | 0.09 | 0.09 | 1.0 | | | | | 0.2 | 0.18 | 0.18 | 1.0 | 1.83 | 2.04 | 0.29 | 7.0 | 2.02 | 1.81 | 0.13 | 13.9 |
| 13B4 | 1.88 | 0.44 | 0.1 | 4.1 | 0.15 | 0.16 | 0.14 | 1.1 | 0.14 | 0.16 | 0.15 | 1.1 | | | | | 1.92 | 0.65 | 0.21 | 3.1 | 1.7 | 0.3 | 0.13 | 2.3 |
| 2-13 | 2.02 | 1.8 | 0.44 | 4.1 | 1.88 | 1.07 | 0.39 | 2.7 | 1.94 | 1.91 | 0.4 | 4.8 | 1.48 | 0.45 | 0.4 | 1.1 | | | | | 2.01 | 1.97 | 0.38 | 5.1 |
| 3-2 | 1.98 | 1.68 | 0.1 | 16.8 | 1.83 | 1.08 | 0.05 | 21.6 | 2.11 | 1.93 | 0.09 | 21.4 | 1.88 | 0.42 | 0.09 | 4.7 | 2.04 | 2.02 | 0.26 | 7.8 | | | | |

Kd = 0.23 nM

Kd = 3.6 nM

Kd = 0.25 nM

Kd = 5.95 nM

| N'-Term His | 1-65 | 13B4 | 13F7 | h1-28 | h2-13 | h3-2 | P1-A03 | P1-A08 | P1-D03 | P1-F02 | P1-G09 | P2-A01 | P2-A03 | P2-C12 | P2-F07 | P2-F11 |
|---|---|---|---|---|---|---|---|---|---|---|---|---|---|---|---|---|
| Kd (nM) | 0.10 | 1.06 | 2.77 | 0.17 | 1.96 | 0.12 | 7.50 | 6.95 | 4.29 | 0.00 | 11.05 | 9.09 | 0.61 | 7.64 | 0.00 | 0.41 |
| Bmax | 3.259 | 2.839 | 3.035 | 2.938 | 2.407 | 3.006 | 2.454 | 0.4791 | 3.019 | 0.1723 | 0.738 | 1.191 | 3.367 | 1.726 | 0.1343 | 3.259 |
| R² | 0.8806 | 0.8823 | 0.9329 | 0.8703 | 0.9303 | 0.9021 | 0.9813 | -0.2016 | 0.9714 | 0.1299 | 0.6802 | 0.9105 | 0.9746 | 0.9422 | 0.2002 | 0.9692 |

ANTI-FAMILY WITH SEQUENCE SIMILARITY 19, MEMBER A5 ANTIBODIES AND METHOD OF USE THEREOF

CROSS REFERENCE TO RELATED APPLICATIONS

This application claims the priority benefit of U.S. Provisional Application No. 62/418,674, filed Nov. 7, 2016, which is hereby incorporated by reference in its entirety.

REFERENCE TO SEQUENCE LISTING SUBMITTED ELECTRONICALLY

The content of the electronically submitted sequence listing in ASCII text file (Name: 3763.003PC01_ST25.txt; Size: 133,676 bytes; and Date of Creation: Nov. 6, 2017) filed with the application is incorporated herein by reference in its entirety.

FIELD OF THE DISCLOSURE

The present disclosure provides antibodies that specifically bind to family with sequence similarity 19, member A5 (FAM19A5), compositions comprising such antibodies, and method of using such antibodies for preventing or treating disorders or diseases such as a central nervous system damage in a subject.

BACKGROUND OF THE DISCLOSURE

FAM19A5 is a member of the TAFA subfamily of proteins which is composed of five highly homologous small proteins. Tang T. Y. et al., *Genomics* 83(4):727-34 (2004). These proteins contain conserved cysteine residues at fixed positions, and are distantly related to macrophage inflammatory protein 1-alpha (MIP-1-alpha), a member of the CC-chemokine family. The TAFA proteins are predominantly expressed in specific regions of the brain and the spinal cord. These proteins are believed to be generated and secreted by adult neural stem cells in neurogenesis processes.

FAM19A5 is predominantly expressed in the brain of vertebrates and is believed that FAM19A5 is important in the development, differentiation, formation of a complete central nervous system, and can be used in the prevention or treatment of central nervous system injuries and/or diseases. U.S. Patent Publication No. 2015/0118230.

While inhibiting FAM19A5 can play an important role in treating the central nervous system, there is still a need to develop antibodies that specifically bind to FAM19A5 and that are capable of modulating FAM19A5 activity.

BRIEF SUMMARY OF THE DISCLOSURE

Disclosed herein is an antibody, such as a monoclonal antibody, or antigen binding portion thereof that specifically binds to human FAM19A5 (anti-FAM19A5 antibody), a composition comprising the antibody or antigen binding portion thereof, a nucleic acid encoding the antibody or antigen binding portion thereof, a vector comprising the nucleic acid or a cell comprising the vector.

In one embodiment, the anti-FAM19A5 antibody cross-competes for binding to a human FAM19A5 epitope with a reference antibody comprising (1) a heavy chain variable region (VH) comprising SEQ ID NO: 5 and a light chain variable region (VL) comprising SEQ ID NO: 6; (2) a heavy chain variable region (VH) comprising SEQ ID NO: 103 and a light chain variable region (VL) comprising SEQ ID NO: 114; (3) a heavy chain variable region (VH) comprising SEQ ID NO: 104 and a light chain variable region (VL) comprising SEQ ID NO: 115; (4) a heavy chain variable region (VH) comprising SEQ ID NO: 105 and a light chain variable region (VL) comprising SEQ ID NO: 116; (5) a heavy chain variable region (VH) comprising SEQ ID NO: 106 and a light chain variable region (VL) comprising SEQ ID NO: 117; (6) a heavy chain variable region (VH) comprising SEQ ID NO: 107 and a light chain variable region (VL) comprising SEQ ID NO: 118; (7) a heavy chain variable region (VH) comprising SEQ ID NO: 108 and a light chain variable region (VL) comprising SEQ ID NO: 119; (8) a heavy chain variable region (VH) comprising SEQ ID NO: 109 and a light chain variable region (VL) comprising SEQ ID NO: 120; (9) a heavy chain variable region (VH) comprising SEQ ID NO: 110 and a light chain variable region (VL) comprising SEQ ID NO: 121; (10) a heavy chain variable region (VH) comprising SEQ ID NO: 111 and a light chain variable region (VL) comprising SEQ ID NO: 122; (11) a heavy chain variable region (VH) comprising SEQ ID NO: 112 and a light chain variable region (VL) comprising SEQ ID NO: 123; or (12) a heavy chain variable region (VH) comprising SEQ ID NO: 113 and a light chain variable region (VL) comprising SEQ ID NO: 124. In one embodiment, the anti-FAM19A5 antibody binds to the same FAM19A5 epitope as the reference antibody.

In one embodiment, the anti-FAM19A5 antibody binds to at least one FAM19A5 epitope, which is SEQ ID NO: 2, at one or more amino acids corresponding to amino acid residues 99 to 107 (i.e., EGCDLLINR), e.g., amino acid residues 102, 103, 105, and 107 (i.e., DL-I-R), e.g., amino acid residues 99, 100, 102, 103, 105, and 107 (i.e., EG-DL-I-R), e.g., amino acid residues 99, 100, and 107 (i.e., EG------R) of SEQ ID NO: 4. In one embodiment, the anti-FAM19A5 antibody binds to at least one FAM19A5 epitope identified as EP6, EP7, and/or EP8, wherein EP6 comprises, consists essentially of, or consists of the amino acids KTKQWCDML (SEQ ID NO: 139), wherein EP7 comprises, consists essentially of, or consists of the amino acids GCDLLINR (SEQ ID NO: 140), and wherein EP8 comprises, consists essentially of, or consists of the amino acids TCTQPGGR (SEQ ID NO: 141).

In one embodiment, the anti-FAM19A5 antibody comprises a heavy chain CDR1, CDR2, and CDR3 and a light chain CDR1, CDR2, and CDR3, (i) wherein the heavy chain CDR3 comprises SEQ ID NO: 9, SEQ ID NO: 31, SEQ ID NO: 37, SEQ ID NO: 43, SEQ ID NO: 49, SEQ ID NO: 55, SEQ ID NO: 61, SEQ ID NO: 67, SEQ ID NO: 73, SEQ ID NO: 79, SEQ ID NO: 85, or SEQ ID NO: 91; (ii) wherein the heavy chain CDR1 comprises SEQ ID NO: 7, SEQ ID NO: 29, SEQ ID NO: 35, SEQ ID NO:41, SEQ ID NO: 47, SEQ ID NO: 53, SEQ ID NO: 59, SEQ ID NO: 65, SEQ ID NO: 71, SEQ ID NO: 77, SEQ ID NO: 83, or SEQ ID NO: 89; (iii) wherein the heavy chain CDR2 comprises SEQ ID NO: 8, SEQ ID NO: 30, SEQ ID NO: 36, SEQ ID NO: 42, SEQ ID NO: 48, SEQ ID NO: 54, SEQ ID NO: 60, SEQ ID NO: 66, SEQ ID NO: 72, SEQ ID NO: 78, SEQ ID NO: 84, or SEQ ID NO: 90; (iv) wherein the light chain CDR1 comprises SEQ ID NO: 10, SEQ ID NO: 32, SEQ ID NO: 38, SEQ ID NO: 44, SEQ ID NO: 50, SEQ ID NO: 56, SEQ ID NO: 62, SEQ ID NO: 68, SEQ ID NO: 74, SEQ ID NO: 80, SEQ ID NO: 86, or SEQ ID NO: 92; (v) wherein the light chain CDR2 comprises SEQ ID NO: 11, SEQ ID NO: 33, SEQ ID NO: 39, SEQ ID NO: 45, SEQ ID NO: 51, SEQ ID NO: 57, SEQ ID NO: 63, SEQ ID NO: 69, SEQ ID NO: 75, SEQ ID NO: 81, SEQ ID NO: 87, or SEQ ID NO: 93; and/or (vi) wherein the light chain CDR3 comprises SEQ ID NO: 12, SEQ ID NO: 34, SEQ ID NO: 40, SEQ ID NO: 46, SEQ ID NO: 52, SEQ ID NO: 58, SEQ ID NO: 64, SEQ ID NO: 70, SEQ ID NO: 76, SEQ ID NO: 82, SEQ ID NO: 88, or SEQ ID NO: 94.

In one embodiment, the anti-FAN/119A5 antibody comprises: (1) a heavy chain variable region (VH) comprising SEQ ID NO: 5 and a light chain variable region (VL) comprising SEQ ID NO: 6; (2) a heavy chain variable region (VH) comprising SEQ ID NO: 103 and a light chain variable region (VL) comprising SEQ ID NO: 114; (3) a heavy chain variable region (VH) comprising SEQ ID NO: 104 and a light chain variable region (VL) comprising SEQ ID NO: 115; (4) a heavy chain variable region (VH) comprising SEQ ID NO: 105 and a light chain variable region (VL) comprising SEQ ID NO: 116; (5) a heavy chain variable region (VH) comprising SEQ ID NO: 106 and a light chain variable region (VL) comprising SEQ ID NO: 117; (6) a heavy chain variable region (VH) comprising SEQ ID NO: 107 and a light chain variable region (VL) comprising SEQ ID NO: 118; (7) a heavy chain variable region (VH) comprising SEQ ID NO: 108 and a light chain variable region (VL) comprising SEQ ID NO: 119; (8) a heavy chain variable region (VH) comprising SEQ ID NO: 109 and a light chain variable region (VL) comprising SEQ ID NO: 120; (9) a heavy chain variable region (VH) comprising SEQ ID NO: 110 and a light chain variable region (VL) comprising SEQ ID NO: 121; (10) a heavy chain variable region (VH) comprising SEQ ID NO: 111 and a light chain variable region (VL) comprising SEQ ID NO: 122; (11) a heavy chain variable region (VH) comprising SEQ ID NO: 112 and a light chain variable region (VL) comprising SEQ ID NO: 123; or (12) a heavy chain variable region (VH) comprising SEQ ID NO: 113 and a light chain variable region (VL) comprising SEQ ID NO: 124.

In one embodiment, the anti-FAM19A5 antibody comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 5 and 103-113 and/or wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 6 and 114 to 124.

In one embodiment, the anti-FAM19A5 antibody is a chimeric antibody, a human antibody, or a humanized antibody.

In one embodiment, the anti-FAM19A5 antibody comprises a heavy chain comprising SEQ ID NOs: 27 and 145 to 155 and a light chain comprising SEQ ID NOs: 28 and 156 to 166.

In one embodiment, the anti-FAM19A5 antibody exhibits one or more of the following properties:
(a) binds to soluble human FAM19A5 with a KD of 10 nM or less as measured by enzyme-linked immunosorbent assay (ELISA);
(b) binds to membrane bound human FAM19A5 with a KD of 10 nM or less as measured by ELISA;
(c) reduces, reverses, delays, and/or prevents an onset of reactive gliosis;
(d) suppresses an excessive proliferation of reactive astrocytes;
(e) decreases expression of chondroitin sulfate proteoglycans including neurocan and neuron-glial antigen 2 (NG2);
(f) increases expression of c-fos and pERK in the nucleus of neurons;
(g) promotes survival of neurons;
(h) increases expression of GAP43 in neurons; and
(i) promotes regrowth of an axon.

In one embodiment, the present disclosure provides a FAM19A5 epitope consisting essentially of or consisting of an amino acid sequence at least 90%, at least about 95%, at least about 96%, at least about 97%, at least about 98%, at least about 99%, or about 100% identical to SEQ ID NOs: 2 and 139 to 141, wherein the epitope is capable of being specifically bound to a reference antibody comprising a heavy chain variable region and a light chain variable region as set forth in Tables 4 and 5, respectively.

In one embodiment, the present disclosure provides a nucleic acid encoding the anti-FAM19A5 antibody or the epitope disclosed herein.

In one embodiment, the present disclosure provides a composition comprising the anti-FAM19A5 antibody disclosed herein, and a carrier.

In one embodiment, the present disclosure provides an anti-FAM19A5 antibody for use in therapy of a disease or condition.

EMBODIMENTS

Embodiment 1

An isolated monoclonal antibody, or antigen binding portion thereof, which specifically binds to human family with sequence similarity 19, member A5 (FAM19A5) and exhibits one or more of the following properties:
(a) binds to soluble human FAM19A5 with a $K_D$ of 10 nM or less as measured by enzyme-linked immunosorbent assay (ELISA);
(b) binds to membrane bound human FAM19A5 with a $K_D$ of 10 nM or less as measured by ELISA;
(c) reduces, reverses, delays, and/or prevents an onset of reactive gliosis;
(d) suppresses an excessive proliferation of reactive astrocytes;
(e) decreases expression of chondroitin sulfate proteoglycans including neurocan and neuron-glial antigen 2 (NG2);
(f) increases expression of c-fos and pERK in the nucleus of neurons;
(g) promotes survival of neurons;
(h) increases expression of GAP43 in neurons; and
(i) promotes regrowth of an axon.

Embodiment 2

An isolated monoclonal antibody, or antigen binding portion thereof, which cross-competes for binding to a human FAM19A5 epitope with a reference antibody comprising heavy chain CDR1, CDR2, and CDR3 and light chain CDR1, CDR2, and CDR3, wherein the heavy chain CDR1 comprises the amino acid sequence of SEQ ID NO: 7, the heavy chain CDR2 comprises the amino acid sequence of SEQ ID NO: 8, the heavy chain CDR3 comprises the amino acid sequence of SEQ ID NO: 9, the light chain CDR1 comprises the amino acid sequence of SEQ ID NO: 10, the light chain CDR2 comprises the amino acid sequence of SEQ ID NO: 11, and the light chain CDR3 comprises the amino acid sequence of SEQ ID NO: 12.

Embodiment 3

An isolated monoclonal antibody, or antigen binding portion thereof, which binds to the same FAM19A5 epitope as a reference antibody comprising heavy chain CDR1, CDR2, and CDR3 and light chain CDR1, CDR2, and CDR3, wherein the heavy chain CDR1 comprises the amino acid sequence of SEQ ID NO: 7, the heavy chain CDR2 comprises the amino acid sequence of SEQ ID NO: 8, the heavy chain CDR3 comprises the amino acid sequence of SEQ ID NO: 9, the light chain CDR1 comprises the amino acid sequence of SEQ ID NO: 10, the light chain CDR2 comprises the amino acid sequence of SEQ ID NO: 11, and the light chain CDR3 comprises the amino acid sequence of SEQ ID NO: 12.

Embodiment 4

The monoclonal antibody, or antigen binding portion thereof, of Embodiment 2 or 3, which binds to at least one FAM19A5 epitope, which is SEQ ID NO: 2.

Embodiment 5

The monoclonal antibody, or antigen binding portion thereof, of any one of Embodiments 2 to 4, wherein the antibody, or antigen binding portion thereof, binds only to an FAM19A5, which is SEQ ID NO: 2.

Embodiment 6

The monoclonal antibody, or antigen binding portion thereof, of any one of Embodiments 2 to 4, wherein the antibody, or antigen binding portion thereof, further binds to an additional FAM19A5 epitope.

Embodiment 7

The monoclonal antibody, or antigen binding portion thereof, of any one of Embodiments 2 to 4, wherein the antibody, or antigen binding portion thereof, further binds to an additional FAM19A5 epitope selected from the group consisting of SEQ ID NO: 13, SEQ ID NO: 14, SEQ ID NO: 15, SEQ ID NO: 16, SEQ ID NO: 17, and any combination thereof.

Embodiment 8

The monoclonal antibody, or antigen binding portion thereof, of any one of the preceding Embodiments, wherein the monoclonal antibody, or antigen binding portion thereof comprises heavy chain CDR1, CDR2, and CDR3 and light chain CDR1, CDR2, and CDR3.

Embodiment 9

The monoclonal antibody, or antigen binding portion thereof, of Embodiment 8, wherein the heavy chain CDR3 of the monoclonal antibody, or antigen binding portion thereof, comprises SEQ ID NO: 9.

Embodiment 10

The monoclonal antibody, or antigen binding portion thereof, of Embodiment 8 or 9, wherein the heavy chain CDR1 of the monoclonal antibody, or antigen binding portion thereof, comprises SEQ ID NO: 7.

Embodiment 11

The monoclonal antibody, or antigen binding portion thereof, of any one of Embodiments 8 to 10, wherein the heavy chain CDR2 of the monoclonal antibody, or antigen binding portion thereof, comprises SEQ ID NO: 8.

Embodiment 12

The monoclonal antibody, or antigen binding portion thereof, of any one of Embodiments 8 to 11, wherein the light chain CDR1 of the monoclonal antibody, or antigen binding portion thereof, comprises SEQ ID NO: 10.

Embodiment 13

The monoclonal antibody, or antigen binding portion thereof, of any one of Embodiments 8 to 12, wherein the light chain CDR2 of the monoclonal antibody, or antigen binding portion thereof, comprises SEQ ID NO: 11.

Embodiment 14

The monoclonal antibody, or antigen binding portion thereof, of any one of Embodiments 8 to 13, wherein the light chain CDR3 of the monoclonal antibody, or antigen binding portion thereof, comprises SEQ ID NO: 12.

Embodiment 15

The monoclonal antibody, or antigen binding portion thereof, of any preceding Embodiments, which comprises a heavy chain variable domain comprising SEQ ID NO: 5 and a light chain variable domain comprising SEQ ID NO: 6.

Embodiment 16

The monoclonal antibody, or antigen binding portion thereof, of any preceding Embodiments, which comprises a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 5.

Embodiment 17

The monoclonal antibody, or antigen binding portion thereof, of any preceding Embodiments, which comprises a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NO: 6.

Embodiment 18

The monoclonal antibody of any one of preceding Embodiments, wherein the antibody is a single domain antibody.

Embodiment 19

The monoclonal antibody, or antigen binding portion thereof, of any one of the preceding Embodiments, wherein the antibody is selected from the group consisting of an IgG1, an IgG2, an IgG3, an IgG4, and a variant thereof.

Embodiment 20

The monoclonal antibody, or antigen binding portion thereof, of Embodiment 19, wherein the antibody is an IgG2 antibody, an IgG4 antibody, or the combination thereof.

Embodiment 21

The monoclonal antibody, or antigen binding portion thereof, of Embodiment 19, wherein the antibody comprises an IgG2/IgG4 isotype antibody.

Embodiment 22

The monoclonal antibody, or antigen binding portion thereof, of any one of the preceding Embodiments, further comprising a constant region without the Fc function.

Embodiment 23

The monoclonal antibody, or antigen binding portion thereof, of any preceding Embodiments, which is a chimeric antibody, a human antibody, or a humanized antibody.

Embodiment 24

The monoclonal antibody of any one of Embodiments 1 to 23, wherein the monoclonal antibody comprises a heavy chain comprising SEQ ID NO: 27 and a light chain comprising SEQ ID NO: 28.

Embodiment 25

The antigen binding portion thereof of any one of Embodiments 1 to 23, wherein the antigen binding portion thereof is an Fab, an Fab', an F(ab')2, an Fv, or a single chain Fv (scFv).

Embodiment 26

A bispecific molecule comprising the monoclonal antibody, or antigen binding portion thereof, of any one of the preceding Embodiments linked to a molecule having a second binding moiety.

Embodiment 27

A human family with sequence similarity 19, member A5 (FAM19A5) epitope consisting essentially of or consisting of an amino acid sequence at least 90%, at least about 95%, at least about 96%, at least about 97%, at least about 98%, at least about 99%, or about 100% identical to SEQ ID NO: 2, wherein the epitope is capable of being specifically bound to a reference antibody comprising a heavy chain variable region of SEQ ID NO: 5 and a light chain variable region of SEQ ID NO: 6.

Embodiment 28

A nucleic acid encoding the monoclonal antibody, or antigen binding portion thereof, of any one of Embodiments 1 to 25, the bispecific molecule of Embodiment 26, or the epitope of Embodiment 27.

Embodiment 29

A vector comprising the nucleic acid of Embodiment 28.

Embodiment 30

The vector of Embodiment 29, for use in gene therapy.

Embodiment 31

A cell transformed with an expression vector of Embodiment 29.

Embodiment 32

An immunoconjugate comprising the monoclonal antibody, or antigen binding portion thereof, according to any one of Embodiments 1 to 25 or the bispecific molecule of Embodiment 26, linked to an agent.

Embodiment 33

A composition comprising the monoclonal antibody, or antigen binding portion thereof, of any one of Embodiments 1 to 25, the bispecific molecule of Embodiment 26, or the immunoconjugate of Embodiment 32, and a carrier.

Embodiment 34

A kit comprising the monoclonal antibody, or antigen binding portion thereof, of any one of Embodiments 1 to 25, the bispecific molecule of Embodiment 26, or the immunoconjugate of Embodiment 32 and instructions for use.

Embodiment 35

A method of preparing an anti-FAM19A5 antibody, or antigen binding portion thereof, comprising immunizing a non-human animal with the epitope of Embodiment 27 and producing an antibody, or antigen binding portion thereof.

Embodiment 36

A method of producing an anti-FAM19A5 antibody, or antigen binding portion thereof, comprising culturing the host cell of Embodiment 31 under suitable condition and isolating the antibody or antigen binding portion thereof.

Embodiment 37

A method of reducing, reversing, delaying, and/or preventing an onset of reactive gliosis in a subject in need thereof comprising administering the monoclonal antibody, or antigen binding portion thereof of Embodiment 1 to 25, the bispecific molecule of Embodiment 26, or the immunoconjugate of Embodiment 32 such that the onset of gliosis is delayed.

Embodiment 38

A method of suppressing an excessive proliferation of reactive astrocytes in a subject in need thereof comprising administering the monoclonal antibody, or antigen binding portion thereof of Embodiment 1 to 25, the bispecific molecule of Embodiment 26, or the immunoconjugate of Embodiment 32 such that the excessive proliferation of reactive astrocytes is suppressed.

Embodiment 39

A method of decreasing expression of chondroitin sulfate proteoglycans including neurocan and neuron-glial antigen 2 (NG2) in a subject in need thereof comprising administering to the subject the monoclonal antibody, or antigen binding portion thereof of Embodiment 1 to 25, the bispecific molecule of Embodiment 26, or the immunoconjugate of Embodiment 32, wherein the chondroitin sulfate proteoglycans including neurocan and neuron-glial antigen 2 (NG2) are decreased.

Embodiment 40

A method of promoting survival of neurons in a subject in need thereof comprising administering to the subject the monoclonal antibody, or antigen binding portion thereof of Embodiment 1 to 25, the bispecific molecule of Embodiment 26, or the immunoconjugate of Embodiment 32, wherein the survival of neurons are promoted.

Embodiment 41

A method of promoting regrowth of an axon in a subject in need thereof comprising administering to the subject the monoclonal antibody, or antigen binding portion thereof of Embodiment 1 to 25, the bispecific molecule of Embodiment 26, or the immunoconjugate of Embodiment 32, wherein the regrowth of an axon is promoted.

Embodiment 42

A method of treating a central nervous system damage in a subject in need thereof comprising administering to the subject the monoclonal antibody, or antigen binding portion thereof, of Embodiment 1 to 25, the bispecific molecule of Embodiment 26, or the immunoconjugate of Embodiment 32.

Embodiment 43

The method of Embodiment 42, wherein the central nervous system damage comprises a traumatic brain injury, a cerebrospinal damage, a stroke and a brain tumor.

Embodiment 44

A method of treating a cerebrospinal or nerve disorder in a subject in need thereof comprising administering to the subject the monoclonal antibody, or antigen binding portion thereof, of Embodiment 1 to 25, the bispecific molecule of Embodiment 26, or the immunoconjugate of Embodiment 32.

Embodiment 45

The method of Embodiment 44, wherein the degenerative brain disorder comprises Huntington's disease, Parkinson's disease, Alzheimer's disease, multiple sclerosis, and Amyotrophic Lateral Sclerosis (ALS).

Embodiment 46

A method of treating a neuropathic pain in a subject in need thereof comprising administering to the subject the monoclonal antibody, or antigen binding portion thereof, of Embodiment 1 to 25, the bispecific molecule of Embodiment 26, or the immunoconjugate of Embodiment 32.

Embodiment 47

The method of any one of Embodiments 35 to 46, wherein the monoclonal antibody, or antigen binding portion thereof, is administered intravenously, orally, parenterally, intrathecally, intra-cerebroventricularly, pulmonarily, subcutaneously, or intraventricularly.

Embodiment 48

The method of any one of Embodiments 35 to 47, wherein the subject is a human.

Embodiment 49

Use of the monoclonal antibody, or antigen binding portion thereof, according to any one of the Embodiments 1 to 25, the bispecific molecule of Embodiment 26, or the immunoconjugate of Embodiment 32 for the manufacture of a medicament for the treatment of a central nervous system damage, a degenerative brain disorder, or a neuropathic pain.

Embodiment 50

The monoclonal antibody, or antigen binding portion thereof, of any of Embodiments 1 to 49 for use in therapy of a disease or condition.

Embodiment 51

The monoclonal antibody, or antigen binding portion thereof, for use of Embodiment 50, wherein the disease or condition is a cerebrospinal system damage, a degenerative cerebrospinal or nerve disorder, or a neuropathic pain.

Embodiment 52

A method of diagnosing a subject in need thereof comprising contacting a biological sample of the subject with the monoclonal antibody of any one of Embodiments 1 to 49.

BRIEF DESCRIPTION OF THE DRAWINGS

FIGS. 1A, 1B, and 1C show the analysis of 96 clones from the $3^{rd}$ order, $4^{th}$ order, or $5^{th}$ order bio-panning derived from the first chicken, the second chicken, and the third chicken, respectively.

FIG. 6 shows that the chimeric anti-FAM19A5-IgG2/4 monoclonal antibody (1-65) (bottom panel) inhibits, reduces, delays, and/or reverses the onset of gliosis in traumatic brain injury (TBI) mouse model. Normal human control immunoglobulin (HCI) was used as a control (top panel). The anti-FAM19A5 antibody or the control antibody were administered to the mice at one of the following concentrations: 0.1 μg, 0.3 μg, 1 μg, 3 μg, 5 μg, or 10 μg.

FIG. 8 shows the results of functional recovery of animals with spinal cord injury treated with humanized anti-FAM19A5-IgG2/4 antibody (1-65) (circle, C group), rabbit anti-FAM19A5 polyclonal antibody (square, B group), or vehicle control (diamond, A group). Treatment of animal with anti-FAM19A5 antibodies improve the locomotor activity in both BBB locomotor analysis (left) and incline test (right). The table below each figure shows the specific score at different days post TBI induction ("dpi").

FIG. 10 shows the amino acid sequences of epitopes F1-F6 (conjugated to BSA) and their location on the human FAM19A5 polypeptide. The top amino acid sequence shown is the wild-type FAM19A5 isoform 2 (without the signal peptide). The second amino acid sequence shown is the same sequence but the cysteine residues were mutated to serine to reduce nonspecific activity during peptide synthesis. The size of the different epitope fragments are indicated in parentheses.

FIG. 12A shows results for the anti-FAM19A5 antibodies 1-65, 2-13, and 3-2. For the 3-2 antibody, two different isotypes are shown: human IgG1 ("h3-2") and mouse IgG1 ("m3-2"). FIG. 12B shows results for the P2-C12 antibody. For each of the antibodies, the $1^{st}$, $2^{nd}$, $3^{rd}$, $4^{th}$, $5^{th}$, and $6^{th}$ bars (starting from the left) represent binding to epitope fragments F1, F2, F3, F4, F5, and F6, respectively. The bar farthest to the right (black) represents the positive control (i.e., His tagged FAM19A5 protein). The exact O.D. value are indicated at the top of each bar.

FIG. 15A shows the results for anti-FAM19A5 antibodies 1-65, 1-28, 2-13, and 3-2. FIG. 15B shows the results for anti-FAM19A5 antibodies 13B4, 13F7, and 15A9. FIG. 15C shows the results for anti-FAM19A5 antibodies P1-A08, P1-F02, P1-G09, P2-A01, P2-A03, P2-C12, P2-F07, and P2-F11. In FIGS. 15A to 15C, the eight bars for each of the antibodies correspond to mutants M1 to M8 (moving from left to right).

In FIGS. 17A to 17D, each of the lines corresponds to a different concentration (i.e., 300 nM, 100 nM, 33 nM, 11 nM, 3.3 nM, or 1.1, nM) of the indicated anti-FAM19A5 antibody used in the test.

FIG. 18A shows the results as bar graphs for varying concentrations of the anti-FAM19A5 antibodies. FIG. 18B shows the Kd (nM) for the different anti-FAM19A5 antibodies.

FIG. 19A shows representative images for the antibody 13B4 at two different concentrations: 100 μg (two row) and 10 μg (bottom row). FIG. 19B shows six different representative images for the antibody 13F7. FIG. 19C shows three different representative images for the antibody 15A9. FIG. 19D shows three representative images for the antibodies P2-A03 (top row) and P2-F11 (bottom row). FIG. 19E show three representative images for the antibody P1-A03. In each of the images, the brain tissue sections were stained for GFAP (glial fibrillary acidic protein, green) and nestin (red), which are known to be induced in reactive astrocytes after brain injury. The dashed line denotes lesion border following exposure to the traumatic brain injury.

DETAILED DESCRIPTION OF THE DISCLOSURE

Figure 1A:
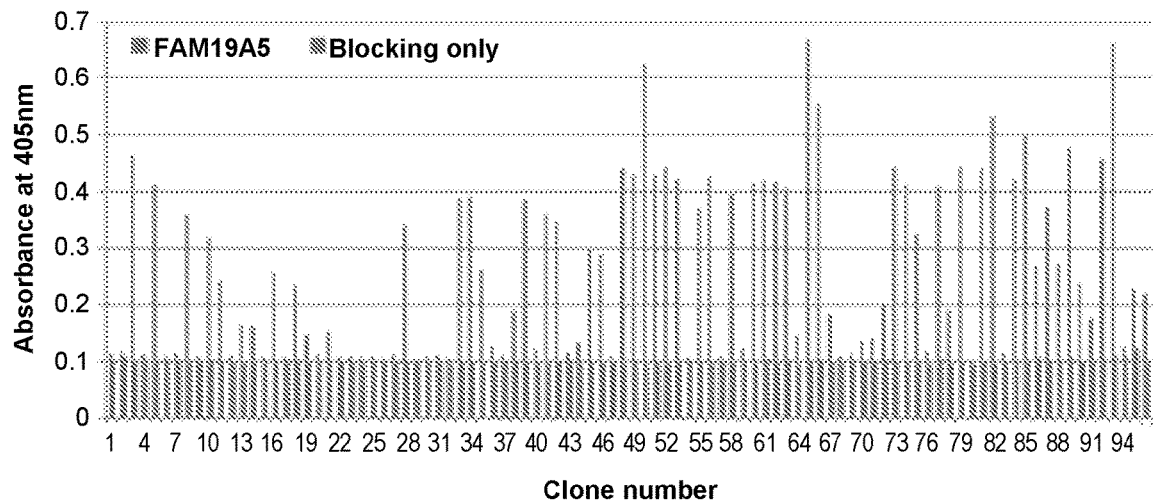
FIGS. 1A, 1B, and 1C show the binding analysis of individual scFv clones to FAM19A5 protein. The absorbance was measured at 405 nM. The clone numbers are indicated in the X axis.

Disclosed herein is an isolated monoclonal antibody, or antigen binding portion thereof, which specifically binds to human family with sequence similarity 19, member A5 (FAM19A5) and exhibits one or more of the properties disclosed herein.

In one embodiment, the monoclonal antibody, or antigen binding portion thereof cross-competes for binding to a human FAM19A5 epitope with a reference antibody comprising: a heavy chain and a light chain, wherein (i) the heavy chain CDR1 comprises the amino acid sequence of SEQ ID NO: 7; SEQ ID NO:29, SEQ ID NO: 35, SEQ ID NO:41, SEQ ID NO: 47, SEQ ID NO: 53, SEQ ID NO: 59, SEQ ID NO: 65, SEQ ID NO: 71, SEQ ID NO: 77, SEQ ID NO: 83, or SEQ ID NO: 89, (ii) the heavy chain CDR2 comprises the amino acid sequence of SEQ ID NO: 8; SEQ ID NO: 30, SEQ ID NO: 36, SEQ ID NO: 42, SEQ ID NO: 48, SEQ ID NO: 54, SEQ ID NO: 60, SEQ ID NO: 66, SEQ ID NO: 72, SEQ ID NO: 78, SEQ ID NO: 84, or SEQ ID NO: 90, and (iii) the heavy chain CDR3 comprises the amino acid sequence of SEQ ID NO: 9; SEQ ID NO: 31, SEQ ID NO: 37, SEQ ID NO: 43, SEQ ID NO: 49, SEQ ID NO: 55, SEQ ID NO: 61, SEQ ID NO: 67, SEQ ID NO: 73, SEQ ID NO: 79, SEQ ID NO: 85, or SEQ ID NO: 91. In some embodiments, (i) the light chain CDR1 comprises the amino acid sequence of SEQ ID NO: 10; SEQ ID NO: 32, SEQ ID NO: 38, SEQ ID NO: 44, SEQ ID NO: 50, SEQ ID NO: 56, SEQ ID NO: 62, SEQ ID NO: 68, SEQ ID NO: 74, SEQ ID NO: 80, SEQ ID NO: 86, or SEQ ID NO: 92, (ii) the light chain CDR2 comprises the amino acid sequence of SEQ ID NO: 11; SEQ ID NO: 33, SEQ ID NO: 39, SEQ ID NO: 45, SEQ ID NO: 51, SEQ ID NO: 57, SEQ ID NO: 63, SEQ ID NO: 69, SEQ ID NO: 75, SEQ ID NO: 81, SEQ ID NO: 87, or SEQ ID NO: 93, and (iii) the light chain CDR3 comprises the amino acid sequence of SEQ ID NO: 12; SEQ ID NO: 34, SEQ ID NO: 40, SEQ ID NO: 46, SEQ ID NO: 52, SEQ ID NO: 58, SEQ ID NO: 64, SEQ ID NO: 70, SEQ ID NO: 76, SEQ ID NO: 82, SEQ ID NO: 88, or SEQ ID NO: 94.

In some embodiments, the reference antibody comprises: (1) a heavy chain variable region (VH) comprising SEQ ID NO: 5 and a light chain variable region (VL) comprising SEQ ID NO: 6; (2) a heavy chain variable region (VH) comprising SEQ ID NO: 103 and a light chain variable region (VL) comprising SEQ ID NO: 114; (3) a heavy chain variable region (VH) comprising SEQ ID NO: 104 and a light chain variable region (VL) comprising SEQ ID NO: 115; (4) a heavy chain variable region (VH) comprising SEQ ID NO: 105 and a light chain variable region (VL) comprising SEQ ID NO: 116; (5) a heavy chain variable region (VH) comprising SEQ ID NO: 106 and a light chain variable region (VL) comprising SEQ ID NO: 117; (6) a heavy chain variable region (VH) comprising SEQ ID NO: 107 and a light chain variable region (VL) comprising SEQ ID NO: 118; (7) a heavy chain variable region (VH) comprising SEQ ID NO: 108 and a light chain variable region (VL) comprising SEQ ID NO: 119; (8) a heavy chain variable region (VH) comprising SEQ ID NO: 109 and a light chain variable region (VL) comprising SEQ ID NO: 120; (9) a heavy chain variable region (VH) comprising SEQ ID NO: 110 and a light chain variable region (VL) comprising SEQ ID NO: 121; (10) a heavy chain variable region (VH) comprising SEQ ID NO: 111 and a light chain variable region (VL) comprising SEQ ID NO: 122; (11) a heavy chain variable region (VH) comprising SEQ ID NO: 112 and a light chain variable region (VL) comprising SEQ ID NO: 123; or (12) a heavy chain variable region (VH) comprising SEQ ID NO: 113 and a light chain variable region (VL) comprising SEQ ID NO: 124.

In some embodiments, the monoclonal antibody, or antigen binding portion thereof, binds to at least one FAM19A5 epitope, which is SEQ ID NO: 2. In other embodiments, the monoclonal antibody, or antigen binding portion thereof, binds to only one FAM19A5 epitope, which is SEQ ID NO: 2. In some embodiments, the monoclonal antibody, or antigen binding portion thereof, further binds to an additional FAM19A5 epitope selected from the group consisting of SEQ ID NO: 13, SEQ ID NO: 14, SEQ ID NO: 15, SEQ ID NO: 16, SEQ ID NO: 17, and a combination thereof.

In some embodiments, the monoclonal antibody, or antigen binding portion thereof, binds to at least one FAM19A5 epitope identified as EP6, EP7, and/or EP8, wherein EP6 comprises, consists essentially of, or consists of the amino acids KTKQWCDML (SEQ ID NO: 139), wherein EP7 comprises, consists essentially of, or consists of the amino acids GCDLLINR (SEQ ID NO: 140), and wherein EP8 comprises, consists essentially of, or consists of the amino acids TCTQPGGR (SEQ ID NO: 141). In certain embodiments, the monoclonal antibody, or antigen binding portion thereof, only binds to EP6, EP7, and/or EP8. In other embodiments, the monoclonal antibody, or antigen binding portion thereof, further binds to an additional FAM19A5 epitope selected from the group consisting of SEQ ID NO: 134, SEQ ID NO: 135, SEQ ID NO: 136, SEQ ID NO: 137, SEQ ID NO: 138, and any combinations thereof.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "family with sequence similarity 19, member A5" or "FAM19A5" refers to a protein that belongs to the TAFA family (also known as FAM19 family) of five highly homologous proteins and is predominantly expressed in brain and the spinal cord. FAM19A5 is also known as TAFA5 or Chemokine-like protein TAFA-5.

In humans, the gene encoding FAM19A5 is located on chromosome 22. There are multiple human FAM19A5 (UniProt: Q7Z5A7) isoforms, which are believed to be produced by alternative splicing: isoform 1 (UniProt: Q7Z5A7-1), which consists of 132 amino acids, isoform 2 (UniProt: Q7Z5A7-2), which consists of 125 amino acids, and isoform 3 (UniProt: Q7Z5A7-3), which consists of 53 amino acids. Human FAM19A5 protein is believed to exist as both membrane bound and soluble (secreted) forms. Isoform 1 is believed to be a membrane with one transmembrane region. Isoform 2, which was reported in Tang T. Y. et al., *Genomics* 83(4):727-34 (2004) as a secreted protein (soluble), contains a signal peptide at amino acid positions 1-25. Isoform 1 is believed to be a membrane protein. Below are the amino acid sequences of the three known human FAM19A5 isoforms.

(I) Isoform 1 (UniProt: Q7Z5A7-1, transmembrane protein): this isoform has been chosen as the canonical sequence.
MAPSPRTGSR QDATALPSMS STFWAFMILA SLLIAYCSQL AAGTCEIVTL DRDSSQPRRT IARQTAR-CAC RKGQIAGTTR ARPACVDARI IKTKQWCDML PCLEGEGCDL LINRSGWTCT QPGGRIKTTT VS (SEQ ID NO: 1)

(II) Isoform 2 (UniProt: Q7Z5A7-2, soluble protein):
MQLLKALWAL AGAALCCFLV LVIHAQFLKE GQLAAGTCEI VTLDRDSSQP RRTIARQTAR CACRKGQIAG TTRARPACVD ARIIKTKQWC DMLPCLEGEG CDLLINRSGW TCTQPGGRIK TTTVS (SEQ ID NO: 4)

(III) Isoform 3 (UniProt: Q7Z5A7-3):
MYHHREWPAR IIKTKQWCDM LPCLEGEGCD LLINRSGWTC TQPGGRIKTT TVS (SEQ ID NO: 26)

The term "FAM19A5" includes any variants or isoforms of FAM19A5 which are naturally expressed by cells. Accordingly, antibodies described herein can cross-react with different isoforms in the same species (e.g., different isoforms of human FAM19A5), or cross-react with FAM19A5 from species other than human (e.g., mouse FAM19A5). Alternatively, the antibodies can be specific for human FAM19A5 and cannot exhibit any cross-reactivity with other species. FAM19A5 or any variants and isoforms thereof, can either be isolated from cells or tissues which naturally express them or be recombinantly produced. The polynucleotide encoding human FAM19A5 has the GenBank Accession No. BC039396 and the following sequence:

TABLE 1A

Polynucleotide sequence of human FAM19A5

Polynucleotide sequence (SEQ ID NO: 3)

| | |
|---|---|
| FAM19A5 (GenBank Accession No. BC039396) | ggcggcggag gatggcgcgc gcggggcccg cacgtggagg ccggcgcggg ggcgcgggca gggccggctg ctgagacgcg ctgctgcccc ccgcgcgggc gccgcggctt caatggcgcc atcgcccagg accggcagcc ggcaagatgc gaccgccctg cccagcatgt cctcaacttt ctgggcgttc atgatcctgg ccagcctgct catcgcctac tgcagtcagc tggccgcgg cacctgtgag attgtgacct tggaccggga cagcagccag cctcggagga cgatcgcccg gcagaccgcc cgctgtgcgt gtagaaaggg gcagatcgcc ggcaccacga gagcccggcc cgcctgtgtg gacgcaagaa tcatcaagac caagcagtgg tgtgacatgc ttccgtgtct ggagggggaa ggctgcgact tgttaatcaa ccggtcaggc tggacgtgca cgcagcccgg cgggaggata aagaccacca cggtctcctg acaaacacag ccctgaggg ggccccggga gtggccttgg ctccctggag agcccacgtc tcagccacag ttctccactc gcctcggact tcaccgttc tctgccgccc gcccactccg tttccctgtg gtccgtgaag gacggcctca ggccttggca tcctgagctt cggtctgtcc agccgacccg aggaggccgg actcagacac ataggcgggg ggcggcacct ggcatcagca atacgcagtc tgtgggagcc cggccgcgcc cagccccgc cgaccgtggc gttggccctg ctgtcctcag aggaggagga ggaggaggca gctccggcag ccacagaagg ctgcagccca gcccgcctga gacacgacgc ctgcccagg ggactgtcag gcacagaagc ggcctcctcc cgtgcccag actgtccgaa ttgcttttat tttcttatac tttcagtata ctccatagac caaagagcaa aatctatctg aacctggacg cacctcact gtcagggtcc ctggggtcgc ttgtgcgggc gggagggcaa tggtggcaga gacatgctgg tggcccggc ggagcggaga gggcggccgt ggtggaggcc tccacccag gagcacccg cacaccctcg gaggacgggc ttcggctgcg cggaggccgt ggcacacctg |

TABLE 1A-continued

Polynucleotide sequence of human FAM19A5

Polynucleotide sequence (SEQ ID NO: 3)

```
cgggaggcag cgacggcccc cacgcagacg ccgggaacgc aggccgcttt
attcctctgt acttagatca acttgaccgt actaaaatcc ctttctgttt
taaccagtta aacatgcctc ttctacagct ccatttttga tagttggata
atccagtatc tgccaagagc atgttgggtc tcccgtgact gctgcctcat
cgatacccca tttagctcca gaaagcaaag aaaactcgag taacacttgt
ttgaaagaga tcattaaatg tattttgcaa agcccaaaaa aaaaaaaaaa a
```

The terms "antibody" and "antibodies" are terms of art and can be used interchangeably herein and refer to a molecule with an antigen binding site that specifically binds an antigen. The terms as used to herein include whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. In another embodiment, an "antibody" refers to a single chain antibody comprising a single variable domain, e.g., VHH domain. Each heavy chain is comprised of a heavy chain variable region (abbreviated herein as VH) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

In a specific embodiment, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82. See TABLE 1B

TABLE 1B

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
|  |  |  | (Kabat Numbering) |
| H1 | H31-H35 | H26-H35 | H26-H32 |
|  |  |  | (Chothia Numbering) |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77 (2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969, *Proc. Natl. Acad. Sci. USA* 63(1):78-85, describing the amino acid sequence of myeloma protein EU, which is the first human IgG1 sequenced. The EU index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA or IgY), any class (e.g., Igd, IgG2, IgG3, IgG4, IgA1 or IgA2), or any subclass (e.g., IgG1, IgG2, IgG3 and IgG4 in humans, and IgG1, IgG2a, IgG2b and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain embodiments, the antibodies described herein are of the IgG1, IgG2, IgG3 or IgG4 subclass or any hybrid thereof. In certain embodiments, the antibodies are of the IgG2, IgG4 or IgG2/IgG4 subclass.

"Antibody" includes, by way of example, both naturally occurring and non-naturally occurring antibodies; monoclonal and polyclonal antibodies; chimeric and humanized antibodies; human and nonhuman antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; single chain antibodies; camelized antibodies; affybodies; anti-idiotypic (anti-Id) antibodies (including, e.g., anti-anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The term "antigen-binding portion" of an antibody, as used herein, refers to one or more fragments of an antibody that retain the ability to specifically bind to an antigen (e.g., human FAM19A5). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-FAM19A5 antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv) (v) a dAb fragment (Ward et al., (1989) Nature 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the term "constant region" or "constant domain" are interchangeable and have its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in an Fc region, i.e., it extends from about amino acid 341 to about amino acid 447 of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al., (2009) *mAbs* 1:1; Vidarsson G. et al., *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al., *Front Immunol.* 5:520 (published online Oct. 20, 2014).

The constant region can be manipulated, e.g., by recombinant technology, to eliminate one or more effector functions. An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')$_2$, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al., *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al., *J Immunol.* 191:4769-4777 (2013)), or an Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al., mAbs 1:6, 572-579 (2009); the disclosure of which are incorporated by reference to their entirety.

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al., *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges known in the art. See, e.g., Kabat E A et al., (1991) Sequences of Proteins of Immunological Interest, Fifth Edition, U.S. Department of Health and Human Services, NIH Publication No. 91-3242; Vidarsson G. et al., *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al., *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al., (2009) *mAbs* 1:1). Antibodies described herein can be of any allotype. Allotypes of IgG1, IgG2, IgG3, and IgG4 are known in the art. See, e.g., Kabat E A et al., (1991) supra; Vidarsson G. et al., *Front Immunol.* 5:520 (published online Oct. 20, 2014); and Lefranc M P, *mAbs* 1:4, 1-7 (2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to FAM19A5 is substantially free of antibodies that specifically bind antigens other than FAM19A5). An isolated antibody that specifically binds to an epitope of FAM19A5 can, however, have cross-reactivity to other FAM19A5 proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE® or kinetic exclusion assay (KinExA).

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by, e.g., immunoassays (e.g., ELISA) or surface plasmon resonance (SPR) technology in a BIACORE 2000 instrument using the predetermined antigen, but does not bind with high affinity to unrelated antigens.

As used herein, the term "antigen" refers to any natural or synthetic immunogenic substance, such as a protein, peptide, or hapten. An antigen can be FAM19A5 or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from FMAM19A5) are tested for reactivity with a given antibody (e.g., anti-FAM19A5 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Biol Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on FAM19A5" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)).

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to FAM19A5 from a different species. For example, an antibody described herein that binds human FAM19A5 can also bind another species of FAM19A5 (e.g., mouse FAM19A5). As used herein, cross-reactivity can be measured by detecting a specific reactivity with purified antigen in binding assays (e.g., SPR, ELISA) or binding to, or otherwise functionally interacting with, cells physiologically expressing FAM19A5. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a therapeutic agent or a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the term "onset of gliosis" or "onset of reactive gliosis" includes the beginning or initiation of gliosis. Gliosis is a nonspecific reactive change of glial cells in the central nervous system (CNS, e.g., brain and/or the spinal cord) in response to injury or damage from e.g., trauma, cerebrospinal damage, brain tumor, infection, ischemia, stroke, autoimmune responses, and/or neurodegenerative diseases, and includes the proliferation or hypertrophy of several different types of glial cells, including astrocytes, microglia, and oligodendrocytes. Onset of gliosis can lead to scar formation, which inhibits axonal regeneration in the part of the CNS that has been traumatized or injured. Detrimental effects of an onset of gliosis include irreversible or permanent damage to the neurons and/or prevention of the surrounding neurons from recovering. Accordingly, the terms "delay an onset of gliosis" and "delay an onset of reactive gliosis" include inhibit, slow down, suppress, or prevent the beginning or initiation of gliosis and its associated detrimental effects of the CNS.

As used herein, the term "excessive proliferation of reactive astrocytes" includes an abnormal increase in the number of astrocytes due to the destruction of nearby neurons from e.g., CNS damage, trauma, injury, cerebrospinal damage, brain tumor, infection, ischemia, stroke, autoimmune responses, and/or neurodegenerative disease. Excessive proliferation of reactive astrocytes can lead to detrimental effects in the CNS including scar formation, which inhibits axonal regeneration in the part of the CNS that has been traumatized or injured, exacerbation of inflammation, production and release of neurotoxic levels of reactive oxygen species, release of potentially excitotoxic glutamate, the potential contribution to seizure genesis, compromise of blood-brain barrier function, cytotoxic edema during trauma and stroke, potential for chronic cytokine activation of astrocytes to contribute to chronic pain, and secondary degeneration after CNS injury. Sofroniew, Michael V. (2009) *Trends in Neurosciences*, 32(12):638-47; McGraw, J. et al. (2001) *Journal of Neuroscience Research* 63(2):109-15; and Sofroniew, M. V. (2005) *The Neuroscientist* 11(5): 400-7. Accordingly, the terms "suppress excessive proliferation of reactive astrocytes" includes inhibit, slowing down, suppress, curb, or prevent excessive or abnormal proliferation of reactive astrocytes and its associated detrimental effects of the CNS.

As used herein, the term "chondroitin sulfate proteoglycans" includes proteoglycans composed of a protein core and a chondroitin sulfate. Chondroitin sulfate proteoglycans, also known as CSPGs, are extracellular matrix molecules widely expressed throughout the developing and adult CNS. CSGPs play key roles in neural development and glial scar formation, and they inhibit axon regeneration after injury in the CNS. Known CSPGs include aggrecan (CSPG1), versican (CSPG2), neurocan (CSPG3), CSPG4 (or neuron-glial antigen 2 (NG2)), CSPG5, SMC3 (CSPG6, structural maintenance of chromosomes 3), brevican (CSPG7), and CD44 (CSPG8, cluster of differentiation 44), phosphacanneurocan (CSPG3). Rhodes, K. E. and Fawcett, J. W. (2004) *Journal of Anatom.* 204(1):33-48. Thus, the term "decrease expression of chondroitin sulfate proteoglycans" includes decrease, inhibit, reduce the level of one or more CSGPs, or reduce the activity of or render inactive one or more CSGPs. In certain embodiments, the term includes decrease, inhibit, reduce the level of neurocan, NG2, or both, or reduce the activity of or render inactive neurocan, NG2, or both.

As used herein, the term "neuron" includes electrically excitable cells that process and transmit information through electrical and chemical signals. Neurons are the major components of the brain and spinal cord of the CNS, and of the ganglia of the peripheral nervous system (PNS), and can connect to each other to form neural networks. A typical neuron is composed of a cell body (soma), dendrites, and an axon. The soma (the cell body) of a neuron contains the nucleus. The dendrites of a neuron are cellular extensions with many branches, where the majority of input to the neuron occurs. The axon is a finer, cable-like projection extending from the soma and carries nerve signals away from the soma and certain types of information back to the soma. The term "promote regrowth of neuron" includes stimulating, promoting, increasing, or activating growth of neurons, preferably after injury or damage.

As used herein, the term "c-fos" includes the protooncogene c-fos, which is rapidly induced by stimulation of a neurotransmitter. c-fos exists in many species including mouse and human. The c-fos gene and protein are known and characterized. See Curran, T, The c-fos proto-oncogene, pp 307-327 (The Oncogene Handbook, Reddy E P et al., (eds.) Elsevier)(1988). The expression of c-fos can be determined by methods known in the art, e.g., Northern blot, quantitative PCR, or immunohistochemistry. The term "increases expression of c-fos" includes increase the level of c-fos mRNA, c-fos protein, or c-fos protein activity.

As used herein, the term "pERK" includes phosphorylated extracellular signal-regulated kinase. Extracellular signal-regulated kinase or ERK, includes ERK1 and ERK2, is a member of mitogen-activated protein kinase (MAPK) family. ERK is activated via phosphorylation by its upstream kinase to form pERK, which then activates down-stream targets. ERK is involved in neural and synaptic plasticity underlying learning, and memory and pain hypersensitivity. Ji R. R. et al., *Nat Neurosci* (1999) 2:1114-1119. The ERK gene, protein, phosphorylation, and activation are known and characterized, and the expression of ERK and pERK can be determined by methods known in the art (e.g., Northern blot, quantitative PCR, or immunohistochemistry). See Gao Y. J. and Ji R. R., *Open Pain J.* (2009) 2:11-17. The term "increase expression of pErk" includes increase the level of ERK mRNA, ERK protein, or pERK activity.

As used herein, the term "GAP43," also known as "growth Associated Protein 43," is a nervous tissue-specific protein that promotes neurite formation, regeneration, and plasticity. Benowitz L. I. and Routtenberg A. (1997) *Trends in Neurosciences* 20 (2): 84-91; Aarts L. H. et al., (1998) *Advances in Experimental Medicine and Biology* 446: 85-106. The human GAP43 is encoded by the GAP43 gene. Human GAP43 polypeptide sequence (UniProt: KB—P17677) and the cDNA sequence encoding the polypeptide are known in the art. Kosik K. S. et al., (1988) *Neuron* 1(2):127-32; Ng S. C. et al., (1988) *Neuron* 1(2): 133-9. The expression of GAP43 can be determined by methods known in the art (e.g., Northern blot, quantitative PCR, or immunohistochemistry). The term "increase GAP43 in neurons" includes enhancing or increasing the level of GAP43 mRNA, GAP43 protein, or increasing the activity of GAP43 protein.

The term "therapeutically effective amount" as used herein refers to an amount of a drug, alone or in combination with another therapeutic agent, effective to "treat" a disease or disorder in a subject or reduce the risk, potential, possibility or occurrence of a disease or disorder (e.g., a central nervous system damage). A "therapeutically effective amount" includes an amount of a drug or a therapeutic agent that provides some improvement or benefit to a subject having or at risk of having a disease or disorder (e.g., a central nervous system damage such as a traumatic brain injury or other disease disclosed herein). Thus, a "therapeutically effective" amount is an amount that reduces the risk, potential, possibility or occurrence of a disease or provides disorder or some alleviation, mitigation, and/or reduces at least one indicator (e.g., an onset of reactive gliosis), and/or decrease in at least one clinical symptom of a disease or disorder.

II. Anti-FAM19A5 Antibodies

Disclosed herein are antibodies, e.g., monoclonal antibodies, which are characterized by particular functional features or properties. For example, the antibodies specifically bind human FAM19A5, including soluble FAM19A5 and membrane bound FAM19A5. In addition to binding specifically to soluble and/or membrane bound human FAM19A5, the antibodies described herein exhibit one or more of the following functional properties:

(a) binds to soluble human FAM19A5 with a $K_D$ of 10 nM or less;
(b) binds to membrane bound human FAM19A5 with a $K_D$ of 10 nM or less;
(c) reduces, reverses, delays, and/or prevents an onset of reactive gliosis;
(d) suppresses an excessive proliferation of reactive astrocytes
(e) decreases expression of chondroitin sulfate proteoglycans including neurocan and neuron-glial antigen 2 (NG2);
(f) increases expression of c-fos and pERK in the nucleus of neurons;
(g) promotes survival of neurons.
(h) increases expression of GAP43 in neurons; and
(i) promotes regrowth of an axon.

In some embodiments, the anti-FAM19A5 antibody or antigen binding portion thereof specifically binds to soluble human FAM19A5 or membrane-bound human with high affinity, for example, with a $K_D$ of $10^{-7}$ M or less, $10^{-8}$ M or less, $10^{-9}$ M (1 nM) or less, $10^{-10}$ M (0.1 nM) or less, $10^{-11}$ M or less, or $10^{-12}$ M or less, e.g., $10^{-12}$ M to $10^{-7}$ M, $10^{-11}$ M to $10^{-7}$ M, $10^{-10}$ M to $10^{-7}$ M, or $10^{-9}$ M to $10^{-7}$ M, e.g., $10^{-12}$ M, $5\times10^{-12}$ M, $10^{-11}$ M, $5\times10^{-11}$ M, $10^{-10}$ M, $5\times10^{-10}$ M, $10^{-9}$ M, $5\times10^{-9}$ M, $10^{-8}$ M, $5\times10^{-8}$ M, $10^{-7}$ M, or $5\times10^{-7}$ M. Standard assays to evaluate the binding ability of the antibody toward human FAM19A5 of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by ELISA, BIACORE® analysis or KinExA. Assays to evaluate the effects of the antibodies on functional properties of FAM19A5 (e.g., ligand binding) are described in further detail infra and in the Examples.

In some embodiments, the anti-FAM19A5 antibody or antigen binding portion thereof binds to soluble human FAM19A5 with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In some embodiments, the anti-FAM19A5 antibody or antigen binding portion thereof binds to soluble FAM19A5 with a $K_D$ of 10 nM or less, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof specifically binds to soluble human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

In some embodiments, the anti-FAM19A5 antibody or antigen binding portion thereof binds to membrane-bound human with a $K_D$, e.g., as determined by ELISA, of $10^{-7}$ M or less, $10^{-8}$ M (10 nM) or less, $10^{-9}$ M (1 nM) or less, $10^{-10}$ M or less, $10^{-12}$ M to $10^{-7}$ M, $10^{-11}$ M to $10^{-7}$ M, $10^{-10}$ M to $10^{-7}$ M, $10^{-9}$ M to $10^{-7}$ M, or $10^{-8}$ M to $10^{-7}$ M. In certain embodiments, the anti-FAM19A5 antibody or antigen binding portion thereof specifically binds to membrane-bound human FAM19A5 with a $K_D$ of 10 nM or less as determined by ELISA, e.g., between 0.1 and 10 nM, between 0.1 and 5 nM, between 0.1 and 1 nM, between 0.5 and 10 nM, between 0.5 and 5 nM, between 0.5 and 1 nM, between 1 and 10 nM, between 1 and 5 nM, or between 5 and 10 nM. In some embodiments, the anti-FAM19A5 antibody or antigen binding portion thereof binds to membrane-bound human FAM19A5 with a $K_D$ of about 1 pM, 2 pM, 3 pM, 4 pM, 5 pM, 6 pM, 7 pM, 8 pM, 9 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, or 900 pM, or about 1 nM, 2 nM, 3 nM, 4 nM, 5 nM, 6 nM, 7 nM, 8 nM, or 9 nM, or about 10 nM, 20 nM, 30 nM, 40 nM, 50 nM, 60 nM, 70 nM, 80 nM, or 90 nM, as determined by as determined by ELISA.

An anti-FAM19A5 antibody or antigen binding portion thereof of the present disclosure can delay or inhibit an onset of gliosis, e.g., delay, slow down or suppress an onset or beginning of a nonspecific reactive change of glial cells in the central nervous system (CNS, e.g., brain and/or the spinal cord) in response to injury or damage from, e.g., trauma, cerebrospinal damage, brain tumor, infection, ischemia, stroke, autoimmune responses, and/or neurodegenerative disease.

An anti-FAM19A5 antibody or antigen binding portion thereof of the present disclosure can delay, inhibit, slowing down, suppress, curb, or prevent excessive or abnormal proliferation of reactive astrocytes and its associated detrimental effects of the CNS. For example, an anti-FAM19A5 antibody or antigen binding portion thereof of the present disclosure can inhibit or prevent abnormal increase in the number of astrocytes due to the destruction of neurons from e.g., CNS damage, trauma, injury, cerebrospinal damage, brain tumor, infection, ischemia, stroke, autoimmune responses, and/or neurodegenerative disease, inhibit or prevent scar formation in the CNS, inhibit or reduce the release of neurotoxic levels of reactive oxygen species or release of potentially excitotoxic glutamate, reduce or inhibit seizure, pain, and/or secondary degeneration after CNS injury. An anti-FAM19A5 antibody or antigen binding portion thereof of the present disclosure can promote, stimulate, increase, or activate regrowth of neurons and/or axon, preferably after CNS injury or damage.

An anti-FAM19A5 antibody or antigen binding portion thereof of the present disclosure can inhibit expression of chondroitin sulfate proteoglycans including proteoglycans composed of a protein core and a chondroitin sulfate (CSGPs), such as aggrecan (CSPG1), versican (CSPG2), neurocan (CSPG3), CSPG4 (or neuron-glial antigen 2 (NG2)), CSPG5, SMC3 (CSPG6, structural maintenance of chromosomes 3), brevican (CSPG7), and CD44 (CSPG8, cluster of differentiation 44), phosphacanneurocan (CSPG3). In some embodiments, the anti-FAM19A5 antibody or antigen binding portion thereof of the present disclosure inhibits, decreases or reduces the level of neurocan and/or NG2, or the activities of neurocan and/or NG2.

An anti-FAM19A5 antibody or antigen binding portion thereof of the present disclosure can increase expression of c-fos and pERK in the nucleus of neurons, e.g., increase the mRNA, protein, and/or protein activity of c-fos and pERK. An anti-FAM19A5 antibody or antigen binding portion thereof of the present disclosure can also increase or enhance the level of expression of GAP43 mPNA, GAP43 protein or increase or enhance the GAP43 protein activities.

In certain embodiments, the anti-FAM19A5 antibody or antigen binding portion thereof of the present disclosure thereof cross-competes for binding to (or inhibits binding of) a human FAM19A5 epitope with an anti-FAM19A5 antibody comprising CDRs or variable regions disclosed herein. In certain embodiments, anti-FAM19A5 antibodies or antigen binding portions thereof inhibit binding of a reference antibody comprising: a heavy chain CDR1, CDR2, and CDR3, and a light chain CDR1, CDR2, and CDR3, wherein (1) the heavy chain CDR1, CDR2, and CDR3 comprise the amino acid sequence of SEQ ID NO: 7, SEQ ID NO: 8, and SEQ ID NO: 9, respectively, and the light chain CDR1, CDR2, and CDR3 comprise the amino acid sequence of SEQ ID NO: 10, SEQ ID NO: 11, and SEQ ID NO: 12, respectively; (2) the heavy chain variable region CDR1, CDR2, and CDR3 comprises SEQ ID NOs: 29, 30, 31, respectively, and a light chain CDR1, CDR2, and CDR3 comprises SEQ ID NOs: 32, 33, 34, respectively; (3) the heavy chain variable region CDR1, CDR2, and CDR3 comprises SEQ ID NOs: 35, 36, 37, respectively, and a light chain CDR1, CDR2, and CDR3 comprises SEQ ID NOs: 38, 39, 40, respectively; (4) the heavy chain variable region CDR1, CDR2, and CDR3 comprises SEQ ID NOs: 41, 42, 43, respectively, and a light chain CDR1, CDR2, and CDR3 comprises SEQ ID NOs: 44, 45, 46, respectively; (5) the heavy chain variable region CDR1, CDR2, and CDR3 comprises SEQ ID NOs: 47, 48, 49, respectively, and a light chain CDR1, CDR2, and CDR3 comprises SEQ ID NOs: 50, 51, 52, respectively; (6) the heavy chain variable region CDR1, CDR2, and CDR3 comprises SEQ ID NOs: 53, 54, 55, respectively, and a light chain CDR1, CDR2, and CDR3 comprises SEQ ID NOs: 56, 57, 58, respectively; (7) the heavy chain variable region CDR1, CDR2, and CDR3 comprises SEQ ID NOs: 59, 60, 61, respectively, and a light chain CDR1, CDR2, and CDR3 comprises SEQ ID NOs: 62, 63, 64, respectively; (8) the heavy chain variable region CDR1, CDR2, and CDR3 comprises SEQ ID NOs: 65, 66, 67, respectively, and a light chain CDR1, CDR2, and CDR3 comprises SEQ ID NOs: 68, 69, 70, respectively; (9) the heavy chain variable region CDR1, CDR2, and CDR3 comprises SEQ ID NOs: 71, 72, 73, respectively, and a light chain CDR1, CDR2, and CDR3 comprises SEQ ID NOs: 74, 75, 76, respectively; (10) the heavy chain variable region CDR1, CDR2, and CDR3 comprises SEQ ID NOs: 77, 78, 79, respectively, and a light chain CDR1, CDR2, and CDR3 comprises SEQ ID NOs: 80, 81, 82, respectively; (11) the heavy chain variable region CDR1, CDR2, and CDR3 comprises SEQ ID NOs: 83, 84, 85, respectively, and a light chain CDR1, CDR2, and CDR3 comprises SEQ ID NOs: 86, 87, 88, respectively; or (12) the heavy chain variable region CDR1, CDR2, and CDR3 comprises SEQ ID NOs: 89, 90, 91, respectively, and a light chain CDR1, CDR2, and CDR3 comprises SEQ ID NOs: 92, 93, 94, respectively.

In some embodiments, the reference antibody comprises: (1) a heavy chain variable region (VH) comprising SEQ ID NO: 5 and a light chain variable region (VL) comprising SEQ ID NO: 6; (2) a heavy chain variable region (VH) comprising SEQ ID NO: 103 and a light chain variable region (VL) comprising SEQ ID NO: 114; (3) a heavy chain variable region (VH) comprising SEQ ID NO: 104 and a light chain variable region (VL) comprising SEQ ID NO: 115; (4) a heavy chain variable region (VH) comprising SEQ ID NO: 105 and a light chain variable region (VL) comprising SEQ ID NO: 116; (5) a heavy chain variable region (VH) comprising SEQ ID NO: 106 and a light chain variable region (VL) comprising SEQ ID NO: 117; (6) a heavy chain variable region (VH) comprising SEQ ID NO: 107 and a light chain variable region (VL) comprising SEQ ID NO: 118; (7) a heavy chain variable region (VH) comprising SEQ ID NO: 108 and a light chain variable region (VL) comprising SEQ ID NO: 119; (8) a heavy chain variable region (VH) comprising SEQ ID NO: 109 and a light chain variable region (VL) comprising SEQ ID NO: 120; (9) a heavy chain variable region (VH) comprising SEQ ID NO: 110 and a light chain variable region (VL) comprising SEQ ID NO: 121; (10) a heavy chain variable region (VH) comprising SEQ ID NO: 111 and a light chain variable region (VL) comprising SEQ ID NO: 122; (11) a heavy chain variable region (VH) comprising SEQ ID NO: 112 and a light chain variable region (VL) comprising SEQ ID NO: 123; or (12) a heavy chain variable region (VH) comprising SEQ ID NO: 113 and a light chain variable region (VL) comprising SEQ ID NO: 124.

In certain embodiments, the anti-FAM19A5 antibody or antigen binding portion thereof inhibits binding of such a reference antibody to human FAM19A5 by at least 10%, 20%, 30%, 40%, 50%, 60%, 70%, 80%, 90% or by 100%. Competing antibodies bind to the same epitope, an overlapping epitope or to adjacent epitopes (e.g., as evidenced by steric hindrance). Whether two antibodies compete with each other for binding to a target can be determined using competition experiments known in the art such as RIA and EIA.

In certain embodiments, the anti-FAM19A5 antibody or antigen binding portions thereof bind to the same FAM19A5 epitope as a reference antibody disclosed herein comprising a heavy chain CDR1, CDR2, and CDR3 and a light chain CDR1, CDR2, and CDR3, wherein: (1) the heavy chain CDR1, CDR2, and CDR3 comprise the amino acid sequence of SEQ ID NO: 7, SEQ ID NO: 8, and SEQ ID NO: 9, respectively, and light chain CDR1, CDR2, and CDR3 comprise the amino acid sequence of SEQ ID NO: 10, SEQ ID NO: 11, and SEQ ID NO: 12, respectively; (2) the heavy chain variable region CDR1, CDR2, and CDR3 comprises SEQ ID NOs: 29, 30, 31, respectively, and a light chain CDR1, CDR2, and CDR3 comprises SEQ ID NOs: 32, 33, 34, respectively; (3) the heavy chain variable region CDR1, CDR2, and CDR3 comprises SEQ ID NOs: 35, 36, 37, respectively, and a light chain CDR1, CDR2, and CDR3 comprises SEQ ID NOs: 38, 39, 40, respectively; (4) the heavy chain variable region CDR1, CDR2, and CDR3 comprises SEQ ID NOs: 41, 42, 43, respectively, and a light chain CDR1, CDR2, and CDR3 comprises SEQ ID NOs: 44, 45, 46, respectively; (5) the heavy chain variable region CDR1, CDR2, and CDR3 comprises SEQ ID NOs: 47, 48, 49, respectively, and a light chain CDR1, CDR2, and CDR3 comprises SEQ ID NOs: 50, 51, 52, respectively; (6) the heavy chain variable region CDR1, CDR2, and CDR3 comprises SEQ ID NOs: 53, 54, 55, respectively, and a light chain CDR1, CDR2, and CDR3 comprises SEQ ID NOs: 56, 57, 58, respectively; (7) the heavy chain variable region CDR1, CDR2, and CDR3 comprises SEQ ID NOs: 59, 60, 61, respectively, and a light chain CDR1, CDR2, and CDR3 comprises SEQ ID NOs: 62, 63, 64, respectively; (8) the heavy chain variable region CDR1, CDR2, and CDR3 comprises SEQ ID NOs: 65, 66, 67, respectively, and a light chain CDR1, CDR2, and CDR3 comprises SEQ ID NOs: 68, 69, 70, respectively; (9) the heavy chain variable region CDR1, CDR2, and CDR3 comprises SEQ ID NOs: 71, 72, 73, respectively, and a light chain CDR1, CDR2, and CDR3 comprises SEQ ID NOs: 74, 75, 76, respectively; (10) the heavy chain variable region CDR1, CDR2, and CDR3 comprises SEQ ID NOs: 77, 78, 79, respectively, and a light chain CDR1, CDR2, and CDR3 comprises SEQ ID NOs: 80, 81, 82, respectively; (11) the heavy chain variable region CDR1, CDR2, and CDR3 comprises SEQ ID NOs: 83, 84, 85, respectively, and a light chain CDR1, CDR2, and CDR3 comprises SEQ ID NOs: 86, 87, 88, respectively; or (12) the heavy chain variable region CDR1, CDR2, and CDR3 comprises SEQ ID NOs: 89, 90, 91, respectively, and a light chain CDR1, CDR2, and CDR3 comprises SEQ ID NOs: 92, 93, 94, respectively.

In some embodiments, the reference antibody comprises: (1) a heavy chain variable region (VH) comprising SEQ ID NO: 5 and a light chain variable region (VL) comprising SEQ ID NO: 6; (2) a heavy chain variable region (VH) comprising SEQ ID NO: 103 and a light chain variable region (VL) comprising SEQ ID NO: 114; (3) a heavy chain variable region (VH) comprising SEQ ID NO: 104 and a light chain variable region (VL) comprising SEQ ID NO: 115; (4) a heavy chain variable region (VH) comprising SEQ ID NO: 105 and a light chain variable region (VL) comprising SEQ ID NO: 116; (5) a heavy chain variable region (VH) comprising SEQ ID NO: 106 and a light chain variable region (VL) comprising SEQ ID NO: 117; (6) a heavy chain variable region (VH) comprising SEQ ID NO: 107 and a light chain variable region (VL) comprising SEQ ID NO: 118; (7) a heavy chain variable region (VH) comprising SEQ ID NO: 108 and a light chain variable region (VL) comprising SEQ ID NO: 119; (8) a heavy chain variable region (VH) comprising SEQ ID NO: 109 and a light chain variable region (VL) comprising SEQ ID NO: 120; (9) a heavy chain variable region (VH) comprising SEQ ID NO: 110 and a light chain variable region (VL) comprising SEQ ID NO: 121; (10) a heavy chain variable region (VH) comprising SEQ ID NO: 111 and a light chain variable region (VL) comprising SEQ ID NO: 122; (11) a heavy chain variable region (VH) comprising SEQ ID NO: 112 and a light chain variable region (VL) comprising SEQ ID NO: 123; or (12) a heavy chain variable region (VH) comprising SEQ ID NO: 113 and a light chain variable region (VL) comprising SEQ ID NO: 124.

Techniques for determining whether two antibodies bind to the same epitope include, e.g., epitope mapping methods, such as, x-ray analyses of crystals of antigen:antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

An anti-FAM19A5 antibody or antigen binding portion thereof of the present disclosure can bind to at least one epitope of mature human FAM19A5, as determined, e.g., by binding of the antibodies to fragments of human FAM19A5. In some embodiments, anti-FAM19A5 antibodies or antigen binding portions thereof bind to at least one epitope, which has the amino acid sequence of CDMLPCLEGEGCDLLINRSG (SEQ ID NO: 2, epitope F5, Example 10, amino acid residues 90 to 109 of SEQ ID NO: 4), or bind to a fragment located within the amino acid sequence of SEQ ID NO: 2, e.g., an epitope having at least 3, 4, 5, 6, 7, 8, 9, 10, 11, 12, 13, 14, 15, 16, 17, 18, 19, or 20 amino acids of SEQ ID NO: 2. In some embodiments, anti-FAM19A5 antibodies or antigen binding portion thereof bind to amino acid residues 99 to 107 (i.e., EGCDLLINR) of SEQ ID NO: 4. In certain embodiments, anti-FAM19A5 antibodies or antigen binding portion thereof bind to amino acid residues 99, 100, 102, 103, 105, and 107 (i.e., EG-DL-I-R) of SEQ ID NO: 4. In other embodiments, anti-FAM19A5 antibodies or antigen binding portion thereof bind to amino acid residues 102, 103, 105, and 107 (i.e., DL-I-R) of SEQ ID NO: 4. In some embodiments, anti-FAM19A5 antibodies or antigen binding portion thereof bind to 99, 100, and 107 (i.e., EG------R) of SEQ ID NO: 4. In some embodiments, the at least one epitope has the amino acid sequence that is at least 90%, at least about 95%, at least about 96%, at least about 97%, at least about 98%, at least about 99%, or about 100% identical to SEQ ID NO: 2. In some embodiments, the anti-FAM19A5 antibody or antigen binding portion thereof binds to a human FAM19A5 epitope only, which is SEQ ID NO: 2, or a fragment located within the amino acid sequence of SEQ ID NO: 2, e.g., an epitope having 3, 4, 5, 6, 7, 8, 9, 10, 11, 12, 13, 14, 15, 16, 17, 18, 19, or 20 amino acids of SEQ ID NO: 2. In some embodiments, the anti-FAM19A5 antibody or antigen binding portion thereof of the present disclosure binds to SEQ ID NO: 2 or a fragment thereof in its native conformation (i.e., un-denatured). In some embodiments, the anti-FAM19A5 antibody or antigen binding portion thereof binds to both glycosylated and unglycosylated human FAM19A5.

In some embodiments, the anti-FAM19A5 antibody or antigen binding portion thereof further binds to one or more additional FAM19A5 epitopes. Therefore, certain anti-FAM19A5 antibodies or antigen binding portions thereof bind to an epitope of SEQ ID NO: 2 and an additional epitope. In some embodiments, the one or more additional FAM19A5 epitopes are selected from QFLKEGQLAAGT-CEIVTLDR (SEQ ID NO: 13, epitope F1), TLDRDSSQPRRTIARQTARC (SEQ ID NO: 14, epitope F2), TARCACRKGQIAGTTRARPA (SEQ ID NO: 15, epitope F3), ARPACVDARIIKTKQWCDML (SEQ ID NO: 16, epitope F4), or NRSGWTCTQPGGRIKTTTVS (SEQ ID NO: 17, epitope F6), or a fragment located within the amino acid sequence of SEQ ID NO: 13, SEQ ID NO: 14, SEQ ID NO: 15, SEQ ID NO: 16, or SEQ ID NO: 17, or any combination thereof. A fragment located within the amino acid sequence of SEQ ID NO: 13, SEQ ID NO: 14, SEQ ID NO: 15, SEQ ID NO: 16, or SEQ ID NO: 17, includes a fragment having 1, 2, 3, 4, 5, 6, 7, 8, 9, 10, 11, 12, 13, 14, 15, 16, 17, 18, 19, or 20 amino acids of any of SEQ ID NO: 13, SEQ ID NO: 14, or SEQ ID NO: 15, SEQ ID NO: 16, and SEQ ID NO: 17. In some embodiments, the one or more additional FAM19A5 epitopes are selected from SEQ ID NO: 14, SEQ ID NO: 15, a fragment located within the amino acid sequence of SEQ ID NO: 14, SEQ ID NO: 15, e.g., a fragment having 1, 2, 3, 4, 5, 6, 7, 8, 9, 10, 11, 12, 13, 14, 15, 16, 17, 18, 19, or 20 amino acids of SEQ ID NO: 14 or SEQ ID NO: 15, or any combination thereof. In some embodiments, the anti-FAM19A5 antibody or antigen binding portion thereof of the disclosure binds to any of the one or more additional epitopes in their native conformation (i.e., un-denatured). In some embodiments, the anti-FAM19A5 antibody or antigen binding portion thereof binds to both glycosylated and unglycosylated of the one or more additional FAM19A5 epitopes.

In some embodiments, the anti-FAM19A5 antibody, or antigen binding portion thereof, binds to at least one FAM19A5 epitope identified as EP6, EP7, or EP8, wherein EP6 comprises the amino acids KTKQWCDML (SEQ ID NO: 139), wherein EP7 comprises the amino acids GCDLLINR (SEQ ID NO: 140, and wherein EP8 comprises the amino acids TCTQPGGR (SEQ ID NO: 141). In some embodiments, the at least one epitope has the amino acid sequence that is at least 90%, at least about 95%, at least about 96%, at least about 97%, at least about 98%, at least about 99%, or about 100% identical to EP6, EP7, or EP8. In some embodiments, the anti-FAM19A5 antibody, or antigen binding portion thereof, only binds to EP6, EP7, or EP8. In some embodiments, the anti-FAM19A5 antibody, or antigen binding portion thereof, binds to EP6, EP7, and EP8. In some embodiments, the anti-FAM19A5 antibody, or antigen binding portion thereof, binds to EP7 and EP8. In some embodiments, the anti-FAM19A5 antibody, or antigen binding portion thereof, binds to EP7.

In certain embodiments, provided herein is an antibody or antigen binding portion thereof that binds to FAM19A5 (e.g., human FAM19A5) with a 20%, 25%, 30%, 35%, 40%, 45%, 50%, 55%, 60%, 65%, 70%, 75%, 80%, 85%, 90%, 95% or higher affinity than to another protein in the FAM19A family as measured by, e.g., a immunoassay (e.g., ELISA), surface plasmon resonance, or kinetic exclusion assay. In a specific embodiment, provided herein is an antibody or antigen binding portion thereof that binds to FAM19A5 (e.g., human FAM19A5) with no cross reactivity with another protein in the FAM19A family as measured by, e.g., a immunoassay.

In certain embodiments, the anti-FAM19A5 antibodies are not native antibodies or are not naturally-occurring antibodies. For example, the anti-FAM19A5 antibodies have post-translational modifications that are different from those of antibodies that are naturally occurring, such as by having more, less or a different type of post-translational modification.

III. Exemplary Anti-FAM19A5 Antibodies

Particular antibodies described herein are antibodies, e.g., monoclonal antibodies, having the CDR and/or variable region sequences of antibody 1-65, P2-C12, 13B4, 13F7, 15A9, P1-A03, P1-A08, P1-F02, P2-A01, P2-A03, P2-F07, or P2-F11, as well as antibodies having at least 80% identity (e.g., at least 85%, at least 90%, at least 95%, or at least 99% identity) to their variable region or CDR sequences. The VH and VL amino acid sequences of the anti-FAM19A5 antibodies of the present disclosure are provided in Tables 2 and 3, respectively.

TABLE 2

| Variable heavy chain CDR amino acid sequences | | | |
|---|---|---|---|
| Antibody | VH-CDR1 | VH-CDR2 | VH-CDR3 |
| Anti-FAM19A5 ("1-65") | SYQMG (SEQ ID NO: 7) | VINKSGSDTS (SEQ ID NO: 8) | GSASYITAATIDA (SEQ ID NO: 9) |
| Anti-FAM19A5 ("P2-C12") | TYAVT (SEQ ID NO: 29) | YINWRGGTSYANWAKG (SEQ ID NO: 30) | DASSGAAFGSYGMDP (SEQ ID NO: 31) |
| Anti-FAM19A5 ("13B4") | SSNWWS (SEQ ID NO: 35) | EIYHGGTTNYNPSLKG (SEQ ID NO: 36) | WQLVGGLDV (SEQ ID NO: 37) |

TABLE 2-continued

Variable heavy chain CDR amino acid sequences

| Antibody | VH-CDR1 | VH-CDR2 | VH-CDR3 |
| --- | --- | --- | --- |
| Anti-FAM19A5 ("13F7") | GYSWT (SEQ ID NO: 41) | EISHFGSANYNPSLKS (SEQ ID NO: 42) | ALRGTYSRFYYGMDV (SEQ ID NO: 43) |
| Anti-FAM19A5 ("15A9") | SYYWS (SEQ ID NO: 47) | YIYPSGSTNYNPSLKS (SEQ ID NO: 48) | VNPFGYYYAMDV (SEQ ID NO: 49) |
| Anti-FAM19A5 ("P1-A03") | SDYMS (SEQ ID NO: 53) | IIYPSTTTYYASWAKG (SEQ ID NO: 54) | GSNWSSGMNL (SEQ ID NO: 55) |
| Anti-FAM19A5 ("P1-A08") | TYYMS (SEQ ID NO: 59) | IVYPSGTTYYANWAKG (SEQ ID NO: 60) | GDSFGYGL (SEQ ID NO: 61) |
| Anti-FAM19A5 ("P1-F02") | NYYMG (SEQ ID NO: 65) | IIYASGSTYYASWAKG (SEQ ID NO: 66) | IDIGVGDYGWAYDRLDL (SEQ ID NO: 67) |
| Anti-FAM19A5 ("P2-A01") | GYYMS (SEQ ID NO: 71) | IIYPSGSTDYASWAKG (SEQ ID NO: 72) | VAGYVGYGYETFFDI (SEQ ID NO: 73) |
| Anti-FAM19A5 ("P2-A03") | NYDMS (SEQ ID NO: 77) | FMDTDGSAYYATWAKG (SEQ ID NO: 78) | RGSSYYGGIDI (SEQ ID NO: 79) |
| Anti-FAM19A5 ("P2-F07") | SYYMN (SEQ ID NO: 83) | IIYPSGTTYYAGWAKG (SEQ ID NO: 84) | TVSGYFDI (SEQ ID NO: 85) |
| Anti-FAM19A5 ("P2-F11") | SYGVS (SEQ ID NO: 89) | YIANNYNPHYASWAKG (SEQ ID NO: 90) | DNYGMDP (SEQ ID NO: 91) |

TABLE 3

Variable light chain CDR amino acid sequences

| Antibody | VL-CDR1 | VL-CDR2 | VL-CDR3 |
| --- | --- | --- | --- |
| Anti-FAM19A5 ("1-65") | SGGGSSGYGYG (SEQ ID NO: 10) | WNDKRPS (SEQ ID NO: 11) | GNDDYSSDSGYVGV (SEQ ID NO: 12) |
| Anti-FAM19A5 ("P2-C12") | QASQSISSYLS (SEQ ID NO: 32) | EASKLAS (SEQ ID NO: 33) | QQGYSSTNVWNA (SEQ ID NO: 34) |
| Anti-FAM19A5 ("13B4") | SGDKLGNVYAS (SEQ ID NO: 38) | QDNKRPS (SEQ ID NO: 39) | QAWDSSTAV (SEQ ID NO: 40) |
| Anti-FAM19A5 ("13F7") | RSSQSLLHSNGYNYLD (SEQ ID NO: 44) | LGSNRAS (SEQ ID NO: 45) | MQARQTPLT (SEQ ID NO: 46) |
| Anti-FAM19A5 ("15A9") | RASQSISTSLN (SEQ ID NO: 50) | GASTLQS (SEQ ID NO: 51) | QESASIPRT (SEQ ID NO: 52) |
| Anti-FAM19A5 ("P1-A03") | LASEDIYSGIS (SEQ ID NO: 56) | GASNLES (SEQ ID NO: 57) | LGGYSYSSTGLT (SEQ ID NO: 58) |
| Anti-FAM19A5 ("P1-A08") | TADTLSRSYAS (SEQ ID NO: 62) | RDTSRPS (SEQ ID NO: 63) | ATSDGSGSNYQYV (SEQ ID NO: 64) |
| Anti-FAM19A5 ("P1-F02") | LASEDIYSGIS (SEQ ID NO: 68) | GASNLES (SEQ ID NO: 69) | LGGYSYSSIT (SEQ ID NO: 70) |
| Anti-FAM19A5 ("P2-A01") | LASEDIYSGIS (SEQ ID NO: 74) | GASNLES (SEQ ID NO: 75) | LGGVTYSSTGTHLT (SEQ ID NO: 76) |
| Anti-FAM19A5 ("P2-A03") | QASQSIGGNLA (SEQ ID NO: 80) | RASTLAS (SEQ ID NO: 81) | QSPAYDPAAYVGNA (SEQ ID NO: 82) |
| Anti-FAM19A5 ("P2-F07") | LASEDIYSALA (SEQ ID NO: 86) | GTSNLES (SEQ ID NO: 87) | QGYSSYPLT (SEQ ID NO: 88) |
| Anti-FAM19A5 ("P2-F11") | QASQSVYNNKNLA (SEQ ID NO: 92) | AASTLAS (SEQ ID NO: 93) | QGEFSCSSADCNA (SEQ ID NO: 94) |

TABLE 4

Variable heavy chain amino acid sequence

| Antibody | VH Amino Acid Sequence (SEQ ID NO) |
|---|---|
| Anti-FAM19A5 ("1-65") | AVTLDESGGGLQTPGGALSLVCKASGFTFSSYQMGWVRQAPGKGLEWVGVINKSGSDTSY GSAVKGRATISRDNGQSTVRLQLNNLRAEDTGTYFCAKGSASYITAATIDAWGHGTEVIV SS (SEQ ID NO: 5) |
| Anti-FAM19A5 ("P2-C12") | QSLEESGGRLVTPGTPLTLTCTVSGFSLSTYAVTWVRQAPGKGLEWIGYINWRGGTSYAN WAKGRFTISKTSSTTVDLKMTSPTTEDTATYFCARDASSGAAFGSYGMDPWGPGTLVTVS S (SEQ ID NO: 103) |
| Anti-FAM19A5 ("13B4") | QVQLQESGPGLVKPSGTLSLNCAVSGGSISSSNWWSWVRQPPGKGLEWIGEIYHGGTTNY NPSLKGRVTMSVDKTKNQFSLRLSSVTAVDTAVYYCARWQLVGGLDVWGQGTTVTVSS (SEQ ID NO: 104) |
| Anti-FAM19A5 ("13F7") | QVQLQEWGAGLLKPSETLSLTCAINAESFNGYSWTWIRQTPGKGLEWIGEISHFGSANYN PSLKSRATISADKSKNQFSLKLTSVTAVDTAVYYCARALRGTYSRFYYGMDVWGQGTTVT VSS (SEQ ID NO: 105) |
| Anti-FAM19A5 ("15A9") | QVQLQESGPGLVKPSETLSLTCTVSGGSISSYYWSWIRQPPGKGLEWIGYIYPSGSTNYN PSLKSRVTISVDTSKNQFSLNLKSVTAVDTAVYYCARVNPFGYYYAMDVWGQGTTVTVSS (SEQ ID NO: 106) |
| Anti-FAM19A5 ("P1-A03") | QSVEESGGRLVTPGTPLTLTCTVSGFSLSSDYMSWVRQAPGEGLEWIGIIYPSTTTYYAS WAKGRFTISKTSSTTVELKMTSLTTEDTATYFCARGSNWSSGMNLWGPGTLVTVSS (SEQ ID NO: 107) |
| Anti-FAM19A5 ("P1-A08") | QSLEESGGRLVTPGTPLTLTCTASGFSLSTYYMSWVRQAPGKGLEWIGIVYPSGTTYYAN WAKGRFTISTASTTVDLMITSPTTEDTATYFCARGDSFGYGLWGPGTLVTVSS (SEQ ID NO: 108) |
| Anti-FAM19A5 ("P1-F02") | QSLEESGGRLVTPGTPLTLTCTASGFSLSNYYMGWVRQAPGEGLEWIGIIYASGSTYYAS WAKGRFTISKTSTTVDLKMTSLTTEDTATYFCARIDIGVGDYGWAYDRLDLWGQGTLVTV SS (SEQ ID NO: 109) |
| Anti-FAM19A5 ("P2-A01") | QEQLVESGGRLVTPGTPLTLSCTASGFFLSGYYMSWVRQAPGKGLEWIGIIYPSGSTDYA SWAKGRFTISKTSTTVDLKITTPTTEDTATYFCARVAGYVGYGYETFFDIWGPGTLVTVS L (SEQ ID NO: 110) |
| Anti-FAM19A5 ("P2-A03") | QSVEESGGRLVTPGTPLTLTCTVSGFSLNNYDMSWVRQAPGKGLEYIGFMDTDGSAYYAT WAKGRFTISRTSTTVDLKMTSPTTEDTATYFCARRGSSYYGGIDIWGPGTPVTVSL (SEQ ID NO: 111) |
| Anti-FAM19A5 ("P2-F07") | QSLEESGGRLVTPGTPLTLTCTASGFSLSSYYMNWVRQAPGKGLEWIGIIYPSGTTYYAG WAKGRFTISKTSTTVDLKITSPTSEDTATYFCARTVSGYFDIWGPGTLVTVSL (SEQ ID NO: 112) |
| Anti-FAM19A5 ("P2-F11") | QEQLVESGGRLVTPGTTLTLTCTVSGFSLSSYGVSWVRQAPGKGLEWIGYIANNYNPHYA SWAKGRFTISKTSSTTVDLKMTSLTTEDTATYFCARDNYGMDPWGPGTLVTVSS (SEQ ID NO: 113) |

TABLE 5

Variable light chain amino acid sequence

| Antibody | VL Amino Acid Sequence (SEQ ID NO) |
|---|---|
| Anti-FAM19A5 ("1-65") | ALTQPSSVSANPGETVKITCSGGGSSGYGYGWYQQKSPSSAPLTVIYWNDKRPSDIPSRF SGSKSGSTHTLTITGVQAEDEAVYFCGNDDYSSDSGYVGVFGAGTTLTVL (SEQ ID NO: 6) |
| Anti-FAM19A5 ("P2-C12") | ELDMTQTPSSVSAAVGGTVTIKCQASQSISSYLSWYQQKPGQPPKLLIYEASKLASGVPS RFSGSGYGTEFTLTISDLECADAATYYCQQGYSSTNVWNAFGGGTNVEIK (SEQ ID NO: 114) |
| Anti-FAM19A5 ("13B4") | SYELTQPLSVSVSPGQTASITCSGDKLGNVYASWYQQKPGQSPTLVIYQDNKRPSGIPER FSGSNSGKTATLTISGTQALDEADYYCQAWDSSTAVFGGGTKLTVL (SEQ ID NO: 115) |
| Anti-FAM19A5 ("13F7") | DIVMTQTPLSLPVAPGEPASISCRSSQSLLHSNGYNYLDWYVQKPGQPPQLLIYLGSNRA SGVPDRFSGSGSGTDFTLKISRVEAEDVGVYYCMQARQTPLTFGGGTKVEIK (SEQ ID NO: 116) |

TABLE 5-continued

Variable light chain amino acid sequence

| Antibody | VL Amino Acid Sequence (SEQ ID NO) |
|---|---|
| Anti-FAM19A5 ("15A9") | DIQMTQSPSSLSASVGDRITISCRASQSISTSLNWYQQTPGKAPRLLIYGASTLQSGVPS RFSGGGSGTDFSLTITSLQPEDFATYYCQESASIPRTFGQGTKLDIK (SEQ ID NO: 117) |
| Anti-FAM19A5 ("P1-A03") | ELVMTQTPPSLSASVGETVRIRCLASEDIYSGISWYQQKPEKPPTLLISGASNLESGVPP RFSGSGSGTDYTLTIGGVQAEDAATYYCLGGYSYSSTGLTFGAGTNVEIK (SEQ ID NO: 118) |
| Anti-FAM19A5 ("P1-A08") | ELVLTQSPSVQVNLGQTVSLTCTADTLSRSYASWYQQKPGQAPVLLIYRDTSRPSGVPDR FSGSSSGNTATLTISGAQAGDEADYYCATSDGSGSNYQYVFGGGTQLTVT (SEQ ID NO: 119) |
| Anti-FAM19A5 ("P1-F02") | ELDMTQTPPSLSASVGETVRIRCLASEDIYSGISWYQQKPGKPPTLLIYGASNLESGVPP RFSGSGSGTDYTLTIGGVQAEDAATYYCLGGYSYSSITFGAGTNVEIK (SEQ ID NO: 120) |
| Anti-FAM19A5 ("P2-A01") | ELVMTQTPPSLSASVGETVRIRCLASEDIYSGISWYQQKPGKPPTLLIYGASNLESGVPP RFSGSGSGSDYTLTIGGVQAEDAATYYCLGGVTYSSTGTHLTFGAGTNVEIK (SEQ ID NO: 121) |
| Anti-FAM19A5 ("P2-A03") | ELDLTQTPASVSEPVGGTVTIKCQASQSIGGNLAWYQQKPGQPPKLLIYRASTLASGVPS RFKGSGSGTDFTLTISDLECADAATYYCQSPAYDPAAYVGNAFGGGTELEIL (SEQ ID NO: 122) |
| Anti-FAM19A5 ("P2-F07") | ELDLTQTPPSLSASVGGTVTINCLASEDIYSALAWYQQKPGKPPTLLISGTSNLESGVPP RFSGSGSGTDYTLTIGGVQAEDAATYFCQGYSSYPLTFGAGTNVEIK (SEQ ID NO: 123) |
| Anti-FAM19A5 ("P2-F11") | ELDLTQTPSSVSAAVGGTVTINCQASQSVYNNKNLAWYQQKPGQPPKLLIYAASTLASGV SSRFKGSGSGTQFTLTISDVQCDDAATYYCQGEFSCSSADCNAFGGGTELEIL (SEQ ID NO: 124) |

Accordingly, provided herein is an isolated anti-FAM19A5 antibody, or an antigen binding portion thereof, comprising heavy and light chain variable regions, wherein the heavy chain variable region comprises the amino acid sequence of SEQ ID NOs: 5 or 103-113. In other embodiments, the isolated anti-FAM19A5 antibody, or an antigen binding portion thereof, comprises the CDRs of the heavy chain variable region selected from the group consisting of SEQ ID NOs: 5 or 103-113.

Also provided is an isolated anti-FAM19A5 antibody, or an antigen binding portion thereof, comprising heavy and light chain variable regions, wherein the light chain variable region comprises the amino acid sequence of SEQ ID NOs: 6 or 114-124. In other embodiments, the isolated anti-FAM19A5 antibody, or an antigen binding portion thereof, comprises the CDRs of the light chain variable region selected from the group consisting of SEQ ID NOs: 6 or 114-124.

In certain embodiments, the isolated anti-FAM19A5 antibody, or an antigen binding portion thereof, comprises the CDRs of the heavy chain variable region selected from the group consisting of SEQ ID NOs: 5 or 103-113 and the CDRs of the light chain variable region selected from the group consisting of SEQ ID NOs: 6 or 114-124.

Also provided is an isolated anti-FAM19A5 antibody, or an antigen binding portion thereof, comprising heavy and light chain variable regions, (i) wherein the heavy chain variable region comprises the amino acid sequence of SEQ ID NO: 5 and wherein the light chain variable region comprises the amino acid sequence of SEQ ID NO: 6; (ii) wherein the heavy chain variable region comprises the amino acid sequence of SEQ ID NO: 103 and wherein the light chain variable region comprises the amino acid sequence of SEQ ID NO: 114; (iii) wherein the heavy chain variable region comprises the amino acid sequence of SEQ ID NO: 104 and wherein the light chain variable region comprises the amino acid sequence of SEQ ID NO: 115; (iv) wherein the heavy chain variable region comprises the amino acid sequence of SEQ ID NO: 105 and wherein the light chain variable region comprises the amino acid sequence of SEQ ID NO: 116; (v) wherein the heavy chain variable region comprises the amino acid sequence of SEQ ID NO: 106 and wherein the light chain variable region comprises the amino acid sequence of SEQ ID NO: 117; (vi) wherein the heavy chain variable region comprises the amino acid sequence of SEQ ID NO: 107 and wherein the light chain variable region comprises the amino acid sequence of SEQ ID NO: 118; (vii) wherein the heavy chain variable region comprises the amino acid sequence of SEQ ID NO: 108 and wherein the light chain variable region comprises the amino acid sequence of SEQ ID NO: 119; (viii) wherein the heavy chain variable region comprises the amino acid sequence of SEQ ID NO: 109 and wherein the light chain variable region comprises the amino acid sequence of SEQ ID NO: 120; (ix) wherein the heavy chain variable region comprises the amino acid sequence of SEQ ID NO: 110 and wherein the light chain variable region comprises the amino acid sequence of SEQ ID NO: 121; (x) wherein the heavy chain variable region comprises the amino acid sequence of SEQ ID NO: 111 and wherein the light chain variable region comprises the amino acid sequence of SEQ ID NO: 122; (xi) wherein the heavy chain variable region comprises the amino acid sequence of SEQ ID NO: 112 and wherein the light chain variable region comprises the amino acid sequence of SEQ ID NO: 123; and (xii) wherein the heavy chain variable region comprises the amino acid sequence of SEQ ID NO: 113 and wherein the light chain variable region comprises the amino acid sequence of SEQ ID NO: 124.

Provided herein is an isolated anti-FAM19A5 antibody, or an antigen-binding portion thereof, comprising a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 5 or 103-113.

Also provided herein is an isolated anti-FAM19A5 antibody, or an antigen-binding portion thereof, comprising a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 6 or 114-124.

Also provided is an isolated anti-FAM19A5 antibody, or an antigen binding portion thereof, comprising heavy and light chain variable regions, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 5 or 103-113, and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 6 or 114-124.

In some embodiments, the disclosure provides an isolated anti-FAM19A5 antibody, or an antigen-binding portion thereof, comprising:
(a) heavy and light chain variable region sequences comprising SEQ ID NOs: 5 and 6, respectively;
(b) heavy and light chain variable region sequences comprising SEQ ID NOs: 103 and 114, respectively;
(c) heavy and light chain variable region sequences comprising SEQ ID NOs: 104 and 115, respectively;
(d) heavy and light chain variable region sequences comprising SEQ ID NOs: 105 and 116, respectively;
(e) heavy and light chain variable region sequences comprising SEQ ID NOs: 106 and 117, respectively;
(f) heavy and light chain variable region sequences comprising SEQ ID NOs: 107 and 118, respectively;
(g) heavy and light chain variable region sequences comprising SEQ ID NOs: 108 and 119, respectively;
(h) heavy and light chain variable region sequences comprising SEQ ID NOs: 109 and 120, respectively;
(i) heavy and light chain variable region sequences comprising SEQ ID NOs: 110 and 121, respectively;
(j) heavy and light chain variable region sequences comprising SEQ ID NOs: 111 and 122, respectively;
(k) heavy and light chain variable region sequences comprising SEQ ID NOs: 112 and 123, respectively; or
(l) heavy and light chain variable region sequences comprising SEQ ID NOs: 113 and 124, respectively.

In certain embodiments, the anti-FAM19A5 antibody or antigen-binding portion thereof of the present disclosure comprises (i) the heavy chain CDR1, CDR2, and CDR3 of 1-65, or combinations thereof, and/or the light chain CDR1, CDR2, and CDR3 of 1-65, or any combinations thereof; (ii) the heavy chain CDR1, CDR2, and CDR3 of P2-C12, or combinations thereof, and/or the light chain CDR1, CDR2, and CDR3 of P2-C12, or any combinations thereof; (iii) the heavy chain CDR1, CDR2, and CDR3 of 13B4, or combinations thereof, and/or the light chain CDR1, CDR2, and CDR3 of 13B4, or any combinations thereof; (iv) the heavy chain CDR1, CDR2, and CDR3 of 13F7, or combinations thereof, and/or the light chain CDR1, CDR2, and CDR3 of 13F7, or any combinations thereof; (v) the heavy chain CDR1, CDR2, and CDR3 of 15A9, or combinations thereof, and/or the light chain CDR1, CDR2, and CDR3 of 15A9, or any combinations thereof; (vi) the heavy chain CDR1, CDR2, and CDR3 of P1-A03, or combinations thereof, and/or the light chain CDR1, CDR2, and CDR3 of P1-A03, or any combinations thereof; (vii) the heavy chain CDR1, CDR2, and CDR3 of P1-A08, or combinations thereof, and/or the light chain CDR1, CDR2, and CDR3 of P1-A08, or any combinations thereof; (viii) the heavy chain CDR1, CDR2, and CDR3 of P1-F02, or combinations thereof, and/or the light chain CDR1, CDR2, and CDR3 of P1-F02, or any combinations thereof; (ix) the heavy chain CDR1, CDR2, and CDR3 of P2-A01, or combinations thereof, and/or the light chain CDR1, CDR2, and CDR3 of P2-A01, or any combinations thereof; (x) the heavy chain CDR1, CDR2, and CDR3 of P2-A03, or combinations thereof, and/or the light chain CDR1, CDR2, and CDR3 of P2-A03, or any combinations thereof; (xi) the heavy chain CDR1, CDR2, and CDR3 of P2-F07, or combinations thereof, and/or the light chain CDR1, CDR2, and CDR3 of P2-F07, or any combinations thereof; or (xii) the heavy chain CDR1, CDR2, and CDR3 of P2-F11, or combinations thereof, and/or the light chain CDR1, CDR2, and CDR3 of F2-F11, or any combinations thereof. The amino acid sequences of the VH CDR1, CDR2, and CDR3 for the different anti-FAM19A5 antibodies disclosed herein are provided in Table 2. The amino acid sequences of the VL CDR1, CDR2, and CDR3 for the different anti-FAM19A5 antibodies disclosed herein are provided in Table 3.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 7; and/or
(b) a VH CDR2 comprising the amino acid sequence of SEQ ID NO: 8; and/or
(c) a VH CDR3 comprising the amino acid sequence of SEQ ID NO: 9.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 10; and/or
(b) a VL CDR2 comprising the amino acid sequence of SEQ ID NO: 11; and/or
(c) a VL CDR3 comprising the amino acid sequence of SEQ ID NO: 12.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 7;
(b) a VH CDR2 comprising the amino acid sequence of SEQ ID NO: 8;

(c) a VH CDR3 comprising the amino acid sequence of SEQ ID NO: 9;
(d) a VL CDR1 comprising the amino acid sequence of SEQ ID NO: 10;
(e) a VL CDR2 comprising the amino acid sequence of SEQ ID NO: 11; and/or
(f) a VL CDR3 comprising the amino acid sequence of SEQ ID NO: 12.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 29; and/or
(b) a VH CDR2 comprising the amino acid sequence of SEQ ID NO: 30; and/or
(c) a VH CDR3 comprising the amino acid sequence of SEQ ID NO: 31.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 32; and/or
(b) a VL CDR2 comprising the amino acid sequence of SEQ ID NO: 33; and/or
(c) a VL CDR3 comprising the amino acid sequence of SEQ ID NO: 34.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 29;
(b) a VH CDR2 comprising the amino acid sequence of SEQ ID NO: 30;
(c) a VH CDR3 comprising the amino acid sequence of SEQ ID NO: 31;
(d) a VL CDR1 comprising the amino acid sequence of SEQ ID NO: 32;
(e) a VL CDR2 comprising the amino acid sequence of SEQ ID NO: 33; and/or
(f) a VL CDR3 comprising the amino acid sequence of SEQ ID NO: 34.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 35; and/or
(b) a VH CDR2 comprising the amino acid sequence of SEQ ID NO: 36; and/or
(c) a VH CDR3 comprising the amino acid sequence of SEQ ID NO: 37.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 38; and/or
(b) a VL CDR2 comprising the amino acid sequence of SEQ ID NO: 39; and/or
(c) a VL CDR3 comprising the amino acid sequence of SEQ ID NO: 40.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 35;
(b) a VH CDR2 comprising the amino acid sequence of SEQ ID NO: 36;
(c) a VH CDR3 comprising the amino acid sequence of SEQ ID NO: 37;
(d) a VL CDR1 comprising the amino acid sequence of SEQ ID NO: 38;
(e) a VL CDR2 comprising the amino acid sequence of SEQ ID NO: 39; and/or
(f) a VL CDR3 comprising the amino acid sequence of SEQ ID NO: 40.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 41; and/or
(b) a VH CDR2 comprising the amino acid sequence of SEQ ID NO: 42; and/or
(c) a VH CDR3 comprising the amino acid sequence of SEQ ID NO: 43.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 44; and/or
(b) a VL CDR2 comprising the amino acid sequence of SEQ ID NO: 45; and/or
(c) a VL CDR3 comprising the amino acid sequence of SEQ ID NO: 46.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 41;
(b) a VH CDR2 comprising the amino acid sequence of SEQ ID NO: 42;
(c) a VH CDR3 comprising the amino acid sequence of SEQ ID NO: 43;
(d) a VL CDR1 comprising the amino acid sequence of SEQ ID NO: 44;
(e) a VL CDR2 comprising the amino acid sequence of SEQ ID NO: 45; and/or
(f) a VL CDR3 comprising the amino acid sequence of SEQ ID NO: 46.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 47; and/or
(b) a VH CDR2 comprising the amino acid sequence of SEQ ID NO: 48; and/or (c) a VH CDR3 comprising the amino acid sequence of SEQ ID NO: 49.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 50; and/or
(b) a VL CDR2 comprising the amino acid sequence of SEQ ID NO: 51; and/or
(c) a VL CDR3 comprising the amino acid sequence of SEQ ID NO: 52.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 47;
(b) a VH CDR2 comprising the amino acid sequence of SEQ ID NO: 48;
(c) a VH CDR3 comprising the amino acid sequence of SEQ ID NO: 49;
(d) a VL CDR1 comprising the amino acid sequence of SEQ ID NO: 50;
(e) a VL CDR2 comprising the amino acid sequence of SEQ ID NO: 51; and/or
(f) a VL CDR3 comprising the amino acid sequence of SEQ ID NO: 52.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 53; and/or
(b) a VH CDR2 comprising the amino acid sequence of SEQ ID NO: 54; and/or
(c) a VH CDR3 comprising the amino acid sequence of SEQ ID NO: 55.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 56; and/or
(b) a VL CDR2 comprising the amino acid sequence of SEQ ID NO: 57; and/or
(c) a VL CDR3 comprising the amino acid sequence of SEQ ID NO: 58.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 53;
(b) a VH CDR2 comprising the amino acid sequence of SEQ ID NO: 54;
(c) a VH CDR3 comprising the amino acid sequence of SEQ ID NO: 55;
(d) a VL CDR1 comprising the amino acid sequence of SEQ ID NO: 56;
(e) a VL CDR2 comprising the amino acid sequence of SEQ ID NO: 57; and/or
(f) a VL CDR3 comprising the amino acid sequence of SEQ ID NO: 58.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 59; and/or
(b) a VH CDR2 comprising the amino acid sequence of SEQ ID NO: 60; and/or
(c) a VH CDR3 comprising the amino acid sequence of SEQ ID NO: 61.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 62; and/or
(b) a VL CDR2 comprising the amino acid sequence of SEQ ID NO: 63; and/or
(c) a VL CDR3 comprising the amino acid sequence of SEQ ID NO: 64.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 59;
(b) a VH CDR2 comprising the amino acid sequence of SEQ ID NO: 60;
(c) a VH CDR3 comprising the amino acid sequence of SEQ ID NO: 61;
(d) a VL CDR1 comprising the amino acid sequence of SEQ ID NO: 62;
(e) a VL CDR2 comprising the amino acid sequence of SEQ ID NO: 63; and/or
(f) a VL CDR3 comprising the amino acid sequence of SEQ ID NO: 64.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 65; and/or
(b) a VH CDR2 comprising the amino acid sequence of SEQ ID NO: 66; and/or
(c) a VH CDR3 comprising the amino acid sequence of SEQ ID NO: 67.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 68; and/or
(b) a VL CDR2 comprising the amino acid sequence of SEQ ID NO: 69; and/or
(c) a VL CDR3 comprising the amino acid sequence of SEQ ID NO: 70.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 65;
(b) a VH CDR2 comprising the amino acid sequence of SEQ ID NO: 66;
(c) a VH CDR3 comprising the amino acid sequence of SEQ ID NO: 67;
(d) a VL CDR1 comprising the amino acid sequence of SEQ ID NO: 68;
(e) a VL CDR2 comprising the amino acid sequence of SEQ ID NO: 69; and/or
(f) a VL CDR3 comprising the amino acid sequence of SEQ ID NO: 70.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 71; and/or
(b) a VH CDR2 comprising the amino acid sequence of SEQ ID NO: 72; and/or
(c) a VH CDR3 comprising the amino acid sequence of SEQ ID NO: 73.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 74; and/or
(b) a VL CDR2 comprising the amino acid sequence of SEQ ID NO: 75; and/or
(c) a VL CDR3 comprising the amino acid sequence of SEQ ID NO: 76.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 71;
(b) a VH CDR2 comprising the amino acid sequence of SEQ ID NO: 72;
(c) a VH CDR3 comprising the amino acid sequence of SEQ ID NO: 73;
(d) a VL CDR1 comprising the amino acid sequence of SEQ ID NO: 74;
(e) a VL CDR2 comprising the amino acid sequence of SEQ ID NO: 75; and/or
(f) a VL CDR3 comprising the amino acid sequence of SEQ ID NO: 76.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 77; and/or
(b) a VH CDR2 comprising the amino acid sequence of SEQ ID NO: 78; and/or
(c) a VH CDR3 comprising the amino acid sequence of SEQ ID NO: 79.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 80; and/or
(b) a VL CDR2 comprising the amino acid sequence of SEQ ID NO: 81; and/or
(c) a VL CDR3 comprising the amino acid sequence of SEQ ID NO: 82.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 77;
(b) a VH CDR2 comprising the amino acid sequence of SEQ ID NO: 78;
(c) a VH CDR3 comprising the amino acid sequence of SEQ ID NO: 79;
(d) a VL CDR1 comprising the amino acid sequence of SEQ ID NO: 80;
(e) a VL CDR2 comprising the amino acid sequence of SEQ ID NO: 81; and/or
(f) a VL CDR3 comprising the amino acid sequence of SEQ ID NO: 82.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 83; and/or
(b) a VH CDR2 comprising the amino acid sequence of SEQ ID NO: 84; and/or
(c) a VH CDR3 comprising the amino acid sequence of SEQ ID NO: 85.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 86; and/or
(b) a VL CDR2 comprising the amino acid sequence of SEQ ID NO: 87; and/or
(c) a VL CDR3 comprising the amino acid sequence of SEQ ID NO: 88.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 83;
(b) a VH CDR2 comprising the amino acid sequence of SEQ ID NO: 84;
(c) a VH CDR3 comprising the amino acid sequence of SEQ ID NO: 85;
(d) a VL CDR1 comprising the amino acid sequence of SEQ ID NO: 86;
(e) a VL CDR2 comprising the amino acid sequence of SEQ ID NO: 87; and/or
(f) a VL CDR3 comprising the amino acid sequence of SEQ ID NO: 88.

In some embodiments, the anti-FAM19A5 antibody or antigen-binding portion thereof of the disclosure, which specifically binds to human FAM19A5, comprises:
(a) a VH CDR1 comprising the amino acid sequence of SEQ ID NO: 89; and/or
(b) a VH CDR2 comprising the amino acid sequence of SEQ ID NO: 90; and/or
(c) a VH CDR3 comprising the amino acid sequence of SEQ ID NO: 91.

In specific embodiments, the antibody or antigen-binding portion thereof comprises one, two, or all three of the VH CDRs above.

In some embodiments, the anti-FAM19A5 antibody or antigen-binding portion thereof, which specifically binds to human FAM19A5, comprises:
(a) a VL CDR1 comprising the amino acid sequence of SEQ ID NO: 92; and/or
(b) a VL CDR2 comprising the amino acid sequence of SEQ ID NO: 93; and/or
(c) a VL CDR3 comprising the amino acid sequence of SEQ ID NO: 94.

In specific embodiments, the antibody or antigen-binding portion thereof comprises one, two, or all three of the VL CDRs above.

In some embodiments, the anti-FAM19A5 antibody or antigen-binding portion thereof, which specifically binds to human FAM19A5, comprise:
(a) a VH CDR1 comprising the amino acid sequence of SEQ ID NO: 89;
(b) a VH CDR2 comprising the amino acid sequence of SEQ ID NO: 90;
(c) a VH CDR3 comprising the amino acid sequence of SEQ ID NO: 91;
(d) a VL CDR1 comprising the amino acid sequence of SEQ ID NO: 92;
(e) a VL CDR2 comprising the amino acid sequence of SEQ ID NO: 93; and/or
(f) a VL CDR3 comprising the amino acid sequence of SEQ ID NO: 94.

In specific embodiments, the anti-FAM19A5 antibody or antigen-binding portion thereof comprises one, two, three, four, five, or six of the CDRs above.

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific embodiments, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which specifically binds to an FAM19A5 polypeptide (e.g., human FAM19A5) comprises a light chain which comprises any VL or VL CDR amino acid sequences described herein, and wherein the constant region of the light chain comprises the amino acid sequence of a human kappa light chain constant region. In a particular embodiment, an antibody described herein, which specifically binds to an FAM19A5 polypeptide (e.g., human FAM19A5) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al., (1991) supra.

With respect to the heavy chain, in some embodiments, the heavy chain of an antibody described herein can be an alpha ($\alpha$), delta ($\delta$), epsilon ($\varepsilon$), gamma ($\gamma$) or mu ($\mu$) heavy chain. In another specific embodiment, the heavy chain of an antibody described can comprise a human alpha ($\alpha$), delta ($\delta$), epsilon ($\varepsilon$), gamma ($\gamma$) or mu ($\mu$) heavy chain. In one embodiment, an antibody described herein, which specifically binds to FAM19A5 (e.g., human FAM19A5), comprises a heavy chain which comprises a VH or VH CDR amino acid sequence described herein, and wherein the constant region of the heavy chain comprises the amino acid sequence of a human gamma ($\gamma$) heavy chain constant region. In another embodiment, an antibody described herein, which specifically binds to FAM19A5 (e.g., human FAM19A5), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some embodiments, an antibody described herein, which specifically binds to FAM19A5 (e.g., human FAM19A5) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which specifically binds to FAM19A5 (e.g., human FAM19A5) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some embodiments, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. *Front Immunol.* 5:520 (published online Oct. 20, 2014) and Jefferis R. and Lefranc M P, *mAbs* 1:4, 1-7 (2009). In some embodiments, the constant regions comprise the amino acid sequences of the constant regions of a human IgG1, IgG2, IgG3, or IgG4, or variants thereof.

In certain embodiments, the anti-FAM19A5 antibody or antigen binding portion thereof disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (Fc$\gamma$R) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, F(ab')$_2$, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see e.g., U.S. Pub. No. 20120100140); (3) employing Fc regions from an IgG subclass that have reduced effector function (e.g., an Fc region from IgG2 or IgG4 antibodies or a chimeric Fc region comprising a CH2 domain from IgG2 or IgG4 antibodies, see, e.g., U.S. Pub. No. 20120100140 and Lau C. et al., *J. Immunol.* 191:4769-4777 (2013)); and (4) generating an Fc region with mutations that result in reduced or no Fc functions. See, e.g., U.S. Pub. No. 20120100140 and U.S. and PCT applications cited therein and An et al., *mAbs* 1:6, 572-579 (2009).

Thus, in some embodiments, the anti-FAM19A5 antibody or antigen binding portion thereof disclosed herein is an Fab, an Fab', an F(ab')2, an Fv, a single chain Fv (scFv), or a sdAb consisting of a monomeric VH or VL domain. Such antibody fragments are well known in the art and are described supra.

In some embodiments, the anti-FAM19A5 antibody or antigen binding portion thereof disclosed herein comprises an Fc region with reduced or no Fc effector function. In some embodiments, the constant regions comprise the amino acid sequences of the Fc region of a human IgG2 or IgG4, in some embodiments, the anti-FAM19A5 antibody is of an IgG2/IgG4 isotype. In some embodiments, the anti-FAM19A5 antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or an Fc region with mutations that result in reduced or no Fc functions. Fc regions with reduced or no Fc effector function include those known in the art. See, e.g., Lau C. et al., *J. Immunol.* 191:4769-4777 (2013); An et al., *mAbs* 1:6, 572-579 (2009); and U.S. Pub. No. 20120100140 and the U.S. patents and publications and PCT publications cited therein. Also Fc regions with reduced or no Fc effector function can be readily made by a person of ordinary skill in the art.

IV. Nucleic Acid Molecules

Another aspect described herein pertains to one or more nucleic acid molecules that encode any one of the antibodies or antigen binding portions thereof described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Certain nucleic acids molecules described herein are those encoding the VH and VL sequences of the anti-FAM19A5 antibodies of the present disclosure. Exemplary DNA sequences encoding the VH and VL sequences are set forth in Tables 6 and 7, respectively.

TABLE 6

Variable heavy chain polynucleotide sequence

| Antibody | Variable Heavy Chain Polynucleotide Sequence (SEQ ID NO) |
|---|---|
| Anti-FAM19A5 (1-65) | GCCGTGACACTGGACGAATCTGGGGGAGGGCTGCAGACTCCAGGCGGAGCTCTGAGCCTG GTGTGCAAGGCATCCGGGTTCACCTTTAGCTCCTACCAGATGGGATGGGTGCGGCAGGCA CCAGGGAAGGGCCTGGAGTGGGTCGGAGTGATCAACAAATCTGGGAGTGACACAAGCTAC GGCAGCGCCGTGAAGGGAAGGGCCACCATCAGCAGGGACAATGGCCAGAGTACCGTGCGG CTGCAGCTGAACAATCTGCGCGCTGAGGACACTGGCACCTACTTCTGTGCTAAGGGATCA GCAAGCTATATCACAGCCGCTACTATTGATGCATGGGGACACGGGACAGAAGTCATCGTG TCTAGT (SEQ ID NO: 18) |
| Anti-FAM19A5 (P2-C12) | CAGTCGCTGGAGGAGTCCGGGGGTCGCCTGGTCACGCCTGGGACACCCCTGACACTCACC TGCACCGTCTCTGGATTCTCCCTCAGTACCTATGCAGTGACCTGGGTCCGCCAGGCTCCA GGGAAGGGGCTGGAATGGATCGGATACATTAATTGGCGTGGTGGGACATCCTACGCGAAC TGGGCGAAAGGCCGATTCACCATCTCCAAAACCTCGTCGACCACGGTGGATCTGAAAATG ACCAGTCCGACAACCGAGGACACGGCCACCTATTTCTGTGCCAGAGATGCTAGTAGTGGT GCTGCTTTTGGGTCTTACGGCATGGACCCCTGGGGCCCAGGGACCCTCGTCACCGTCTCT TCA (SEQ ID NO: 143) |

TABLE 7

Variable light chain polynucleotide sequence

| Antibody | Variable Light Chain Polynucleotide Sequence (SEQ ID NO) |
|---|---|
| Anti-FAM19A5 (1-65) | GCCCTGACTCAGCCCTCTTCCGTGTCAGCCAACCCTGGAGAAACTGTGAAGATCACCTGC AGCGGAGGAGGGAGCTCCGGATACGGATATGGGTGGTATCAGCAGAAATCCCCATCTAGT GCCCCCCTGACTGTGATCTATTGGAACGACAAGAGGCCTAGTGATATTCCATCAAGATTC AGTGGATCAAAAAGCGGGTCCACTCACACCCTGACAATCACTGGCGTGCAGGCAGAGGAC GAAGCCGTCTACTTCTGCGGAAATGACGATTACTCAAGCGATTCTGGCTATGTGGGCGTC TTTGGCGCAGGAACCACACTGACAGTGCTG (SEQ ID NO: 19) |
| Anti-FAM19A5 (P2-C12) | GAGCTCGATATGACCCAGACTCCATCCTCCGTGTCTGCAGCTGTGGGAGGCACAGTCACC ATCAAGTGCCAGGCCAGTCAGAGCATTAGTAGCTACTTATCCTGGTATCAGCAGAAACCA GGGCAGCCTCCCAAGCTCCTGATCTATGAAGCATCCAAACTGGCCTCTGGGGTCCCATCG CGGTTCAGCGGCAGTGGATATGGGACAGAGTTCACTCTCACCATCAGCGACCTGGAGTGT GCCGATGCTGCCACTTACTACTGTCAACAGGGTTATAGTAGTACTAATGTTTGGAATGCT TTCGGCGGAGGCACCAATGTGGAAATCAAA (SEQ ID NO: 154) |

A method for making an anti-FAM19A5 antibody as disclosed herein can comprise expressing the heavy chain and the light chains in a cell line comprising the nucleotide sequences encoding the heavy and light chains with a signal peptide, e.g., SEQ ID NO: 18 and 19, respectively. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG2 and/or IgG 4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al. (1988) Science 242:423-426; Huston et al. (1988) Proc. Natl. Acad. Sci. USA 85:5879-5883; McCafferty et al. (1990) Nature 348:552-554).

In some embodiments, the present disclosure provides a vector comprising an isolated nucleic acid molecule comprising a nucleotide sequence encoding an antibody or antigen binding portion thereof. In other embodiments, the vectors can be used for gene therapy.

Suitable vectors for the disclosure include expression vectors, viral vectors, and plasmid vectors. In one embodiment, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen binding portion thereof described herein. In one embodiment, the coding sequences for the antibody or antigen binding portion thereof is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen binding portion thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

V. Antibody Production

Antibodies or fragments thereof that immunospecifically bind to FAM19A5 (e.g., human FAM19A5) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In a certain aspect, provided herein is a method of making an antibody or an antigen-binding fragment thereof which immunospecifically binds to FAM19A5 (e.g., human FAM19A5) comprising culturing a cell or host cell described herein. In a certain aspect, provided herein is a method of making an antibody or an antigen-binding fragment thereof which immunospecifically binds to FAM19A5 (e.g., human FAM19A5) comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody immunospecifically binds to FAM19A5 (e.g., human FAM19A5) as determined, e.g., by ELISA or other antigen-binding or competitive binding assay known in the art or in the Examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) *Nature* 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al, supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., human FAM19A5) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) *Hybridoma* 16:381-9, incorporated by reference in its entirety).

In some embodiments, mice (or other animals, such as chickens, rats, monkeys, donkeys, pigs, sheep, hamster, or dogs) can be immunized with an antigen (e.g., FAM19A5 such as human FAM19A5) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NSO myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NSO cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) *J Immunol* 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against FAM19A5 (e.g., human FAM19A5). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific FAM19A5 (e.g., human FAM19A5) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or non-human such as murine or chicken cDNA libraries of affected tissues). The DNAs encoding the VH and VL domains are recombined together with a scFv linker by PCR and cloned into a phagemid vector. The vector is electroporated in *E. coli* and the *E. coli* is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) *J Immunol Methods* 182: 41-50; Ames R S et al., (1995) *J Immunol Methods* 184: 177-186; Kettleborough C A et al., (1994) *Eur J Immunol* 24: 952-958; Persic L et al., (1997) *Gene* 187: 9-18; Burton D R & Barbas C F (1994) *Advan Immunol* 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')2 fragments can also be employed using methods known in the art such as those disclosed in PCT publication No. WO 92/22324; Mullinax R L et al., (1992) *BioTechniques* 12(6): 864-9; Sawai H et al., (1995) *Am J Reprod Immunol* 34: 26-34; and Better M et al., (1988) *Science* 240: 1041-1043.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a non-human animal (e.g., mouse, rat or chicken) monoclonal antibody fused to a constant region of a human antibody. Methods for producing chimeric antibodies are known in the art. See, e.g., Morrison S L (1985) *Science* 229: 1202-7; Oi V T & Morrison S L (1986) *BioTechniques* 4: 214-221; Gillies S D et al., (1989) *J Immunol Methods* 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine or a chicken immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG1, IgG2, IgG3 and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) *Mol Immunol* 28(4/5): 489-498; Studnicka G M et al., (1994) *Prot Engineering* 7(6): 805-814; and Roguska M A et al., (1994) *PNAS* 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) *J Immunol* 169: 1119-25; Caldas C et al., (2000) *Protein Eng.* 13(5): 353-60; Morea V et al., (2000) *Methods* 20(3): 267-79; Baca M et al., (1997) *J Biol Chem* 272(16): 10678-84; Roguska M A et al., (1996) *Protein Eng* 9(10): 895 904; Couto J R et al., (1995) *Cancer Res.* 55 (23 Supp): 5973s-5977s; Couto J R et al., (1995) *Cancer Res* 55(8): 1717-22; Sandhu J S (1994) *Gene* 150(2): 409-10 and Pedersen J T et al., (1994) *J Mol Biol* 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) *J Immunol* 231: 25-38; Nuttall S D et al., (2000) *Curr Pharm Biotechnol* 1(3): 253-263; Muyldermans S, (2001) *J Biotechnol* 74(4): 277-302; U.S. Pat. No. 6,005,079; and International Publication Nos. WO 94/04678, WO 94/25591 and WO 01/44301.

Further, antibodies that immunospecifically bind to a FAM19A5 antigen can, in turn, be utilized to generate anti-idiotype antibodies that "mimic" an antigen using techniques well known to those skilled in the art. (See, e.g., Greenspan N S & Bona C A (1989) *FASEB J* 7(5): 437-444; and Nissinoff A (1991) *J Immunol* 147(8): 2429-2438).

In particular embodiments, an antibody described herein, which binds to the same epitope of FAM19A5 (e.g., human FAM19A5) as an anti-FAM19A5 antibody described herein, is a human antibody or an antigen-binding fragment thereof. In particular embodiments, an antibody described herein, which competitively blocks (e.g., in a dose-dependent manner) antibodies described herein, (e.g., 1-65) from binding to FAM19A5 (e.g., human FAM19A5), is a human antibody or an antigen-binding fragment thereof.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., FAM19A5). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) *Int Rev Immunol* 13: 65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the XENO-MOUSE™ (Abgenix, Inc.; U.S. Pat. Nos. 6,075,181 and 6,150,184), the HUAB-MOUSE™ (Mederex, Inc./Gen Pharm; U.S. Pat. Nos. 5,545,806 and 5,569,825), the TRANS CHROMO MOUSE™ (Kirin), and the KM MOUSE™ (Medarex/Kirin).

Human antibodies which specifically bind to FAM19A5 (e.g., human FAM19A5) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., FAM19A5 such as human FAM19A5)). Such methods are known and are described in the art, see, e.g., Shinmoto H et al., (2004) Cytotechnology 46: 19-23; Naganawa Y et al., (2005) Human Antibodies 14: 27-31.

VI. Methods of Engineering Antibodies

As discussed above, the anti-FAM19A5 antibody or antigen binding portion thereof having VH and VL sequences disclosed herein can be used to create new anti-FAM19A5 antibody or antigen binding portion thereof by modifying the VH and/or VL sequences, or the constant region(s) attached thereto. Thus, in another aspect described herein, the structural features of an anti-FAM19A5 antibody described herein is used to create structurally related anti-FAM19A5 antibodies that retain at least one functional property of the antibodies described herein, such as binding to human FAM19A5. For example, the starting material for the engineering method is VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, provided herein are methods for preparing an anti-FAM19A5 antibody or antigen binding portion thereof comprising:
(a) providing: (i) a heavy chain variable region sequence comprising a CDR1, CDR2, and/or CDR3 sequence as set forth in Table 2 or a CDR1, CDR2, and/or CDR3 of the heavy chain variable region as set forth in Table 4; and (ii) a light chain variable region sequence comprising a CDR1, CDR2, and/or CDR3 sequence as set forth in Table 3 or a CDR1, CDR2, and/or CDR3 of the heavy chain variable region as set forth in Table 5;
(b) altering at least one amino acid residue within the heavy chain variable region sequence and/or the light chain variable region sequence to create at least one altered antibody or antigen binding portion sequence; and
(c) expressing the altered antibody or antigen binding portion sequence as a protein.

Standard molecular biology techniques can be used to prepare and express the altered antibody or antigen binding portion sequence.

In some embodiments, the antibody or antigen binding portion thereof encoded by the altered antibody or antigen binding portion sequence(s) is one that retains one, some or all of the functional properties of the anti-FAM19A5 antibodies described herein, which include,
(1) binding to soluble human FAM19A5, e.g., with a $K_D$ of 10 nM or less (e.g., 0.01 nM to 10 nM), e.g., as measured by Biacore;
(2) binding to membrane bound human FAM19A5, e.g., with a $K_D$ of 1 nM or less (e.g., 0.01 nM to 1 nM), e.g., as measured by ELISA;
(3) binding to membrane bound human FAM19A5, e.g., with an EC50 of 1 nM or less (e.g., 0.01 nM to 1 nM), e.g., as measured by ELISA;
(4) reduces, reverses, delays, and/or prevents an onset of reactive gliosis;
(5) suppresses an excessive proliferation of reactive astrocytes;
(6) decreases expression of chondroitin sulfate proteoglycans including neurocan and neuron-glial antigen 2 (NG2);
(7) increases expression of c-fos and pERK in the nucleus of neurons;
(8) promotes survival of neurons;
(9) increases expression of GAP43 in neurons;
(10) promotes regrowth of an axon; and
(11) competing in either direction or both directions for binding to human FAM19A5 with an anti-FAM19A5 antibody disclosed herein.

The altered antibody or antigen binding portion thereof can exhibit one or more, two or more, three or more, four or more, five or more, six or more, seven or more, eight or more, nine or more, ten or more, eleven, or all of the functional properties set forth as (1) through (11) above. The functional properties of the altered antibodies or antigen binding portions thereof can be assessed using standard assays available in the art and/or described herein, such as those set forth in the Examples (e.g., ELISAs, FACS).

In certain embodiments of the methods of engineering antibodies described herein, mutations can be introduced randomly or selectively along all or part of an anti-FAM19A5 antibody coding sequence and the resulting modified anti-FAM19A5 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

VII. Cells and Vectors

In certain aspects, provided herein are cells (e.g., host cells) expressing (e.g., recombinantly) antibodies described herein (or an antigen-binding fragment thereof) which specifically bind to FAM19A5 (e.g., human FAM19A5) and related polynucleotides and expression vectors. Provided herein are vectors (e.g., expression vectors) comprising polynucleotides comprising nucleotide sequences encoding anti-FAM19A5 antibodies or a fragment for recombinant expression in host cells, e.g., in mammalian cells. Also provided herein are host cells comprising such vectors for recombinantly expressing anti-FAM19A5 antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to FAM19A5 (e.g., human FAM19A5) involves construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the VH and/or VL, or one or more of the VH and/or VL CDRs, of an anti-FAM19A5 antibody of the present disclosure) or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-FAM19A5 antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-FAM19A5 antibody described herein, and a second vector comprising a polynucleotide encoding a heavy chain/heavy chain variable region of an anti-FAM19A5 antibody described herein.

A variety of host-expression vector systems can be utilized to express antibody molecules described herein. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NSO, PER.C6, VERO, CRL7030, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS SYSTEM™ (Lonza). In a particular embodiment, cells for expressing antibodies described herein are human cells, e.g., human cell lines. In a specific embodiment, a mammalian expression vector is POPTIVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) *Gene* 45: 101-5; and Cockett M I et al., (1990) *Biotechnology* 8(7): 662-7). In certain embodiments, antibodies described herein are produced by CHO cells or NSO cells. In a specific embodiment, the expression of nucleotide sequences encoding antibodies described herein which immunospecifically bind FAM19A5 (e.g., human FAM19A5) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the E. coli expression vector pUR278 (Ruether U & Mueller-Hill B (1983) *EMBO J* 2: 1791-1794), in which the antibody coding sequence can be ligated individually into the vector in frame with the lac Z coding region so that a fusion protein is produced; pIN vectors (Inouye S & Inouye M (1985) *Nuc Acids Res* 13: 3101-3109; Van Heeke G & Schuster S M (1989) *J Biol Chem* 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (see, e.g., Logan J & Shenk T (1984) *PNAS* 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) *Methods Enzymol.* 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT20 and T47D, NSO (a murine myeloma cell line that does not endogenously produce any immunoglobulin chains), CRL7030, COS (e.g., COS 1 or COS), PER.C6, VERO, HsS78Bst, HEK-293T, HepG2, SP210, R1.1, B-W, L-M, BSC 1, BSC40, YB/20, BMT10 and HsS78Bst cells. In certain embodiments, anti-FAM19A5 antibodies described herein are produced in mammalian cells, such as CHO cells.

In a specific embodiment, the antibodies described herein or antigen-binding portions thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of 1,6-fucosyltransferase can be used to produce antibodies or antigen-binding portions thereof with reduced fucose content. The POTELLIGENT® system (Lonza) is an example of such a system that can be used to produce antibodies or antigen-binding portions thereof with reduced fucose content.

For long-term, high-yield production of recombinant proteins, stable expression cells can be generated. For example, cell lines which stably express an anti-FAM19A5 antibody described herein an antigen-binding portion thereof can be engineered. In specific embodiments, a cell provided herein stably expresses a light chain/light chain variable domain and a heavy chain/heavy chain variable domain which associate to form an antibody described herein or an antigen-binding portion thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-FAM19A5 antibody described herein or an antibody binding portion thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) *Cell* 11(1): 223-32), hypoxanthine-guanine phosphoribosyltransferase (Szybalska E H & Szybalski W (1962) *PNAS* 48(12): 2026-2034) and adenine phosphoribosyltransferase (Lowy I et al., (1980) *Cell* 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) *PNAS* 77(6): 3567-70; O'Hare K et al., (1981) *PNAS* 78: 1527-31); gpt, which confers resistance to mycophenolic acid (Mulligan R C & Berg P (1981) *PNAS* 78(4): 2072-6); neo, which confers resistance to the aminoglycoside G-418 (Wu G Y & Wu C H (1991) *Biotherapy* 3: 87-95; Tolstoshev P (1993) *Ann Rev Pharmacol Toxicol* 32: 573-596; Mulligan R C (1993) *Science* 260: 926-932; and Morgan R A & Anderson W F (1993) *Ann Rev Biochem* 62: 191-217; Nabel G J & Feigner P L (1993) *Trends Biotechnol* 11(5): 211-5); and hygro, which confers resistance to hygromycin (Santerre R F et al., (1984) *Gene* 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbere-Garapin F et al., (1981) *J Mol Biol* 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) *Mol Cell Biol* 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) *Nature* 322: 562-565; and Kohler G (1980) *PNAS* 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or an antigen-binding portion thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (or antibody binding portions). When the antibody is recombinantly produced, it is also generally substantially free of culture medium, i.e., culture medium represents less than about 20%>, 10%>, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

VIII. Assays

Antibodies described herein can be tested for binding to FAM19A5 by, for example, standard ELISA. Briefly, microtiter plates are coated with purified FAM19A5 at 1-2 µg/ml in PBS, and then blocked with 5% bovine serum albumin in PBS. Dilutions of antibody (e.g., dilutions of plasma from FAM19A5-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human FAM19A5, but not to a control cell line that does not express FAM19A5. Briefly, the binding of anti-FAM19A5 antibodies is assessed by incubating FAM19A5 expressing CHO cells with the anti-FAM19A5 antibody at 1:20 dilution. The cells are washed and binding is detected with a PE-labeled anti-human IgG Ab. Flow cytometric analyses are performed using a FACS can flow cytometry (Becton Dickinson, San Jose, Calif.). Preferably, mice which develop the highest titers will be used for fusions.

An ELISA assay as described above can be used to screen for antibodies and, thus, hybridomas that produce antibodies that show positive reactivity with the FAM19A5 immunogen. Hybridomas that produce antibodies that bind, preferably with high affinity, to FAM19A5 can then be subcloned and further characterized. One clone from each hybridoma, which retains the reactivity of the parent cells (by ELISA), can then be chosen for making a cell bank, and for antibody purification.

To purify anti-FAM19A5 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD 280 using 1.43 extinction coefficient. The monoclonal antibodies can be aliquoted and stored at −80° C.

To determine if the selected anti-FAM19A5 monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using FAM19A5 coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing FAM19A5, flow cytometry can be used, as described in the Examples. Briefly, cell lines expressing membrane-bound FAM19A5 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy can be used (in addition to or instead of) the flow cytometry assay. Cells can be stained exactly as described above and examined by fluorescence microscopy. This method allows visualization of individual cells, but can have diminished sensitivity depending on the density of the antigen.

Anti-FAM19A5 antibodies can be further tested for reactivity with the FAM19A5 antigen by Western blotting. Briefly, cell extracts from cells expressing FAM19A5 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-FAM19A5 antibodies include standard assays known in the art, for example, BIACORE™ surface plasmon resonance (SPR) analysis using a BIACORE™ 2000 SPR instrument (Biacore AB, Uppsala, Sweden).

In one embodiment, an antibody specifically binds to the soluble form of human FAM19A5. In one embodiment, an antibody specifically binds to the membrane-bound form of human FAM19A5. An antibody can specifically bind to a particular epitope of FAM19A5 (e.g., a SEQ ID NO: 2 or a fragment within SEQ ID NO: 2). In certain embodiments, the antibody specifically binds human FAM19A5, preferably, with high affinity, and does not cross-react to other members of the FAM19 subfamily of proteins.

IX. Bispecific Molecules

Antibodies described herein can be used for forming bispecific molecules. An anti-FAM19A5 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. Cytokines such as IL-6, CNTF, LIF, EGF and TGFα, have been implicated as triggers of onset of gliosis and/or reactive astrogliosis (Balasingam et al., *J. Neurosci.* 14(2):846-56 (1994); Winter et al., *Proc. Natl. Acad. Sci. U.S.A.* 20; 92(13):5865-9 (1995)) by activating the protein signal transducer and activator of transcription 3 (STAT3), which then regulates many aspects of reactive astrogliosis after CNS injury. Herrmann J. E. et al., *J. Neurosci.* 28(28): 7231-7243 (2008). For example, absence or reduced STAT3 leads to attenuated up-regulation of Glial fibrillary acidic protein (GFAP), failure of astrocyte hypertrophy, and increased spread of inflammation, increased lesion volume and partially attenuated motor recovery after CNS injury. Herrmann J. E. et al., *J. Neurosci.* 28(28): 7231-7243 (2008). Thus, for example, an anti-FAM19A5 antibody can be linked to an antibody or scFv that binds specifically to any protein that is involved in inhibiting onset of gliosis and/or excessive proliferation of reactive astrogliosis for combination treatments, e.g., antibodies to IL-6, CNTF, LIF, EGF or TGFα.

Also, an anti-FAM19A5 antibody can be linked to an antibody or scFv that treats a disease or disorder including a central nervous system damage (e.g., a traumatic brain injury, a cerebrospinal damage, a stroke, or a brain tumor), a cerebrospinal system damage, a degenerative brain disorder (e.g., Huntington's disease, Parkinson's disease, Alzheimer's disease, multiple sclerosis, ALS), a degenerative cerebrospinal or nerve disorder, or a neuropathic pain in a subject (see diseases or disorders in Section XII below). For example, an anti-FAM19A5 antibody can be linked to an antibody or scFv, e.g., Natalizumab (TYSABRI®), Alemtuzumab (LEMTRADA®), that treats multiple sclerosis.

The antibody described herein can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody binding portion thereof, peptide or binding mimetic, such that a bispecific molecule results. In one embodiment, a bispecific molecule binds to FAM19A5 and VEGF. In another embodiment, a bispecific molecule binds to FAM19A5 and EGF.

Accordingly, provided herein are bispecific molecules comprising at least one first binding specificity for FAM19A5 and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody binding portion thereof, including, e.g., an Fab, Fab', F(ab')$_2$, Fv, or a single chain Fv (scFv). The antibody can also be a light chain or heavy chain dimer, or any minimal fragment thereof such as a Fv or a single chain construct as described in Ladner et al., U.S. Pat. No. 4,946,778, the contents of which is expressly incorporated by reference.

While human monoclonal antibodies are preferred, other antibodies which can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohexane-1-carboxylate (sulfo-SMCC) (see, e.g., Karpovsky et al., (1984) *J. Exp. Med.* 160: 1686; Liu, M A et al., (1985) *Proc. Natl. Acad. Sci. USA* 82:8648). Other methods include those described in Paulus (1985) Behring Ins. Mitt. No. 78, 118-132; Brennan et al., (1985) *Science* 229:81-83), and Glennie et al., (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, mAb× (scFv) 2, Fab×F(ab')2 or ligand×Fab fusion protein. A bispecific antibody can comprise an antibody comprising an scFv at the C-terminus of each heavy chain. A bispecific molecule described herein can be a single chain molecule comprising one single chain antibody and a binding determinant, or a single chain bispecific molecule comprising two binding determinants. Bispecific molecules can comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

X. Diagnosis

In one embodiment the moiety attached to an anti-FAM19A5 antibody is selected from the group consisting of a binding moiety, a labeling moiety, and a biologically active moiety.

Antibodies described herein can be used for diagnostic purposes, including sample testing and in vivo imaging, and for this purpose the antibody (or binding portion thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the N2S2, N3S or N4 type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Antibodies described herein can also be conjugated to a therapeutic agent to form an immunoconjugate such as an antibody-drug conjugate (ADC). Suitable therapeutic agents include agents modulate onset of gliosis and/or reactive astrogliosis and/or treating degenerative brain disorders, central nervous system damage, or neuropathic pain. Therapeutic agents for treating degenerative brain disorders include drugs for treating Huntington's disease, Parkinson's disease, Alzheimer's disease, multiple sclerosis, and Amyotrophic Lateral Sclerosis (ALS). This include drugs commonly used for treating such degenerative brain disorders, e.g., drugs disclosed infra in Section XII.

Immunoconjugates can be prepared by methods known in the art. Preferably, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see, e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see, e.g., Hackenberger, C. P. R., and Schwarzer, D., *Angew. Chem. Int. Ed. Engl.* 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al., *Chem. Biol.* 15 (2008) 128-136; and Protease-catalyzed formation of C—N bonds is used by Bordusa, F., Highlights in Bioorganic Chemistry (2004) 389-403).

Site specific reaction and covalent coupling can also be achieved by the selective reaction of terminal amino acids with appropriate modifying reagents. The reactivity of an N-terminal cysteine with benzonitrils (see Ren, H. et al., *Angew. Chem. Int. Ed. Engl.* 48 (2009) 9658-9662) can be used to achieve a site-specific covalent coupling. Native chemical ligation can also rely on C-terminal cysteine residues (Taylor, E. Vogel; Imperiali, B, *Nucleic Acids and Molecular Biology* (2009), 22 (Protein Engineering), 65-96).

EP 1 074 563 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see, e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

XI. Pharmaceutical Compositions

Provided herein are compositions comprising an antibody or antigen-binding portion thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

In a specific embodiment, pharmaceutical compositions comprise an antibody or antigen-binding portion thereof, a bispecific molecule, or a immunoconjugate described herein, and optionally one or more additional prophylactic or therapeutic agents, in a pharmaceutically acceptable carrier. In a specific embodiment, pharmaceutical compositions comprise an effective amount of an antibody or antigen-binding portion thereof described herein, and optionally one or more additional prophylactic of therapeutic agents, in a pharmaceutically acceptable carrier. In some embodiments, the antibody is the only active ingredient included in the pharmaceutical composition. Pharmaceutical compositions described herein can be useful in enhancing, inducing or activating a FAM19A5 activity and treating a condition, such as central nervous system damage, a degenerative brain disorder, or a neuropathic pain.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition can be formulated for any route of administration to a subject. Specific examples of routes of administration include intranasal, oral, parenterally, intrathecally, intra-cerebroventricularly, pulmonarily, subcutaneously, or intraventricularly. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An antibody or antigen-binding portion thereof described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An antibody or antigen-binding portion thereof described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an antibody or antigen-binding portion thereof described herein is a lyophilized powder, which can be reconstituted for administration as solutions, emulsions and other mixtures. It can also be reconstituted and formulated as solids or gels. The lyophilized powder is prepared by dissolving an antibody or antigen-binding portion thereof described herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The antibodies or antigen-binding portions thereof, the bispecific molecule, or the immunoconjugate described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874. In a specific embodiment, an antibody or antigen-binding portion thereof described herein is targeted to treat a central nervous system damage, a degenerative brain disorder, or a neuropathic pain.

The compositions to be used for in vivo administration can be sterile. This is readily accomplished by filtration through, e.g., sterile filtration membranes.

XII. Kits

Provided herein are kits comprising one or more antibodies described herein, or antigen-binding portions thereof, bispecific molecules, or immunoconjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding portion thereof, optional an instructing for use. In some embodiments, the kits contain a pharmaceutical composition described herein and any prophylactic or therapeutic agent, such as those described herein.

XIII. Therapeutic Uses and Methods

In one aspect, presented herein are methods for mitigating injury or damage to the CNS in a subject, comprising to a subject in need thereof administering an anti-FAM19A5 antibody or antigen-binding portion thereof, a bispecific molecule, or an immunoconjugate described herein, or a composition thereof.

In one embodiment, presented herein are methods for inhibit, slowing down, suppress, curb, or prevent the beginning or initiation of gliosis and its associated detrimental effects of the CNS in a subject comprising to a subject in need thereof administering an anti-FAM19A5 antibody or antigen-binding portion thereof, a bispecific molecule or an immunoconjugate disclosed herein, or a composition thereof. In one embodiment, presented herein are methods for inhibit, slowing down, suppress, curb, or prevent excessive or abnormal proliferation of reactive astrocytes and its associated detrimental effects of the CNS in a subject comprising to a subject in need thereof administering an anti-FAM19A5 antibody or antigen-binding portion thereof, a bispecific molecule or an immunoconjugate disclosed herein, or a composition thereof. In one embodiment, presented herein are methods for or decrease, inhibit, reduce the level of neurocan, NG2, or both, or reduce the activity of or render inactive neurocan, NG2, or both in a subject comprising to a subject in need thereof administering an anti-FAM19A5 antibody or antigen-binding portion thereof, a bispecific molecule or an immunoconjugate disclosed herein, or a composition thereof. In one embodiment, presented herein are methods for stimulating, promoting, increasing, or activating growth of neurons, preferably after injury or damage in a subject comprising to a subject in need thereof administering an anti-FAM19A5 antibody or antigen-binding portion thereof, a bispecific molecule or an immunoconjugate disclosed herein, or a composition thereof. In one embodiment, presented herein are methods for increase the level of c-fos mRNA, c-fos protein, or c-fos protein activity and increase the level of ERK mRNA, ERK protein, or pERK activity, preferably in the nucleus of neurons, in a subject in need thereof administering an anti-FAM19A5 antibody or antigen-binding portion thereof, a bispecific molecule or an immunoconjugate disclosed herein, or a composition thereof. In one embodiment, presented herein are methods for enhancing or increasing the level of GAP43 mRNA, GAP43 protein, or increasing the activity of GAP43 protein, preferably in the neurons, in a subject in need thereof administering an anti-FAM19A5 antibody or antigen-binding portion thereof, a bispecific molecule or an immunoconjugate disclosed herein, or a composition thereof. In one embodiment, presented herein are methods for enhancing or promotes survival of neurons and/or promotes regrowth of an axon, in a subject in need thereof comprising administering an anti-FAM19A5 antibody or antigen-binding portion thereof, a bispecific molecule or an immunoconjugate disclosed herein, or a composition thereof. In one embodiment, the subject is a human, preferably a human having neurons injury or damage from e.g., CNS damage, trauma, injury, cerebrospinal damage, brain tumor, infection, ischemia, stroke, autoimmune responses, and/or neurodegenerative disease.

In some embodiments, presented herein are methods for treating a disease or disorder including a central nervous system damage, a cerebrospinal system damage, a degenerative brain disorder, a degenerative cerebrospinal or nerve disorder, or a neuropathic pain, in a subject in need thereof, comprising administering to the subject an anti-FAM19A5 antibody or antigen-binding portion thereof, a bispecific molecule or an immunoconjugate disclosed herein, or a composition thereof. In one embodiment, the central nervous system damage is a traumatic brain injury, a cerebrospinal damage, a stroke, a brain tumor, or a combination thereof. In one embodiment, the degenerative brain disorder is Huntington's disease, Parkinson's disease, Alzheimer's disease, multiple sclerosis, Amyotrophic Lateral Sclerosis (ALS), or a combination thereof. Thus, in one embodiment, disclosed herein is a method for treating a traumatic brain injury, a cerebrospinal damage, a stroke, a brain tumor, or a combination thereof in a subject in need thereof comprising administering to the subject an anti-FAM19A5 antibody or antigen-binding portion thereof, a bispecific molecule or an immunoconjugate disclosed herein, or a composition thereof. In one embodiment, disclosed herein is a method for treating Huntington's disease, Parkinson's disease, Alzheimer's disease, multiple sclerosis, ALS in a subject in need thereof comprising administering to the subject an anti-FAM19A5 antibody or antigen-binding portion thereof, a bispecific molecule or an immunoconjugate disclosed herein, or a composition thereof. In preferred embodiments, the subject is a human.

In some embodiments, a therapeutically effective amount of an anti-FAM19A5 antibody or antigen-binding portion thereof, a bispecific molecule or an immunoconjugate disclosed herein is administered. When treating a subject (e.g., a human), a therapeutically effective amount of an anti-FAM19A5 antibody or antigen-binding portion thereof, a bispecific molecule or an immunoconjugate disclosed herein depends on factors such as age, gender, severity of the disease and can be determined by one of ordinary skill in the art (e.g., a doctor). Typically, the anti-FAM19A5 antibody or antigen-binding portion thereof, a bispecific molecule or an immunoconjugate disclosed herein is administered at a dose of between 0.01 µg to 1000 mg per day. The anti-FAM19A5 antibody or antigen-binding portion thereof, a bispecific molecule or an immunoconjugate disclosed herein can be administered one, twice, or more times a day depending on the symptom and severity of the disease or disorder In some embodiments, an anti-FAM19A5 antibody or antigen-binding portion thereof, a bispecific molecule or an immunoconjugate, or a composition thereof disclosed herein is administered intravenously, orally, parenterally, intrathecally, intra-cerebroventricularly, pulmonarily, subcutaneously, or intraventricularly.

In some embodiments, an anti-FAM19A5 antibody or antigen-binding portion thereof, or a composition thereof can be administered in combination with one or more additional agent for treating a central nervous system damage (e.g., a traumatic brain injury, a cerebrospinal damage, a stroke, or a brain tumor), a cerebrospinal system damage, a degenerative brain disorder (e.g., Huntington's disease, Parkinson's disease, Alzheimer's disease, multiple sclerosis, ALS), a degenerative cerebrospinal or nerve disorder, or a neuropathic pain. For example, non-limiting exemplary agents for treating Huntington's disease include Tetrabenazine (XENAZINE®), antipsychotic drugs, such as haloperidol (HALDOL®), chlorpromazine, risperidone (rRIDPERDAL®) and quetiapine (SEROQUEL®).

Non-limiting exemplary agents for treating Parkinson's disease include levodopa (with or without Carbidopa) (LODOSYN®), dopamine agonists such as pramipexole (MIRAPEX®), ropinirole (REQUIP®), and rotigotine (NEUPRO®), and apomorphine (APOKYN®), selegiline (ELDEPRYL®, ZELAPAR®), rasagiline (AZILECT®), Entacapone (COMTAN®), benztropine (COGENTIN®), trihexyphenidyl, and amantadine.

Non-limiting exemplary agents for treating Alzheimer's disease include Donepezil (ARICEPT®), Galantamine (RAZADYNE®), and Rivastigmine (EXELON®).

Non-limiting exemplary agents for treating multiple sclerosis include Glatiramer acetate (COPAXONE®), Dimethyl fumarate (TECFIDERA®), Fingolimod (GILENYA®), Teriflunomide (AUBAGIO®), Natalizumab (TYSABRI®), Alemtuzumab (LEMTRADA®), and Mitoxantrone (NOVANTRONE®).

Non-limiting exemplary agents for treating ALS include riluzole (RILUTEK®).

Dose and administration of the one or more additional therapeutic drugs are known in the art, e.g., as instructed by the product label of the respective drug.

The following examples are offered by way of illustration and not by way of limitation.

EXAMPLES

Example 1 Expression and Purification of Human FAM19A5 Protein

Recombinant human FAM19A5 protein was produced and purified as described below and the purified protein was used in an antibody screening assay based on binding affinity analysis. First, LPS-hT plasmid expressing the FAM19A5 gene was transformed into bacteria and protein over-expression was induced. Once produced, the FAM19A5 protein was purified using an Ni-NTA affinity chromatography (Qiagen, Valencia, Calif., USA)). Using gradually higher concentration of imidazole, we removed the His-tagged FAM19A5 protein from the Ni-column. The protein expression in the solution is measured using Coomassie Brilliant Blue R-250 Dye. Taking only the FAM19A5 imidazole containing solution, we concentrated the FAM19A5 protein using PBS. When the concentration was complete, both the purity and concentration of the FAM19A5 protein were measured using a Western Blot assay. The concentrated protein was subsequently used to screen for FAM19A5-specific antibodies.

Example 2 Production of Antibody Libraries FAM19A5

1. Immunization

Cell wall components of TDW and CWS containing a water-in-oil emulsion adjuvant (RIBI+MPL+TDM+CWS adjuvant, Sigma, St. Louis, Mo., USA) in emulsified, which was then subcutaneously injected into either three chickens or into four rabbits. The chickens and the rabbits were immunized for a total of three times and four times, respectively, with approximately 2-3 weeks apart between immunizations. The titer of the antibodies obtained from the immunized was animals were measured via immuno blotting using lysates of HEK293T cells which overexpressed the FAM19A5 protein.

2. Preparation of Single-Chain Variable Fragment (scFv) Library from Immunized Chicken and Rabbit Using TRI reagent (Invitrogen, Carlsbad, Calif. USA), we extracted RNAs from the spleen, bone marrow, and synovial sac of the immunized chickens described above. Oligo-dT primers and SUPERSCRIPT™ III First-Strand Synthesis System (Invitrogen) were used to synthesize the first strand cDNA. For the cDNA obtained from the immune system of the animals, Expand High Fidelity PCR System (Roche Molecular Systems, IN, USA) was used to produce a single chain variable region library. In each reaction, 1 µL of cDNA, 60 pmol of each primer, 10 µL of 10× reaction buffer solution, 8 µL of 2.5 mM dNTP (Promega, Madison, Wis., USA), and 0.5 µL of Taq DNA polymerase were mixed with water. The final volume was 100 µL PCR reaction was performed using the following conditions: 30 cycles of (i) 15 seconds at 94° C., (ii) 30 seconds at 56° C., and (iii) 90 seconds at 72° C., followed by a final extension for 10 minutes at 72° C. The PCR products comprising a fragment having a length of about 350 bp where loaded onto a 1.5% agarose gel and after electrophoresis, QIAGEN Gel II Extraction Kit (QIAGEN, Valencia, Calif., USA) was used to purify the nucleotide fragment. The purified PCR product was quantified by reading at OD 260 nm. (1 unit OD=50 µg/ml).

Two VH and VL first product from the second PCR was connected randomly by the overlap extension PCR (Overlap extension PCR). Each PCR reaction was mixed with 100 ng of the purified VL and VH product, 60 pmol of each primer, 10 µL 10× reaction buffer, 8 µL of 2.5 mM dNTP, 0.5 µL of Taq DNA polymerase, and water in a final volume of 100 µL. PCR was performed under the following conditions: 25 cycles of (i) 15 seconds at 94° C., (ii) 30 seconds at 56° C., and (iii) 2 minutes at 72° C., followed by final extension for 10 minutes at 72° C. The PCR products comprising a single chain variable region fragment having a length of about 700 bp were loaded onto a 1.5% agarose gel and after electrophoresis, QIAGEN II Gel Extraction Kit (QIAGEN) was used to purify the nucleotide fragment. The purified PCR product was quantified by reading at OD 260 nm. (1 unit OD=50/ml).

3. Library, Ligation and Transformation

The scFv fragment of the PCR product and vector pComb3X-SS (The Scripps Research Institute, CA, USA) were digested with a Sfi I restriction enzyme. 10 µg of the purified overlapping PCT product was mixed with 360 units of Sif I, (µg DNA per 16 units, Roche Molecular Systems, Pleasanton, Calif., USA), 20 µL of a 10× reaction buffer, and water to the final volume with 200 µL. 20 µg of the pComb3X-SS vector was mixed with 120 units of Sfi I (µg DNA per 6 units), 20 µL of a 10× reaction buffer solution, and water to the final volume to 200 µL. The mixture was digested at 50° C. for 8 hours. Afterwards, the digested product comprising the scFv fragment (about 700 bp) and the vector (about 3400 bp) was loaded onto a 1% agarose gel and purified using a Gel Extraction Kit II QIAGEN (QIAGEN, Valencia, Calif., USA). 1400 ng of the Sfi I-restricted pComb3X vector and 700 ng of the digested scFv fragments were mixed with 5× a ligase buffer, 10 µL of T4 DNA ligase (Invitrogen, Carlsbad, Calif., USA), and water to a final volume of 200 µL. The mixture was incubated at 16° C. for 16 hours to perform the ligation.

After precipitation with ethanol, the DNA pellet was dissolved in 15 µL of water. To produce a library, the ligation sample was transformed into *E. coli* strain ER2738 (New England Biolabs Inc, Hitchin, Hertfordshine, SG4 OTY, England, UK) via electroporation using the vibrator gene (Gene pulser: Bio-Rad Laboratories, Hercules, Calif., USA). Cells were mixed in a 5 ml Super Broth (SB) medium and incubated while stirring at 250 rpm for one hour at 37° C. Then, 3 µL of 100 mg/mL kanamycin was added to 10 mL of SB medium. To determine the library size, 0.1 µL, 1 µL, and 10 µL of the culture sample were smeared onto Luria Broth (LB) agar plates containing 50 µg/ml of kanamycin. After stirring for 1 hour, 4.5 µL of 100 mg/mL kanamycin was added to the LB culture and further stirred for an additional 1 hour. Then, 2 ml of the VCM13 helper phage in water (>$10^{11}$ cfu/ml) was added to the LB medium, along with pre-heated LB (183 mL) containing 92.5 µL of 100 mg/mL kanamycin. This mixture was stirred at 250 rpm at 37° C. for an additional 2 hours. Next, 280 µL (50 mg/mL) of kanamycin was added to the culture and stirred overnight at 37° C. The next day, the bacteria pellet was centrifuged using a high-speed centrifuge (Beckman, JA-10 rotor) at 3,000 g, 4° C. Afterwards, the bacterial pellet was used to extract phagemid DNA, while the supernatant was transferred to sterile centrifuge bottles. Next 8 grams of polyethylene glycol-8000 (PEG-8000, Sigma) and 6 grams of sodium chloride was added (NaCl, Merck) to the supernatant, and then kept for 30 minutes in ice. Afterwards, the supernatant was centrifuged 15 minutes at 15,000 g, 4° C. The supernatant was then discarded, and the phage pellet Tris containing 1% BSA—reproduction was suspended in buffered saline (TB S).

Example 3 Library Panning (Bio-Panning) on an Immobilized Antigen

Bio-panning was performed using magnetic beads (Dynabeads M-270 Epoxy, Invitrogen). At room temperature, approximately $1\times10^7$ beads were coated with 5 µg of recombinant FAM19A5 protein by stirring, while rotating, the beads and the protein together for 20 hours at room temperature. Once the coating was done, the beads were washed 4 times with phosphate buffered saline (PBS) and blocked for one hour in PBS containing 3% BSA at room temperature. Then, the coated beads were cultured for two hours at room temperature with Phage-displayed scFv described above. To remove any phage that was not bound to the antigen coated beads, the beads were washed with 0.05% Tween20/PBS. Then the bound phages were eluted with 50 µL of 0.1M glycine/hydrogen chloride (0.1M Glycine-HCl, pH 2.2) and neutralized with 3 µL of 2M Tris with hydrogen chloride (tris-HCl, pH 9.1). This phage-containing supernatants were used to infect *E. coli* ER2738 cells and VCSM13 helper phage was used to amplify and rescue overnight. Also the input (input) and production (output) by phage titers from the phage-infected cultures were determined by blotting the phage-infected cultures on LB agar plates containing 50 µg/ml of kanamycin. The next day, PEG-8000 and NaCl were used to precipitate phages, which were used subsequently for bio-panning. Bio-panning was performed up to a total of five different times by repeating the above process. With each amplification, the phages were screened and selected for high affinity to the FAM19A5 protein.

Example 4 Selection of Clone by Phage ELISA

To analyze the clones selected from the bio-panning, we randomly selected individual clones from the phase-displayed scFv and confirmed using ELISA that the clones bind to the FAM19A5 recombinant protein. The FAM19A5 recombinant protein was diluted in 0.1 M $NaHCO_3$ buffer, and 100 ng/well of the protein was used to coat 96-well microtiter plates at 4° C. for 16 hours. Next day, the plates were blocked with 3% BSA/PBS at 37° C. for 1 hour. Then, the phage supernatant was mixed with 6% BSA/PBS and was cultured for 2 hours at 37° C. The plates containing the supernatant were then washed with 0.05% Tween-20/PBS. The HRP-conjugated M13 antibody (a-M13-HRP, Pierce Chemical Co, Rockford, Ill., USA) was diluted to 1/5000. 50 µl of the diluted antibody was added to the plates and incubated for 1 hour at 37° C. After the incubation and washing, the plates were added with 0.05 M citrate buffer solution, 1 µg/ml of 2,2'-azino-bis (3-ethylbenzothiazoline-6-sulphonic acid) (ABTS, Amresco, Solon, Ohio, USA), and 0.1% $H_2O_2$ for color development. The absorbance for each well was measured at 405 nm.

Figure 1B:
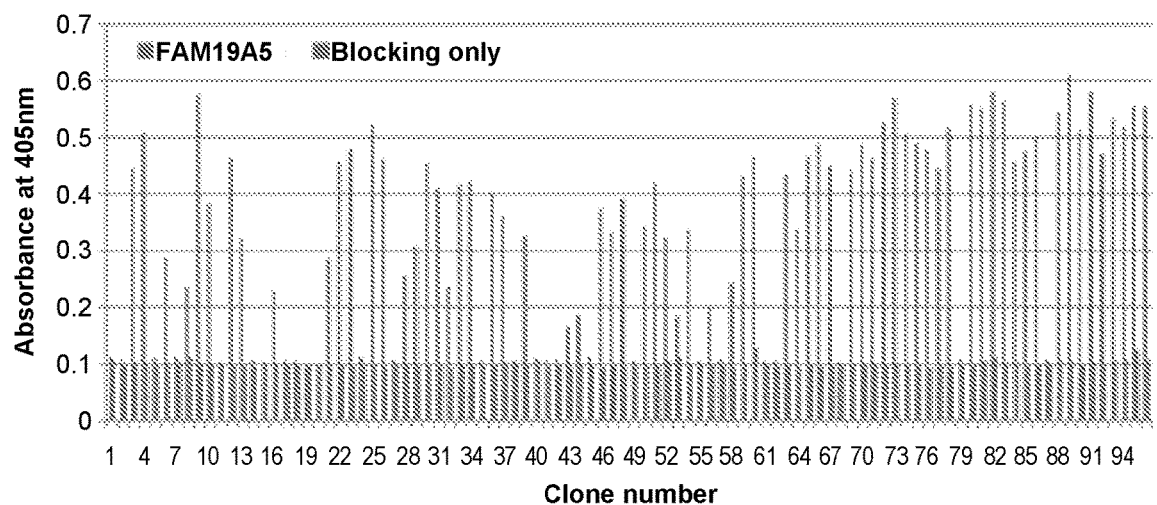
Figure 1C:
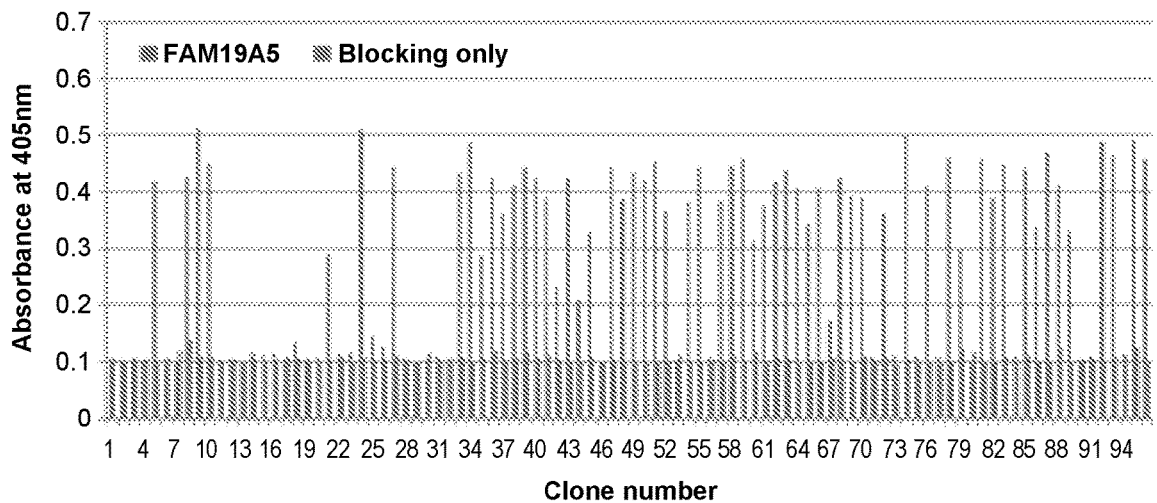

As shown in FIGS. 1A to 1C, we analyzed 24 clones generated from immunized chickens that bind to the FAM19A5 recombinant protein and show high absorbance. From these 24 clones, we obtained 13 scFv clones having unique sequences. For the clones generated from immunized rabbits (data not shown), 174 clones were initially identified with 164 clones being sequenced. From these clones, we obtained 22 final unique ScFv sequences were obtained.

Example 5 Production of Anti-FAM19A5-IgG2/4 Antibody

1. Sub-Cloning of Anti-FAM19A5 scFv into a Mammalian Expression Vector

Figure 2:
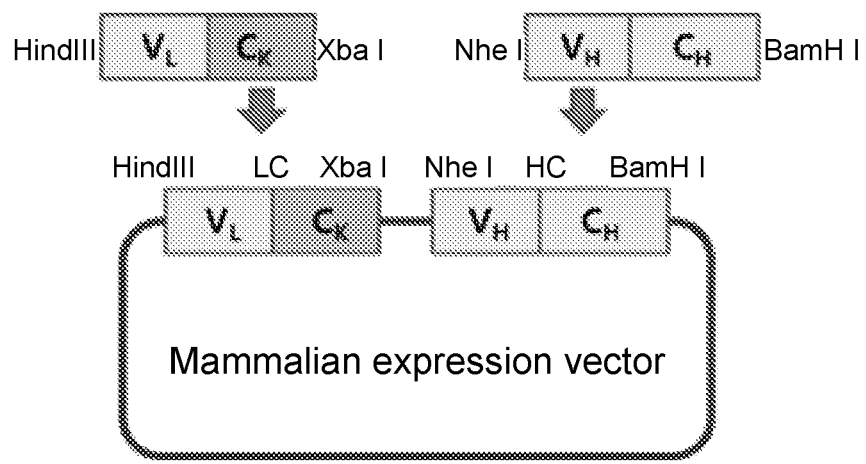
FIG. 2 shows the schematic diagram for subcloning of anti-FAM19A5 antibody (scFv) into a mammalian expression vector.

In the FAM19A5 scFv gene sequence, a human Cκ gene was connected to the light chain variable domain, and human immunoglobulin isotype IgG2/4 of CH1, CH2, and CH3 genes were connected to the heavy chain variable region. The antibody having each light chain and each heavy chain was synthesized by adding restriction sites (Genscript, USA). The synthesized gene was inserted into the mammalian cell expression vector having a modified restriction site to facilitate cloning. First, the light chain gene was inserted into the vector using Hind III and Xba I (New England Biolabs, UK) restriction enzymes and then adding the heavy chain gene to the vector by using NheI and BamHI (New England Biolabs, UK) restriction enzymes (FIG. 2).

2. Purification of the Anti-FAM19A5 Antibody

Figure 3:
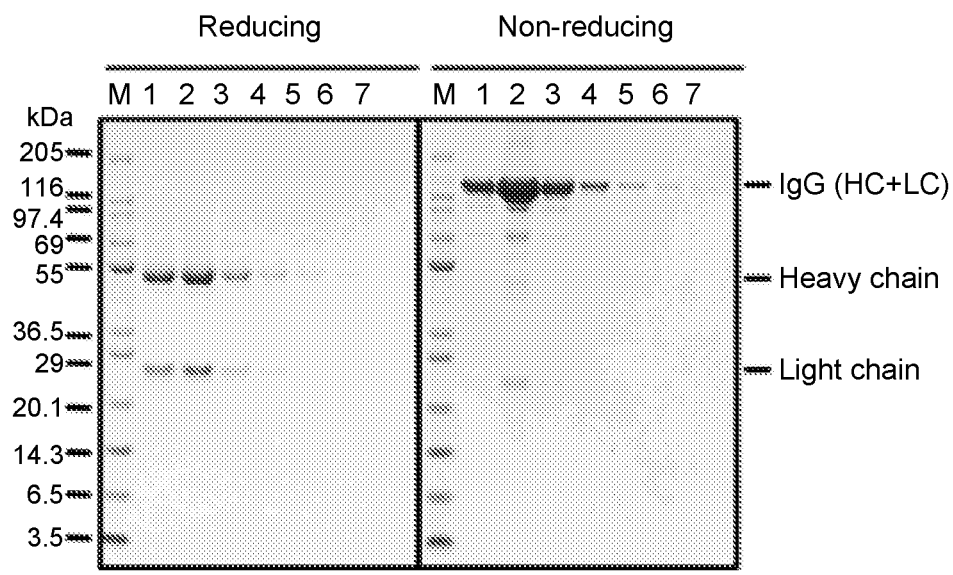
FIG. 3 shows SDS-PAGE results of the chimeric anti-FAM19A5-IgG2/4 monoclonal antibody (1-65). The left panel shows a reducing SDS-PAGE, and the right panel shows a non-reducing SDS-PAGE.
Figure 4:
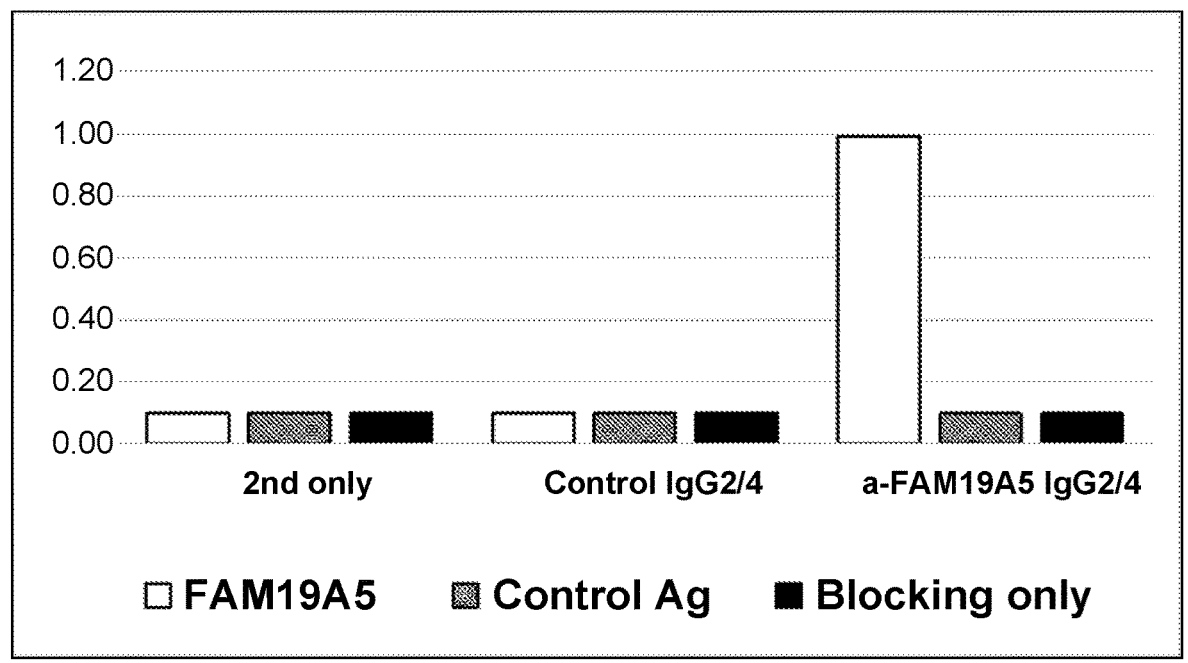
FIG. 4 shows that chimeric anti-FAM19A5-IgG2/4 monoclonal antibody (1-65) specifically binds to human FAM19A5.

In order to express and purify an anti-FAM19A5-IgG2/4 antibody, we used a mammalian cell transfection and over-expression injection system. We mixed 2 µg/ml of the mammalian expression vector with 4 µg of polyethyleneimine (PEI, Polysciences, Warrington, Pa., USA) in 150 mM sodium chloride (NaCl, Merck) corresponding to ⅒ of the cell culture volume. The mixture was allowed to stand for 15 minutes at room temperature. The mixture was added to HEK293F cells ($2\times10^6$ cells/ml, Invitrogen), which were then incubated in the FREESTYLE™ 293 expression culture medium containing 100 U/ml of penicillin and streptomycin (Invitrogen) at 7% $CO^2$ and 37° C. and in a stirring condition of 135 rpm for six days. To purify the expressed anti-FAM19A5 IgG2/4 antibodies from the cell culture supernatant, we used Protein A bead (RepliGen, Waltham, Mass., USA) affinity gel chromatography. The protein A chromatography purified antibody was run on 4~12% Bis-Tris gradient gel electrophoresis. The size and yield of the protein was confirmed by the Coomassie Brilliant Blue staining (FIG. 3).

Example 6 Verification of Anti-FAM19A5-IgG2/4 Antibody Specificity

Figure 5A:
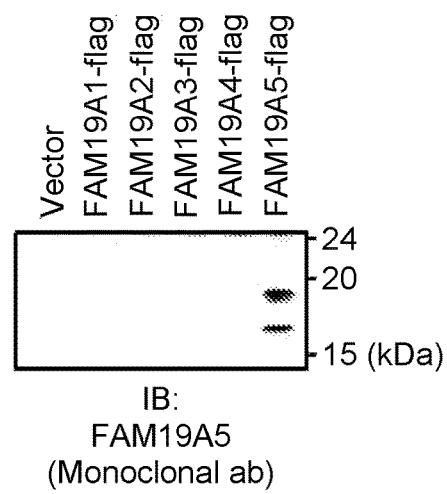
FIG. 5A shows that the chimeric anti-FAM19A5-IgG2/4 monoclonal antibody (1-65) is specific to FAM19A5 protein, but does not bind to other proteins in the FAM19A subfamily.
Figure 5B:
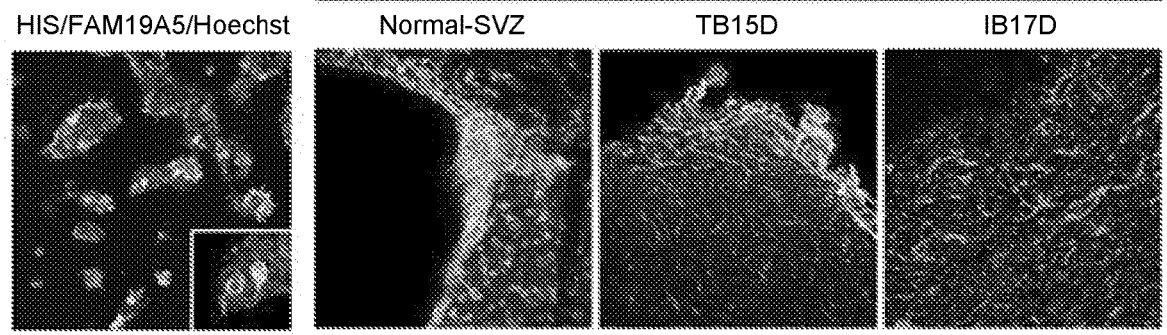
FIG. 5B shows immunocytochemistry (ICC, left panel) and immunohistochemistry (IHC, right three figures) analyses for FAM19A5 expression. ICC results show that chimeric anti-FAM19A5-IgG2/4 monoclonal antibody (1-65) binds to FAM19A5 protein that is conjugated with His-tag. IHC results show that FAM19A5 proteins are expressed in GFAP protein-expressing cells of the subventricular zone of normal mice (left) and at the damaged penumbra of the mouse with traumatic brain injury for 5 days (TBI5D, middle) and at the damaged penumbra of the rat with ischemic brain injury for 7 days (IBI7D, right).

HEK293T cells stably transfected with genes encoding the FAM19A family of proteins were lysed in buffer containing 50 mM Tris-HCL (pH 6.8), 2% SDS, 10% glycerol, 100 mM mercaptoethanol, and bromophenol blue. Whole-cell extracts were resolved on SDS-polyacrylamide (PAGE) gels and transferred to nitrocellulose blotting membranes in a Bio-Rad Trans-Blot electrophoresis apparatus (Hercules, Calif., USA). The blots were blocked in Tris-buffered saline containing 0.3% Tween 20 and 5% skim milk, and incubated with anti-FAM19A5 antibody at room temperature for 3 h. They were then washed three times with TBS/0.3% Tween 20. Antibody binding was subsequently detected by incubation with secondary antibodies linked to horseradish peroxidase (Jackson ImmunoResearch Laboratories, West Grove, Pa., USA). The blots were washed three times, and immunoreactive bands were visualized by exposure to X-ray film for 0.5 or 10 min, after application of GE healthcare ECL reagents (Buckinghamshire, UK). The result show that the anti-FAM19A5 antibody 1-65 specifically bind to FAM19A5 protein that is conjugated with flag-tag but not to other FAM19A subfamily proteins (FIG. 5A) For immunocytochemical analysis, HEK293 cells expressing FAM19A-family proteins were fixed with 4% PFA. Cells were then blocked with 3% BSA and 0.1% Triton X-100 in PBS for 30 min at room temperature. Primary antibody (the anti-FAM19A5 antibody 1-65) was applied overnight at 4° C. After several washes with PBS, appropriate secondary antibodies were applied for 30 min. Subsequently, the cells were washed, mounted, and observed under a fluorescence or confocal microscope (LSM700; Zeiss, Goettingen, Germany). Nuclei were stained with Hoechst 33342. Immunocytochemical analysis of His-tagged FAM19A5 expressed in HEK293T cells exhibited that the anti-FAM19A5 antibody 1-65 specifically bind to FAM19A5 protein that is conjugated with His-tag (FIG. 5B, left panel).

Example 7 Epitope Mapping Analysis Using FAM19A5 Epitope Fragments F1-F6

Figure 9:
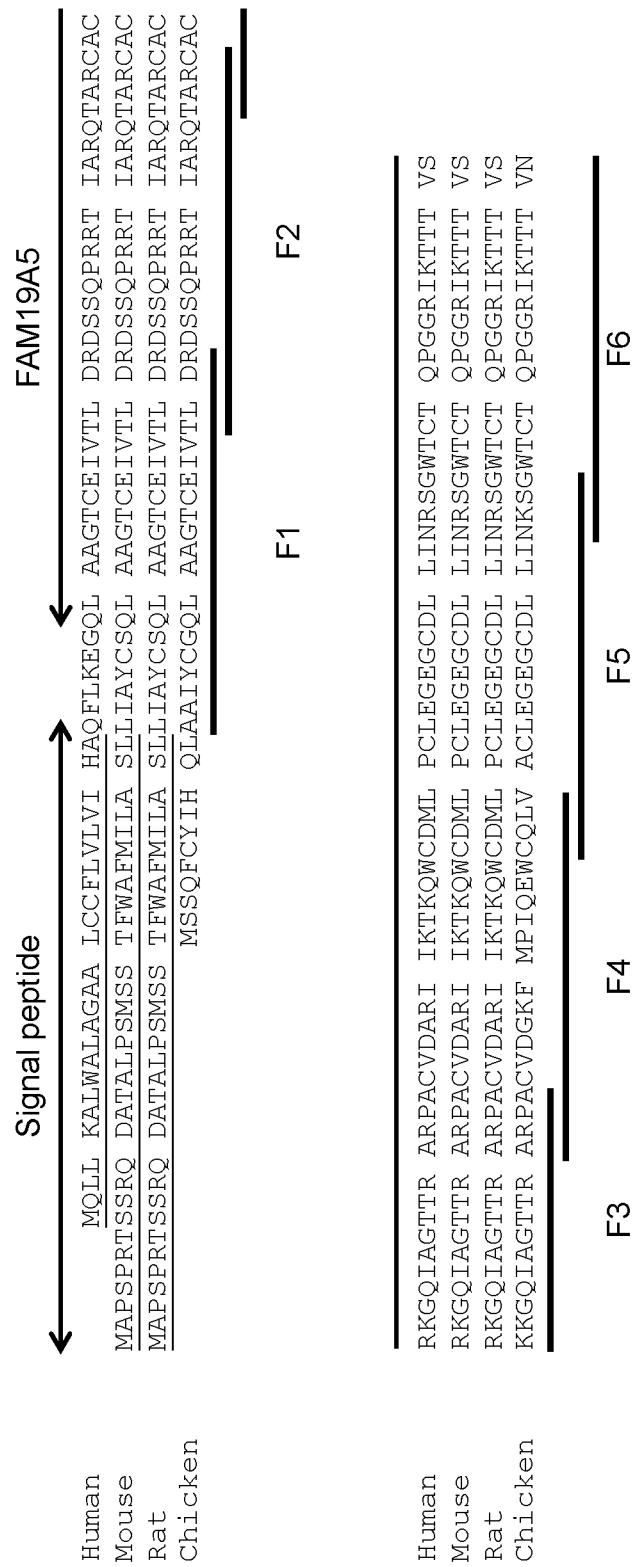
FIG. 9 shows an alignment of FAM19A5 amino acid sequences of different species (i.e., human, mouse, rat, and chicken). Fragments F1-F6, which were used for the epitope mapping analysis, are indicated. The signal peptides are underlined.

Overlapping peptide fragments (F1-F6, see FIG. 9) of the human FAM19A5 protein were synthesized and conjugated to BSA. Binding of the different anti-FAM19A5 antibodies to the BSA-conjugated peptide fragments F1-F6 was determined by Western blot analysis or ELISA assay. For the Western blot analysis, BSA-conjugated FAM19A5 fragments F1-F6 were separated by SDS polyacrylamide gel electrophoresis and transferred to a nitrocellulose membrane by the standard procedure. The membrane was incubated with the anti-FAM19A5 antibody (e.g., 1-65, 2 µg/ml, 1-65-scFv-rabbit Fc-SSS), and the antigen-antibody complexes were detected with the appropriate secondary antibody conjugated with horse-radish peroxidase (anti-rabbit IgG (Fc specific)-HRP, 1:4000 dilution). For the ELISA assay, the following protocol was used. FAM19A5 fragment F1-F6 (diluted to 1 µg/mL in 50 mM carbonate buffer (Biosesang) or to 20 µg/mL for high concentration analysis) were used to coat the wells of 96-well immuno plates (Thermo Scientific) (100 µL/well) overnight at 4° C. and then subsequently washed twice in 1×PBS. The plates were then blocked with the blocking buffer (100 µL/well) for 1 hour at room temperature. During the 1-hour incubation, the relevant anti-FAM19A5 antibodies were diluted to 1 µg/mL (or 20 µg/mL for high concentration analysis) in the diluent buffer. Once the plates were washed (2× using 1×PBS), the diluted anti-FAM19A5 antibodies were added to the appropriate wells, and the plates were incubated at room temperature for 1 hour. The plates were subsequently washed for a total of five times using the washing buffer. Next, the ODP substrate (prepared by dissolving one ODP tablet (0-phenylenediamine Dihydrochloride, Thermo) into 9 mL of sterilized deionized water and 1 mL of 10× stable Peroxide Stable buffer (Theromo)) was added to each of the wells, and the color change reaction was allowed to occur for 10 minutes. This reaction was stopped by adding 100 µL of 2N H2SO4 (Daejung) to the wells. The absorption value of each of the wells was detected at 492 nm using a 96-well microplate reader (Molecular Device).

Figure 11:
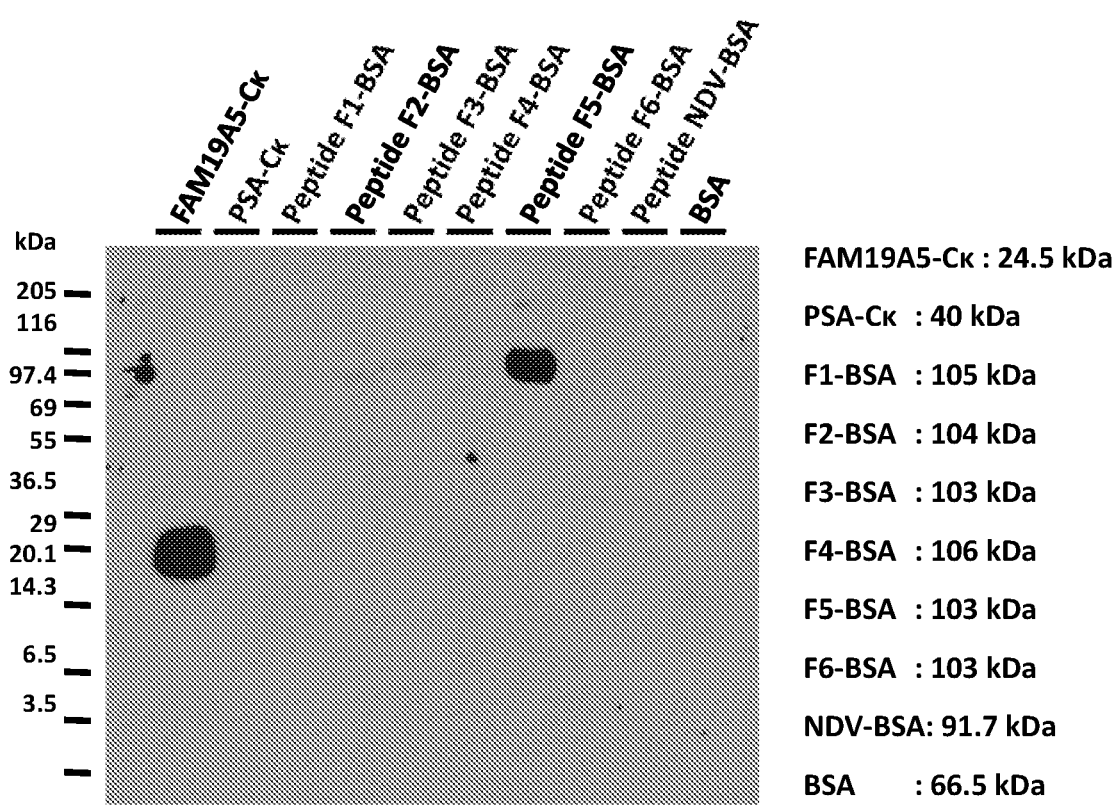
FIG. 11 shows Western blot results for the binding of monoclonal antibody clone 1-65 to epitope fragments F1 to F6 (lanes 3-8, respectively). FAM19A5-Cκ (lane 1), PSA-Cκ (lane 2), Peptide NDV-BSA (lane 9), and BSA (lane 10) were used as controls. The respective sizes of the different antigens used are shown to the right of the blot. The amount of antigen used per well is 300 ng. The primary antibody used for the Western blot is 1-65-scFv-rabbit-Fc-SSS (2 μg/ml), and the secondary antibody used for the experiment is anti-Rabbit IgG (Fc specific)-HRP (1:4000).
Figure 12A:
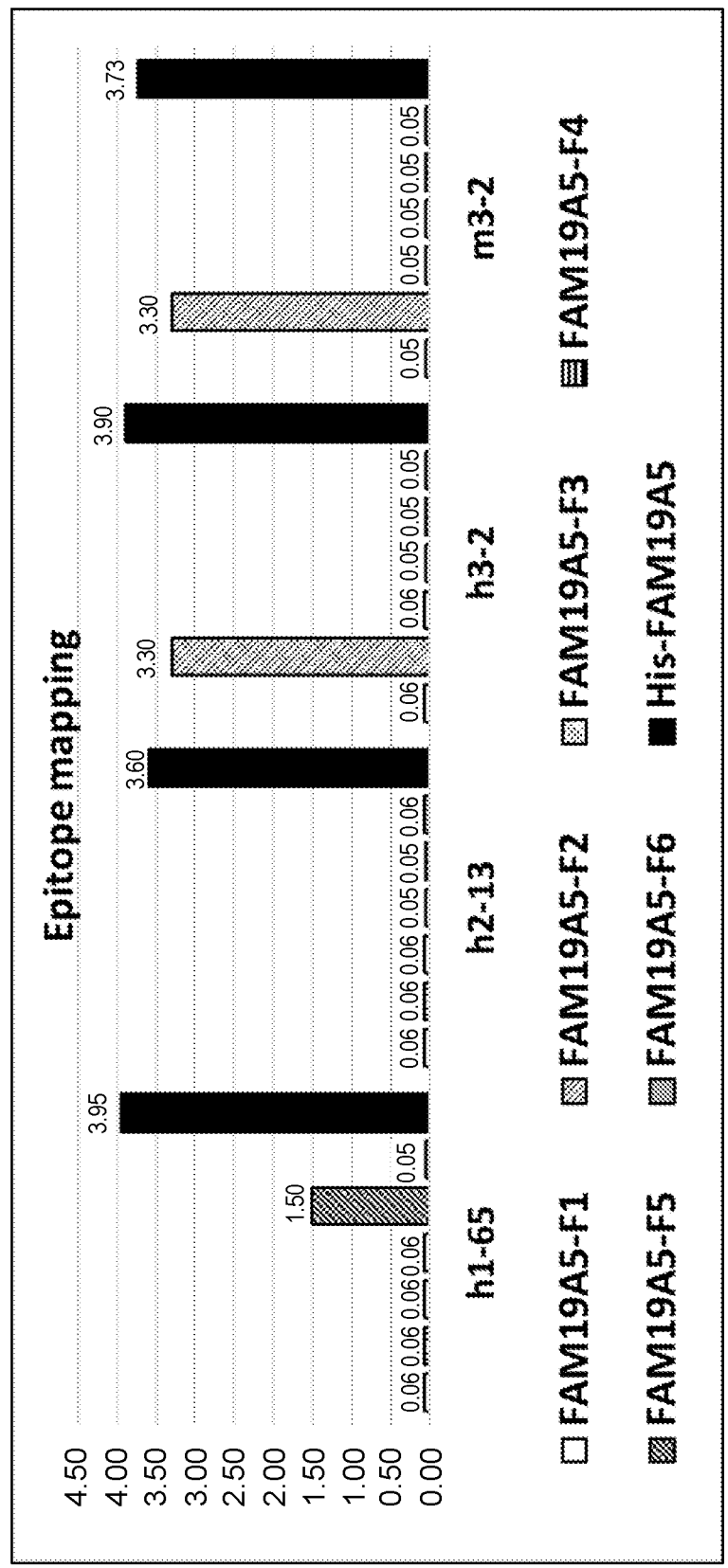
FIGS. 12A and 12B show ELISA results for the binding of several anti-FAM19A5 antibodies to epitope fragments F1 to F6.
Figure 12B:
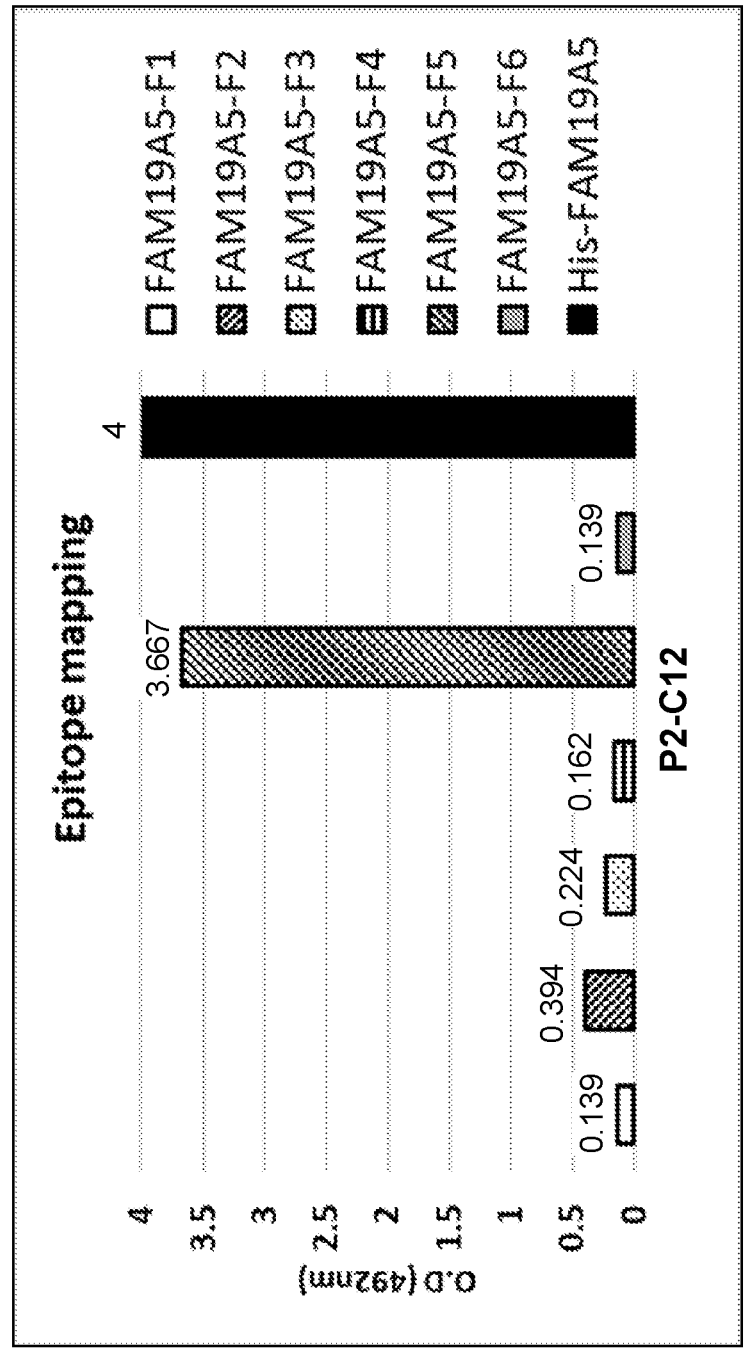

As shown in FIGS. 11A and 12A, the anti-FAM19A5 antibody 1-65 bound strongly to fragment F5 as measured by both Western Blot and ELISA assay, respectively. The anti-FAM19A5 antibody P2-C12 also bound the epitope fragment F5 strongly but not significantly to the other fragments (F1-F4 and F6) (see FIG. 12B). The anti-FAM19A5 antibody 3-2, on the other hand, did not bind to fragment F5. Instead, the 3-2 antibody bound strongly to epitope fragment F2 with minimal binding to the other fragments (see FIG. 12A). This was also true for the anti-FAM19A5 1-28 antibody (data not shown). However, in contrast to the other antibodies, the anti-FAM19A5 antibody 2-13 did not appear to bind to any of the epitope fragments (see FIG. 12A).

Next, to identify the specific amino acid residues within the epitope fragment F5 that the 1-65 and P2-C12 antibodies bind to, different amino acid residues of the F5 fragment were replaced with alanine as shown in Table 9 (below). The mutated residues are bolded and underlined. The binding affinity of the indicated anti-FAM19A5 antibodies were measured using an ELISA assay as described above.

TABLE 9

| Mutant peptide (#) | Sequences |
|---|---|
| F5 | SDMLPSLEGEGSDLLINRSG (SEQ ID NO: 125) |
| F5-1 (#1) | SDMLPSLEGRASDLLINRSG (SEQ ID NO: 126) |
| F5-2 (#2) | SDMLPSLEGEGSALLINRSG (SEQ ID NO: 127) |
| F5-3 (#3) | SDMLPSLEGEGSDALINRSG (SEQ ID NO: 128) |
| F5-4 (#4) | SDMLPSLEGEGSDLLANRSG (SEQ ID NO: 129) |
| F5-5 (#5) | SDMLPSLAGEGSDLLINRSG (SEQ ID NO: 130) |
| F5-6 (#6) | SDMLPSLEGAGSDLLINRSG (SEQ ID NO: 131) |
| F5-7 (#7) | SDMLPSLEGEGSDLLIARSG (SEQ ID NO: 132) |
| F5-8 (#8) | SDMLPSLEGEGSDLLINASG (SEQ ID NO: 133) |

Figure 13A:
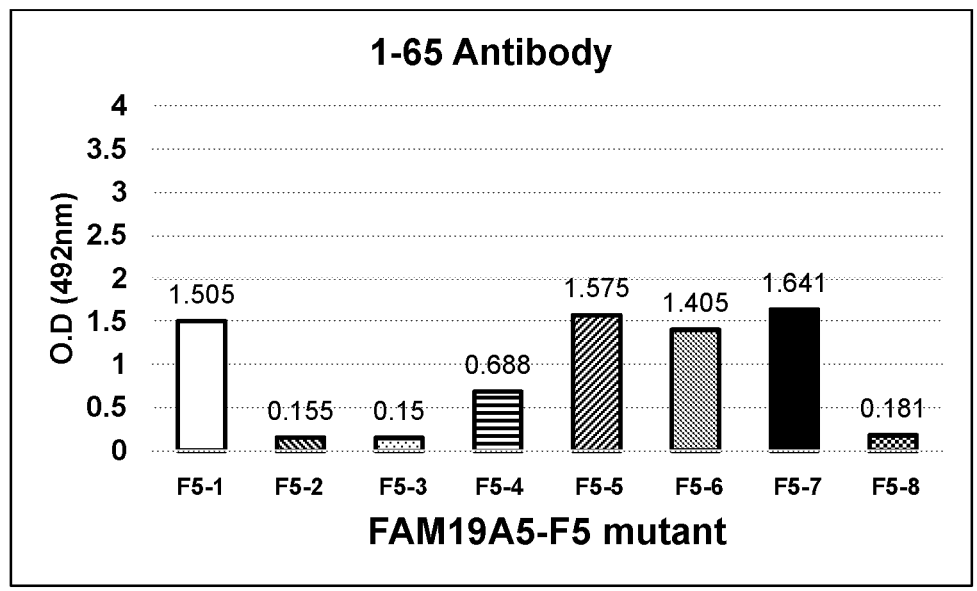
FIGS. 13A and 13B show the ELISA results for the binding of anti-FAM19A5 antibodies 1-65 (FIG. 13A) and P2-C12 (FIG. 13B) to eight different FAM19A5 fragment 5 mutant peptides (F5-1 to F5-8). The exact O.D. value are indicated at the top of each bar.
Figure 13B:
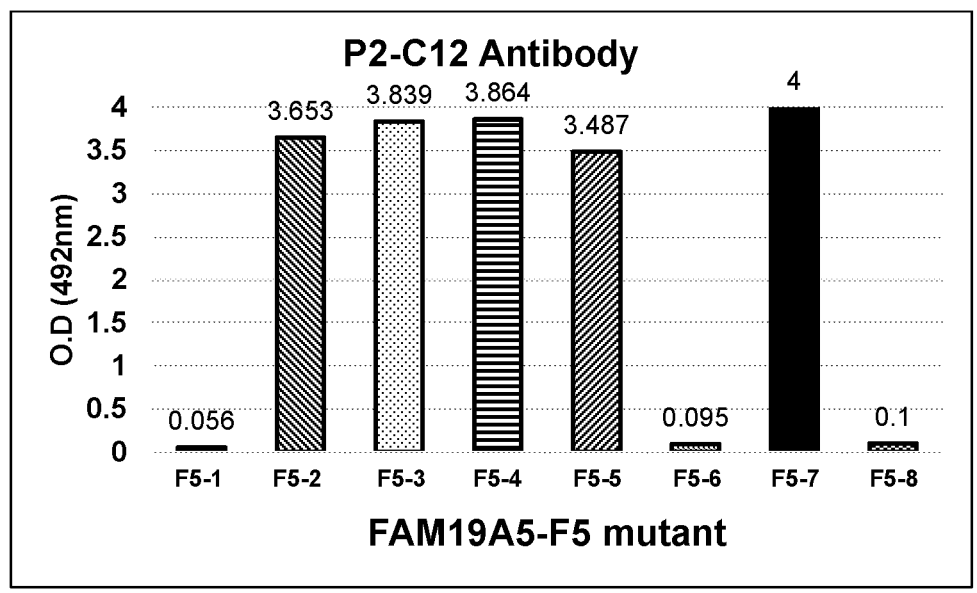
Figure 14:
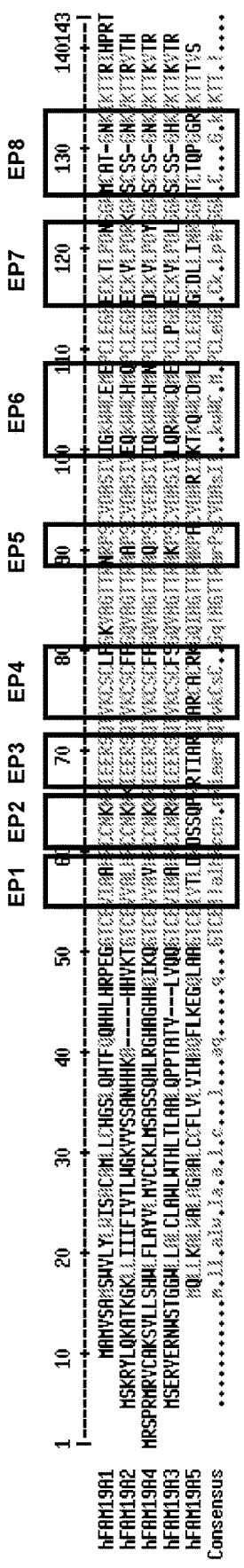
FIG. 14 shows an amino acid sequence alignment of the different members of the FAM19A family (i.e., FAM19A1-5). The regions with the greatest amino acid diversity among the members are boxed and shown as EP1 to EP8.
Figure 15A:
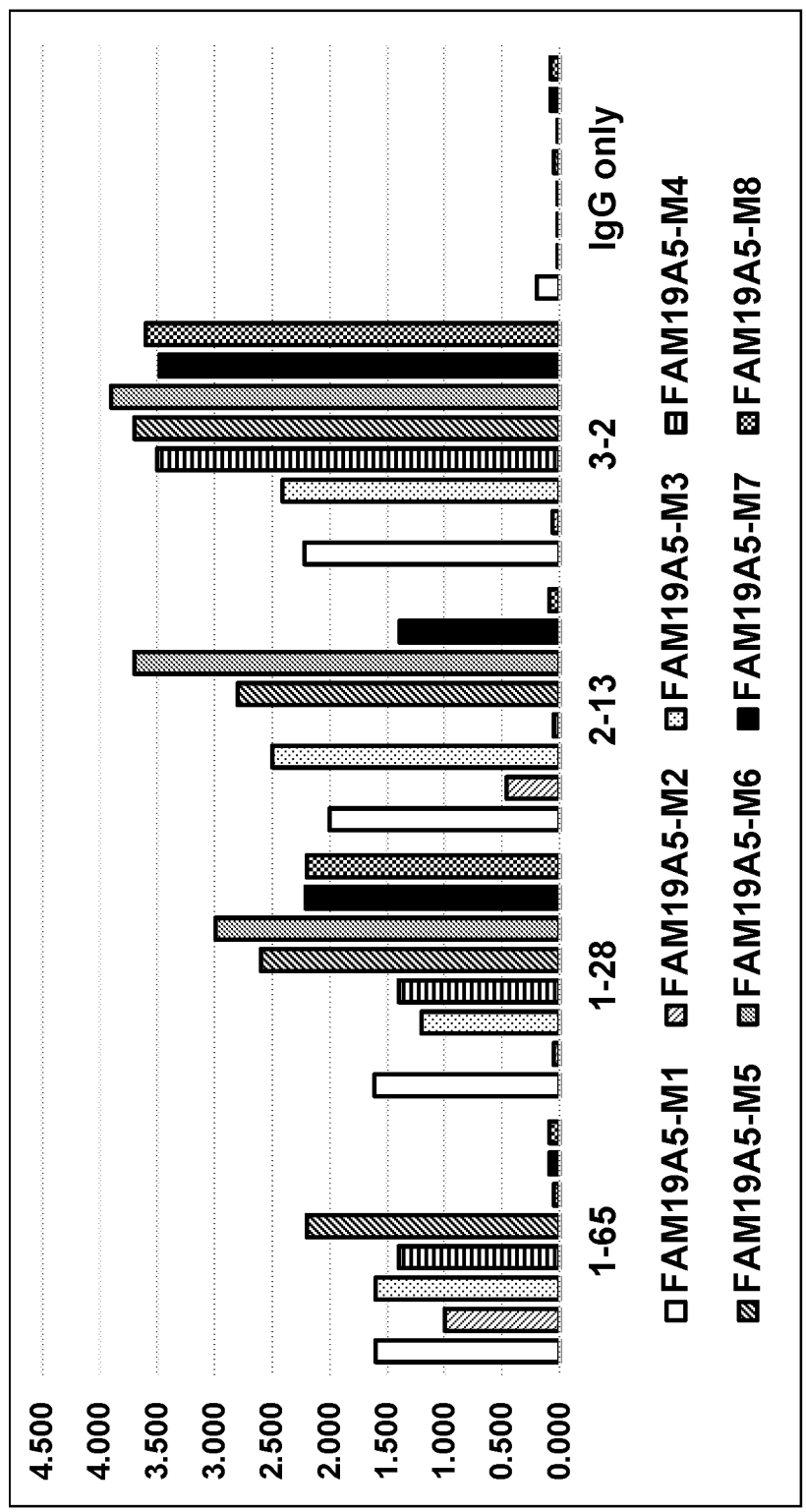
FIGS. 15A to 15C show the ELISA results for the binding of different anti-FAM19A5 antibodies to FAM19A5 mutants M1 to M8.
Figure 15B:
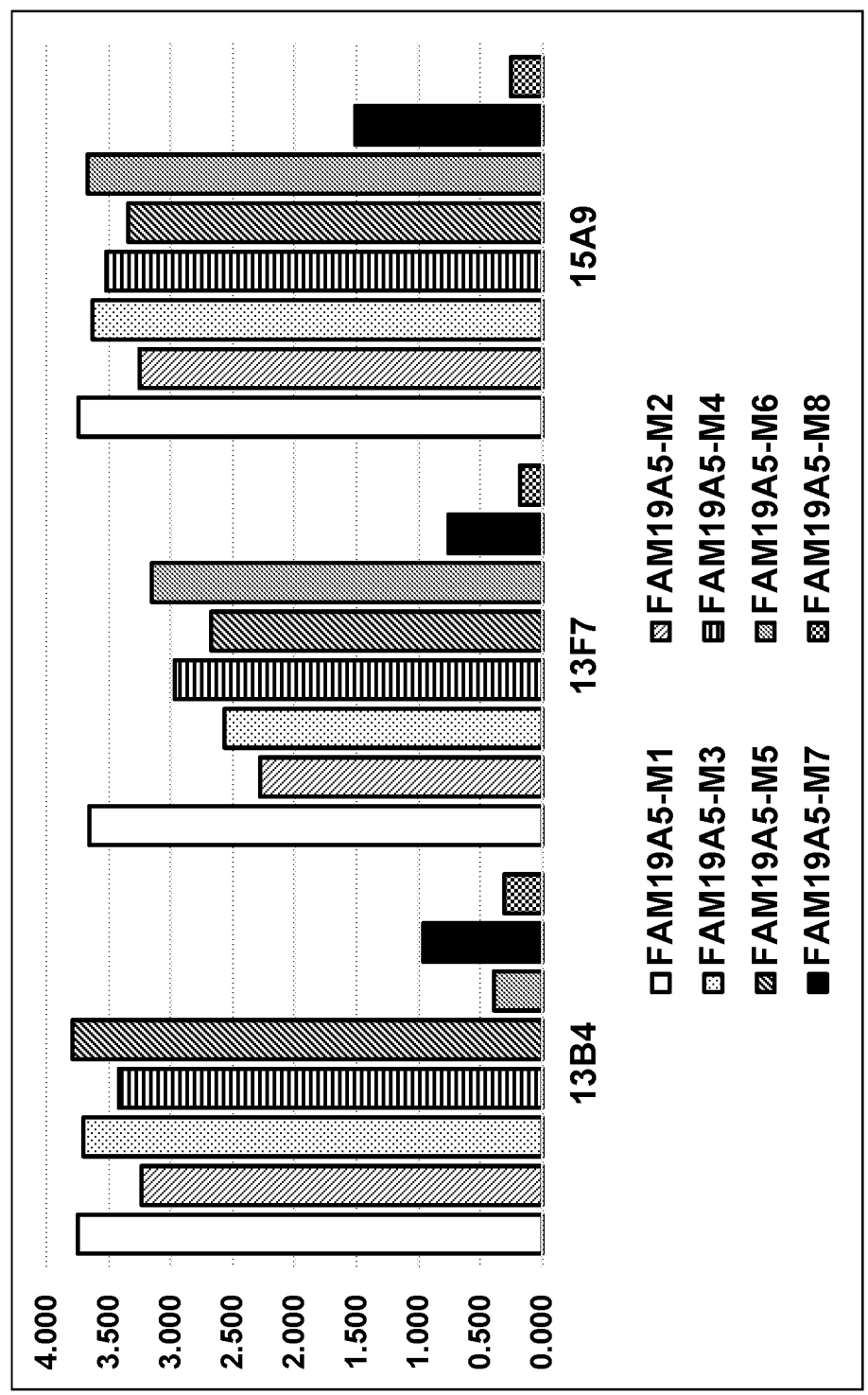

Double underline: Cysteine is reactive in peptide synthesis process so it was replaced with serine to reduce reactivity. Serine was substituted as its structure is the most closest to cysteine. Such replacements are indicated as double underlines As shown in FIG. 13A, the 1-65 antibody was able to bind mutant peptides #1, 5, 6, and 7 with similar affinity. However, when amino acid residues D13, L14, I16, and R18 of fragment F5 were mutated to alanine (numbering based on SEQ ID NO: 125 in Table 9, above), the 1-65 antibody was no longer able to bind the peptide fragment, suggesting that these amino acid residues were important binding sites for the 1-65 antibody. In contrast, the P2-C12 antibody showed high binding to mutant peptides #2, 3, 4, 5, and 7 but not to mutant peptides #1, 6, and 8. See FIG. 13B. As shown in Table 9 (above), the mutant peptides #1, 6, and 8 comprise an alanine substitution at amino acid residues G11, E10, and R18 (numbering based on SEQ ID NO: 125), suggesting that these amino acid residues are important binding sites for the P2-C12 antibody.

Example 8 Epitope Mapping Analysis Using FAM19A5 Mutants M1-M8

To further characterize the binding epitopes of the anti-FAM19A5 antibodies disclosed in the present disclosure, the amino acid sequences for the different FAM19 family members (i.e., FAM19A1-5) were aligned as shown in FIG. 14. Based on this alignment, eight regions where the amino acid sequences of the FAM19A5 protein differed the most significantly from the other members of the FAM19A family (i.e., FAM19A1-4) were identified (M1-M8). The amino acid sequences of these regions were replaced with the consensus sequence of the corresponding regions for the FAM19A1-4 proteins. See Table 10 (the mutated amino acid residues are bolded and underlined).

TABLE 10

| FAM19A5 | Sequences |
|---|---|
| Wild Type | QFLKEGQLAAGTCEIVTLDRDSSQPRRTIARQTARCACRKGQIAGTTRARPACVDARIIKTKQWCDMLPCLEGEGCDLLINRSGWTCTQPGGRIKTTTVS (SEQ ID NO: 142) |
| M1 | QFLKEGQLAAGTCEVIAAHRDSSQPRRTIARQTARCACRKGQIAGTTRARPACVDARIIKTKQWCDMLPCLEGEGCDLLINRSGWTCTQPGGRIKTTTVS (SEQ ID NO: 95) |
| M2 | QFLKEGQLAAGTCEIVTLDRCCNKNRRTIARQTARCACRKGQIAGTTRARPACVDARIIKTKQWCDMLPCLEGEGCDLLINRSGWTCTQPGGRIKTTTVS (SEQ ID NO: 96) |
| M3 | QFLKEGQLAAGTCEIVTLDRDSSQPRIEERSQTARCACRKGQIAGTTRARPACVDARIIKTKQWCDMLPCLEGEGCDLLINRSGWTCTQPGGRIKTTTVS (SEQ ID NO: 97) |
| M4 | QFLKEGQLAAGTCEIVTLDRDSSQPRRTIARQTVKCSCFPGQIAGTTRARPACVDARIIKTKQWCDMLPCLEGEGCDLLINRSGWTCTQPGGRIKTTTVS (SEQ ID NO: 98) |
| M5 | QFLKEGQLAAGTCEIVTLDRDSSQPRRTIARQTARCACRKGQIAGTTRNKPSCVDARIIKTKQWCDMLPCLEGEGCDLLINRSGWTCTQPGGRIKTTTVS (SEQ ID NO: 99) |
| M6 | QFLKEGQLAAGTCEIVTLDRDSSQPRRTIARQTARCACRKGQIAGTTRARPACVDARIILQRWWCQMELCLEGEGCDLLINRSGWTCTQPGGRIKTTTVS (SEQ ID NO: 100) |
| M7 | QFLKEGQLAAGTCEIVTLDRDSSQPRRTIARQTARCACRKGQIAGTTRARPACVDARIIKTKQWCDMLPCLEGEECKTLPDNSGWTCTQPGGRIKTTTVS (SEQ ID NO: 101) |
| M8 | QFLKEGQLAAGTCEIVTLDRDSSQPRRTIARQTARCACRKGQIAGTTRARPACVDARIIKTKQWCDMLPCLEGEGCDLLINRSGWTCSCSSGNKIKTTTVS (SEQ ID NO: 102) |

The mutant FAM19A5-expressing phages were prepared as follows. To prepare the media for phage culture, 55.6 ml of 2M Glucose(D-(+)-Glucose, Sigma), 5 mL of 1M MgCl2 (Magnesium chloride, Junsei) 1 mL of 34 mg/mL chloramphenicol (Sigma) were added to 2×YT media. Colonies obtained through mono-phage ELISA were selected and placed in 5 mL of prepared media (2×YT-GMC) to be cultured for 16 hours at 37° C. with shaking incubator (VS-8480, Vision). 100 μL of each culture was transferred to 10 mL 2×YT-GMC individually which were cultured at 37° C. in the incubator until detection value at O.D. 600 nm reached 0.5. Once detection value has reached 0.5 at O.D. 600 nm, 5 mL of each culture were obtained as samples to be infected. Following sample preparation, 50 μL of M1 helper phage was added to individual samples then incubated at 37° C. without shaking for 30 minutes and with shaking for additional 30 minutes. Individual cultures were centrifuged for 15 minutes at 3,850 rpm using Micro centrifuge (Micro12, Hanil). The supernatants of centrifuged cultures were removed to be kept separate and replaced with 5 mL of 2×YT media containing 1 mL of 1M IPTG (AG Scientific), 5 mL of 1M MgCl2.1 ml of 70 μg/μL kanamycin (Biopure) and 1 mL of Chloramphenicol. The resulting pellets were dispersed thoroughly in newly added media followed by incubation at 30° C. for 16 hours with stirring.

As shown in FIG. 15A and in agreement with the earlier data described in Example 7, the anti-FAM19A5 antibody 1-65 failed to bind to FAM19A5 mutants M6, M7, and M8. The M6 and M7 mutants comprise amino acid mutations at sites that correspond to regions within epitope fragment F5 of FAM19A5. See Table 10 (above).

Epitope analysis for additional anti-FAM19A5 antibodies are provided in FIGS. 15B and 15C. Anti-FAM19A5 antibodies 13B4, 13F7, and 15A9 all failed to bind to FAM19A5 mutant M8 and had reduced binding to mutant M7. The 13B4 antibody additionally failed to bind to FAM19A5 mutant M6. See FIG. 15B. Similarly, antibodies P1-A08, P1-F02, P2-A01, P2-A03, P2-F07, and P2-F11 all failed to bind to FAM19A5 mutant M8 with many of the antibodies also having reduced to no binding to mutant M7. The P2-C12 antibody differed from these antibodies by strongly binding to FAM19A5 mutant M8. Instead, the P2-C12 antibody failed to bind to FAM19A5 mutant M6, which is in agreement with the earlier data demonstrating that epitope fragment F5 comprises important FAM19A5 binding sites for the P2-C12 antibody.

Example 9 Cross-Competition Analysis

Next, a two-site sandwich ELISA was used as described below to assess whether the different anti-FAM19A5 antibodies with similar binding epitopes cross-compete with each other. See FIG. 16A.

First, the indicated anti-FAM19A5 antibodies were diluted in 1×PBS to a concentration of 10 µg/mL. The diluted anti-FAM19A5 antibodies (10 µg/mL in 1×PBS) ("capture antibody") were used to coat the 96-well plates (100 µL/well) at 37° C. for approximately 1 hour. After the incubation, the plates were washed with the washing buffer (0.01% Tween-20/PBS; also called 0.01% PBST) for a total of five washes, blocked with the blocking solution (5% BSA/PBS; also called 5% PBSA) (250 µL/well) for one hour at 37° C., and then washed again. Next, 100 µg/mL of the FAM19A5 antigen (diluted in PBS containing 5% BSA, 0.01% Tween-20; also called 5% PBSAT; "diluent buffer") was added to each of the wells, and the 96-well plates were incubated for 2 hours at 37° C. After the incubations, the plates were washed using 0.01% PBST for a total of five washes. After the final wash, the indicated biotinylated anti-FAM19A5 antibodies ("detection antibody") (diluted to 1 µg/mL in 5% PBSAT) were added to the relevant wells (100 µL volume) and the plates were incubated for an additional 1 hour at 37° C. Afterwards, the plates were washed again with 0.01% PBST (five total washes). Next, 100 µL of the diluted (1/2000 in 5% PBSAT) Streptavidin-HRP (1 mg/mL, Sigma, USA) was added to the wells, and the plates were incubated for 30 minutes at room temperature. The plates were then washed and treated with 100 µL of the TMB substrate (3,3plates were then washed and treated with 100 µLution, Thermo Fisher Scientific). After an additional 30-minute incubation at room temperature, the color change reaction was induced by the addition of the TMB substrate. This reaction was stopped using 50 µL of sulfuric acid (2N $H_2SO_4$), and the extent of color change was detected via absorption at 450 nm with reference wavelength at 620 nm using a 96 well microplate reader (Molecular Device).

Figure 15C:
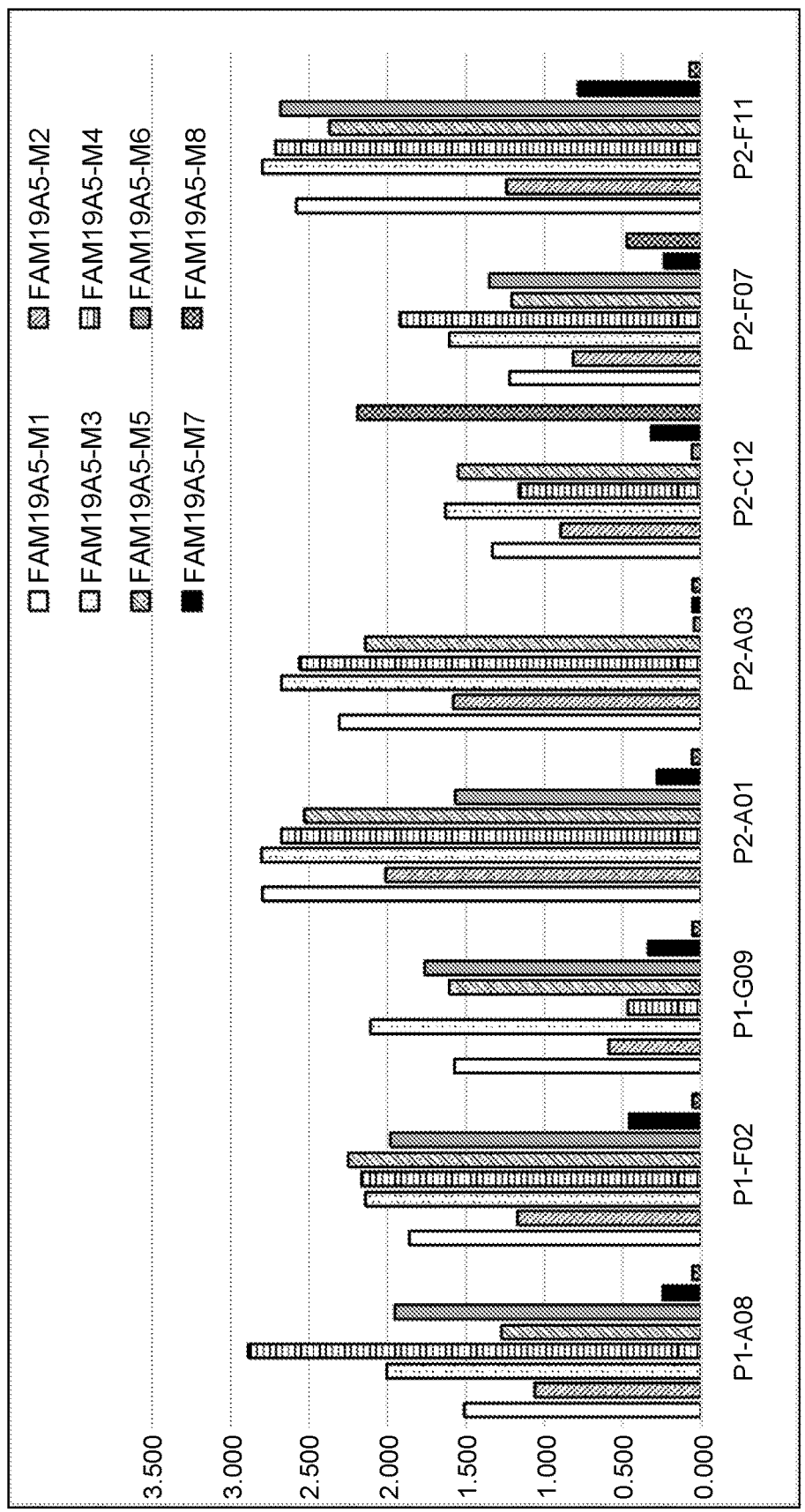
Figures 16A, 16B:
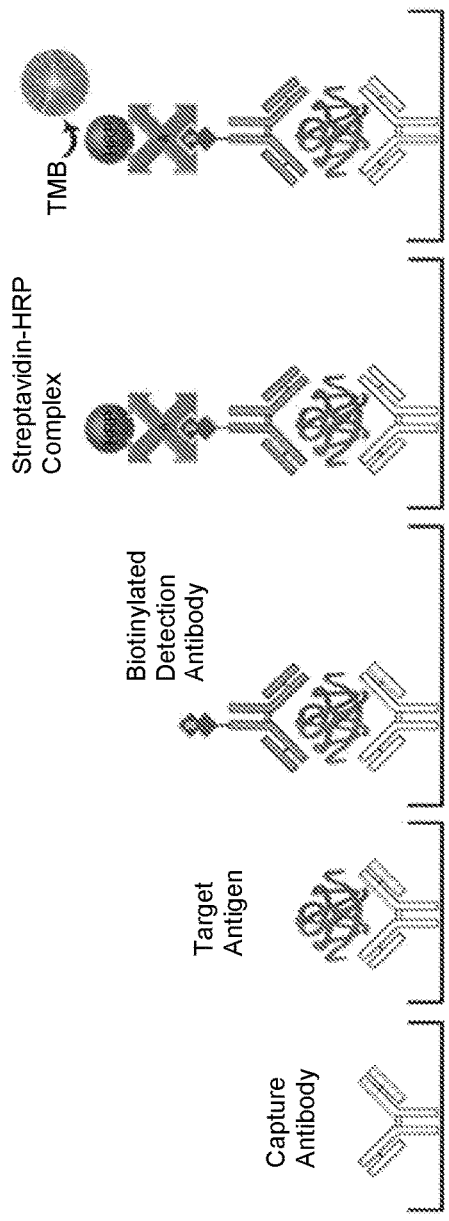
FIG. 16A shows the schematic diagram of the two-site sandwich ELISA assay used to assess cross-competition among the different anti-FAM19A5 antibodies.
FIG. 16B shows the results of the cross-competition analysis for six different anti-FAM19A5 antibodies: 1-65, P2-A03, P2-F11, 13B4, 2-13, and 3-2. The term "S/N" refers to the signal to noise ratio, which is measured as follows: [O.D. of 10 ng/mL antigen]/[O.D. of 0 ng/mL antigen]. The grey boxes shows cross-competition (i.e., S/N ratio lower than 2).
Figure 17A:
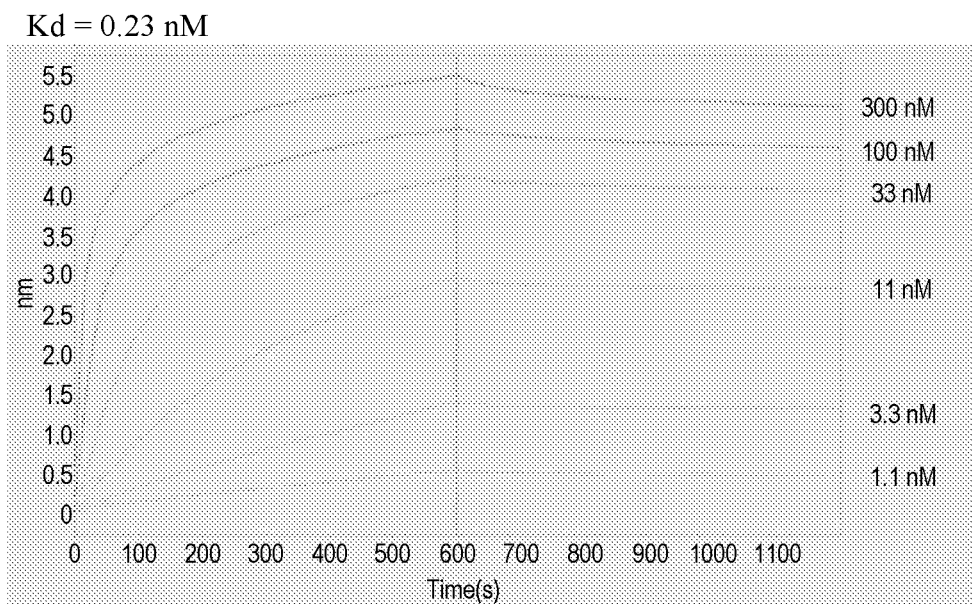
FIGS. 17A to 17D show the OCTET test results for the binding of antibody 1-65 (FIG. 17A), 13B4 (FIG. 17B), 13F7 (FIG. 17C), and 15A9 (FIG. 17D) to FAM19A5. The Kd value is also shown for each of the antibodies.
Figure 17B:
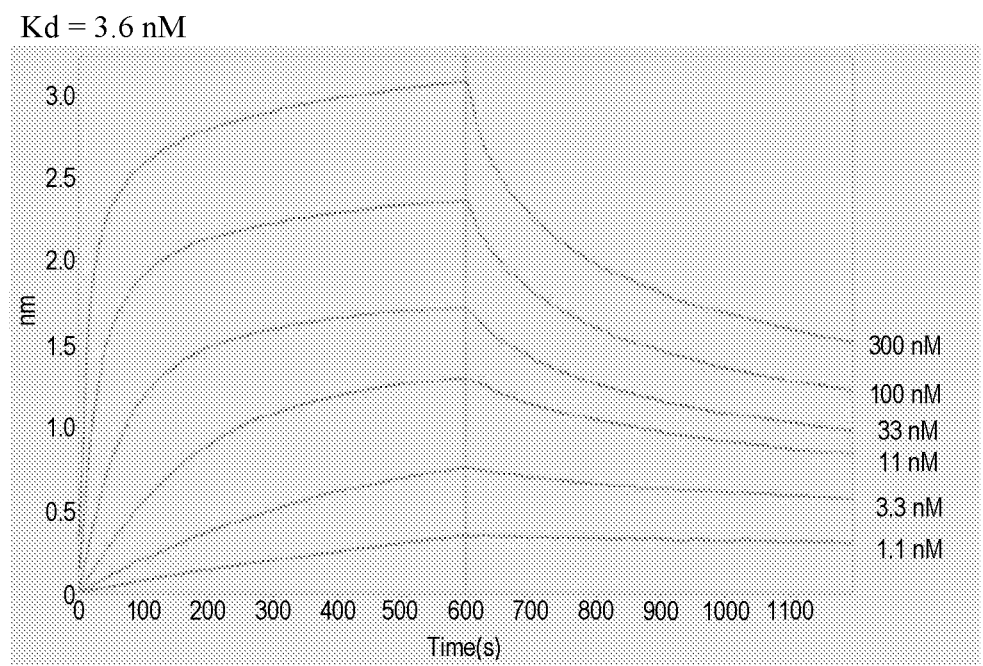
Figure 17C:
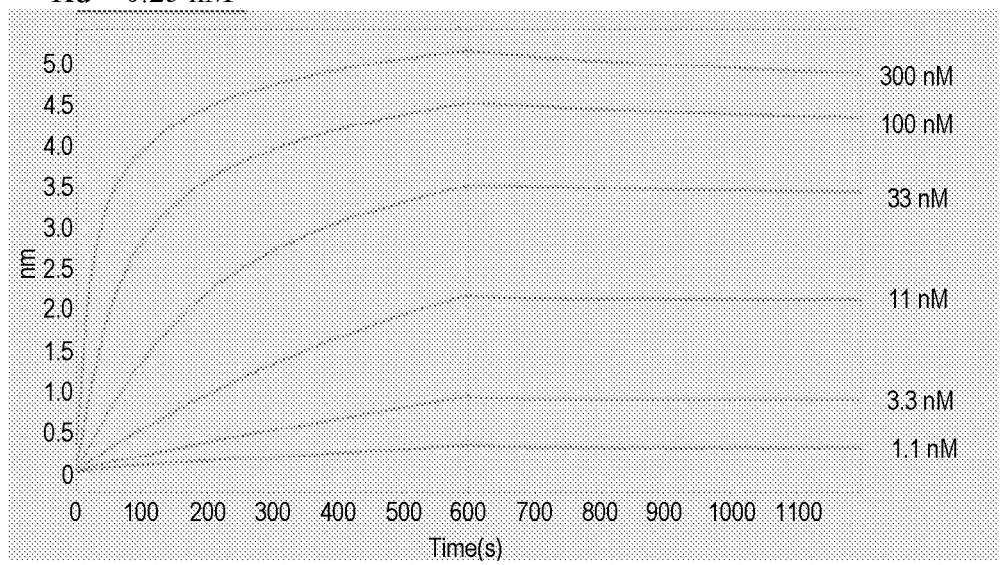
Figure 17D:
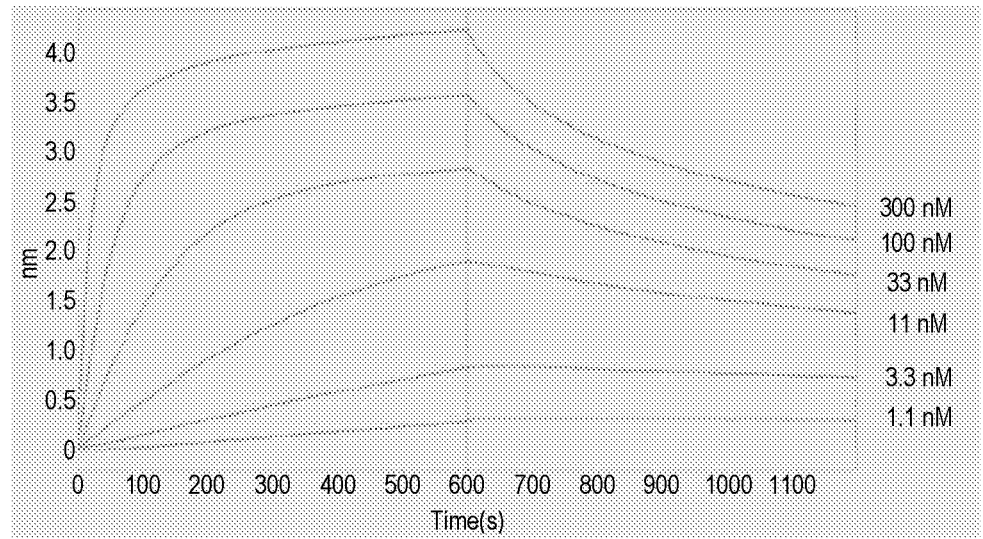

As shown in FIG. 16B, anti-FAM19A5 antibodies 1-65, P2-A03, P2-F11, and 13B4 all cross-competed with one another. This is in agreement with the earlier epitope analysis, which showed that these antibodies bind to FAM19A5 at similar epitopes (i.e., EP6, EP7, and/or EP8). See FIGS. 15A-15C.

Example 10 Binding Affinity Analysis

To determine whether there are any differences in the binding affinity of the different anti-FAM19A5 antibodies to FAM19A5, both an OCTET® test and ELISA assay were used. For the OCTET® test, the following protocol was used. In Octet QK3, Ni-NTA biosensors were hydrated in HPLC grade water. The his-tag of FAM19A5 protein was fixed on the Ni-NTA biosensors (at a level of 2 nM). The indicated anti-FAM19A5 antibodies were diluted at concentrations of 300 nM, 100 nM, 33 nM, 11 nM, 3.3 nM, 1.1 nM, and 0 nM. The kinetics of the binding of the different anti-FAM19A5 antibodies to the FAM19A5 fixed on the biosensors were measured. This data was analyzed using the Data Analysis Software (version 9.0) program.

Figures 18A, 18B:
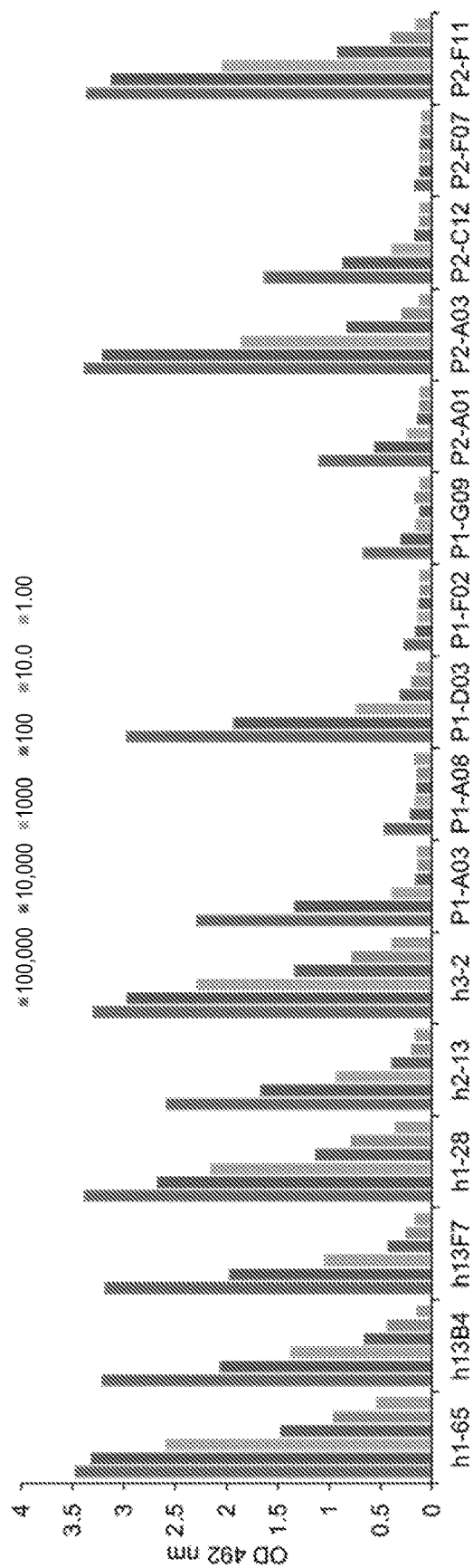
FIGS. 18A and 18B show the ELISA results for the binding of several anti-FAM19A5 antibodies to FAM19A5. The results for the following antibodies are shown: 1-65, 13B4, 13F7, 1-28, 2-13, 3-2, P1-A03, P1-A08, P1-D03, P1-F02, P1-G09, P2-A01, P2-A03, P2-C12, P2-F07, and P2-F11 (moving left to right).
Figure 19A:
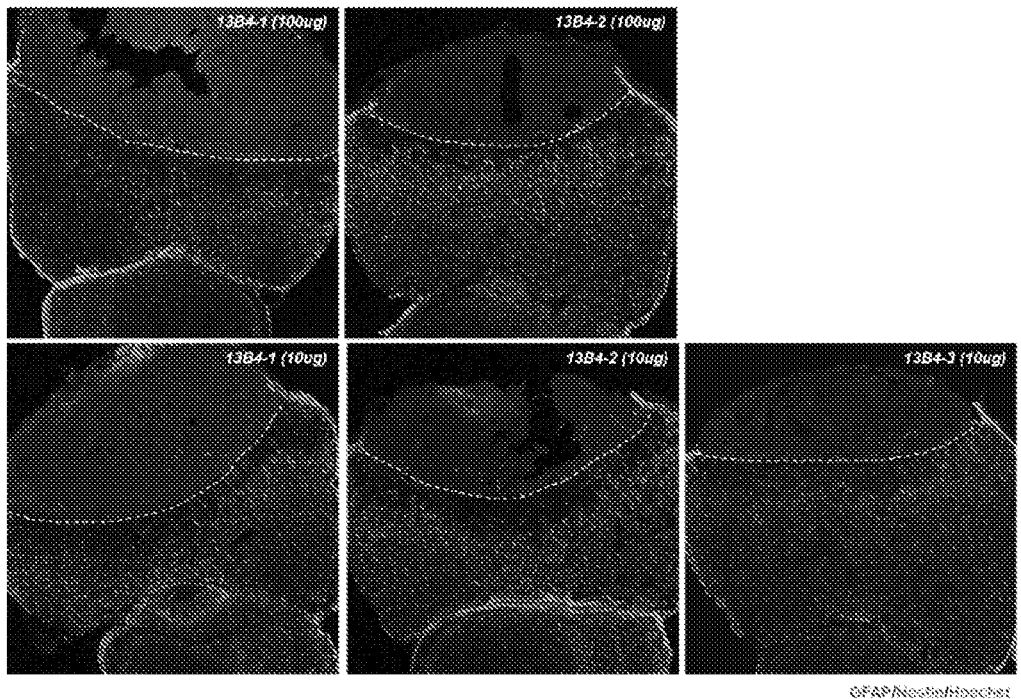
FIGS. 19A to 19E provide representative immunohistochemistry images of the damaged area of the brain tissues from animals treated with different FAM19A5 antibodies (100 μg/mouse).
Figure 19B:
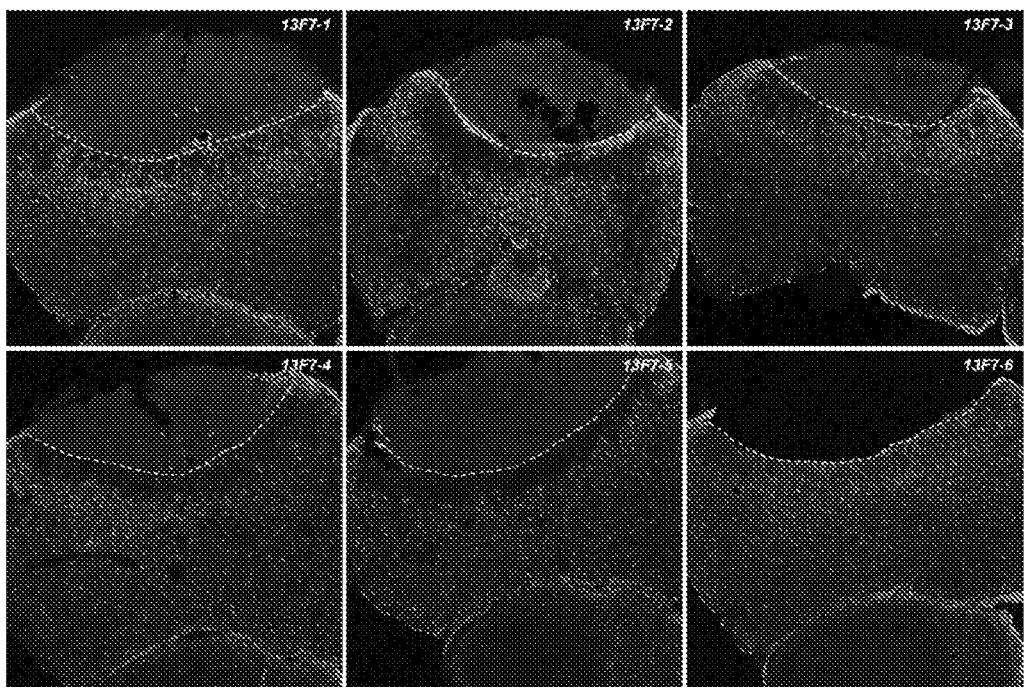
Figure 19C:
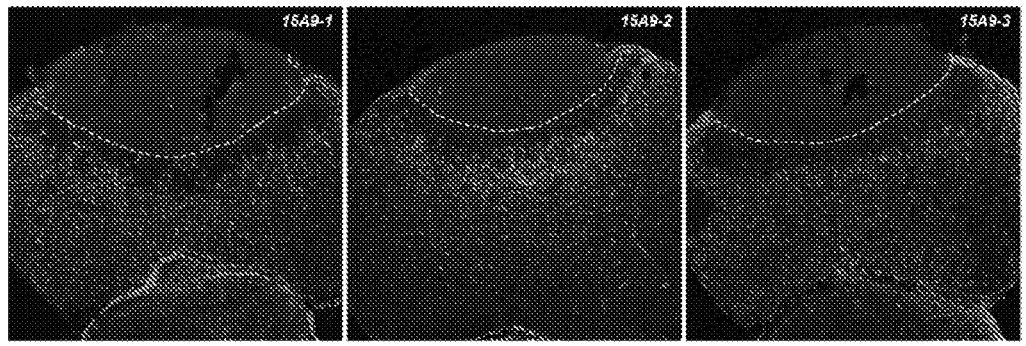
Figure 19D:
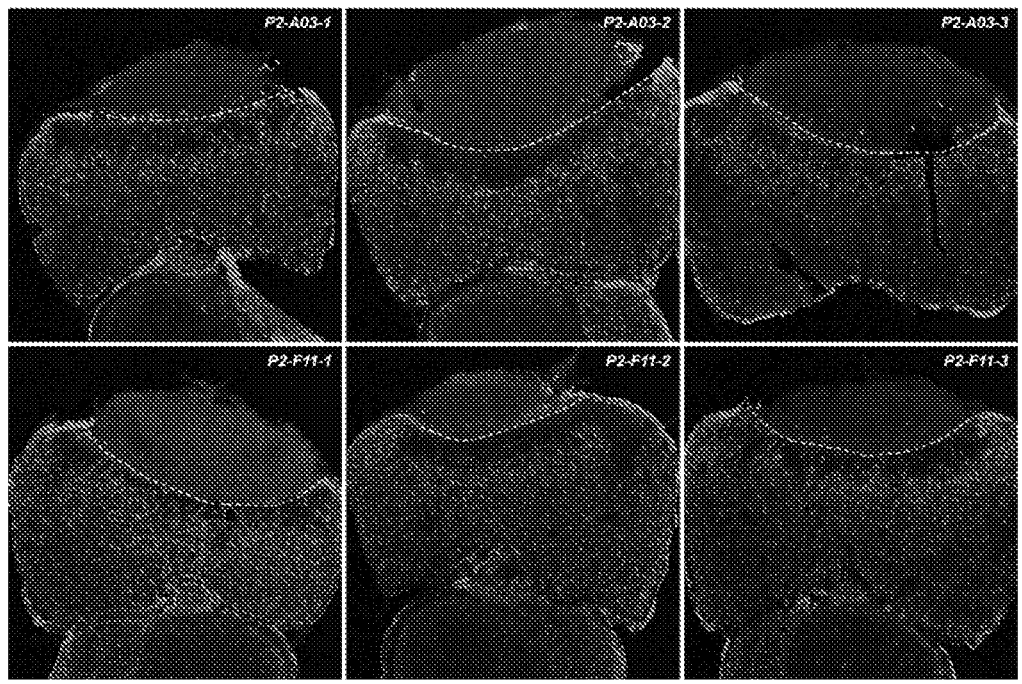
Figure 19E:
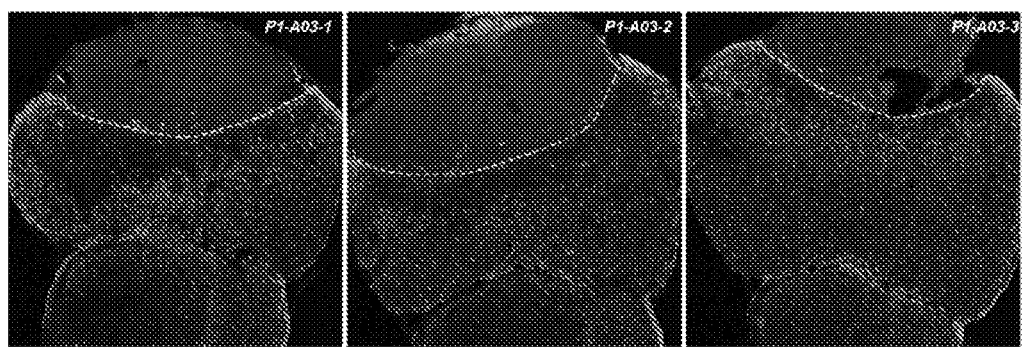

As shown in FIGS. 17A-17D, anti-FAM19A5 antibodies 1-65 and 13F7 had similar binding affinities (Kd=0.23 nM and 0.25 nM, respectively) and bound FAM19A5 more strongly compared to antibodies 13B4 (Kd=3.6 nM) and 15A9 (Kd=5.95 nM). The binding affinity of the different anti-FAM19A5 antibodies, as measured by ELISA, are provided in FIGS. 18A and 18B.

Example 11 Use of FAM19A5 Antibody in Brain Injury Animal Model

To assess the in vivo function of the anti-FAM19A5 antibodies disclosed herein, a traumatic brain injury (TBI) mouse model was used. Briefly, C57BL/6 adult male mice (8-9 weeks of age) were deeply anesthetized with sodium pentobarbital (50 mg/kg). Cryogenic TBI was performed by placing a prechilled iron rod on the calvarium for 1 min. The mouse's skin was then sutured and housed in the same manner as normal mice. Moon et al., Neuro Report 22: 304-308 (2011). Approximately 1 day after TBI induction, the animals were intravenously administered with various concentrations (0.1, 0.3, 1, 3, 5, 10, or 100 µg/mouse) of different anti-FAM19A5 antibodies diluted in phosphate-buffered saline (PBS). Normal human control immunoglobulin (HCI) was used as a control.

The animals were then sacrificed at 5 days after TBI induction (TBI5D), perfused with 4% paraformaldehyde (PFA) in PBS, and their brain tissue harvested. The harvested brain tissues were further fixed in the 4% PFA solution for an additional 24 hours. Then, the brain tissues were cyroprotected in 30% sucrose, sectioned serially on a cryostat (40 µm), and stored in 50% glycerol/50% PBS at −20° C. until use.

To stain for the reactive astrocytes associated with gliosis (positive for nestin and GFAP expression), the brain tissue sections were blocked with 3% bovine serum albumin (BSA) and 0.1% Triton X-100 in PBS for 30 min. Primary antibodies were then incubated with the sections overnight at 4° C. Primary antibodies used in this study were mouse anti-nestin (Millipore, Billerica, Mass., USA) and rabbit anti-GFAP (Dako, Carpinteria, Calif., USA). After several washes with PBS, appropriate secondary antibodies were applied for 30 min. Nuclei were labeled with Hoechst 33342 (Invitrogen, Carlsbad, Calif., USA). Subsequently, the sections were washed, mounted, and observed under a fluorescence or confocal microscope (Leica, Wetzlar, Germany).

To quantitate the effect, the ROI (Region of Interest) of the GFAP-negative region for each image was firstly specified and then the area (µm², A) of the corresponding ROI was calculated with the use of the LAS AF lite software (Leica Microsystem CMS GmbH, Mannheim, Germany). The lateral length (µm, B) of the boundary line of the injury core contacting the penumbra was also measured with the same software. The result of A/B designates average distance from lesion core (A/B, µm).

Figure 7:
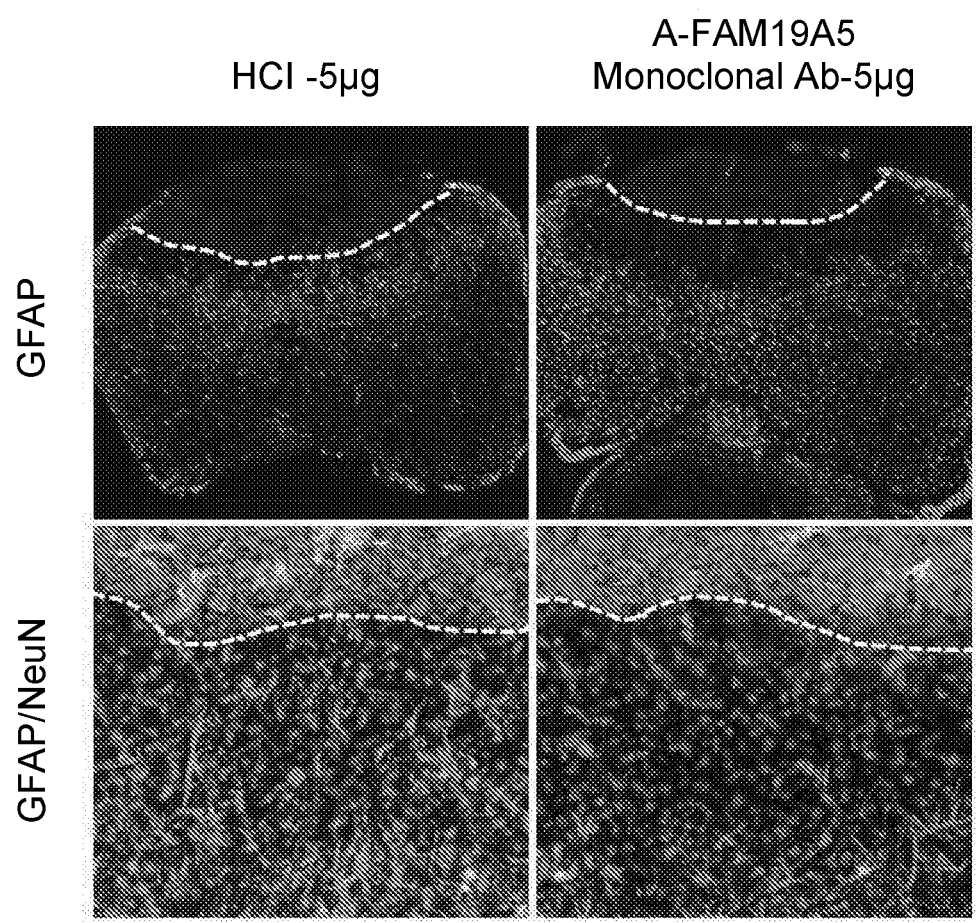
FIG. 7 shows neuroprotective effects of the chimeric anti-FAM19A5-IgG2/4 monoclonal antibody (1-65) (right panels) in traumatic brain injury mouse model. Normal human control immunoglobulin (HCI) was used as a control (left panels). The animals received 5 μg of the indicated antibody. The top panels shows GFAP (glial fibrillary acidic protein) expression within the penumbra of the damaged region. The bottom panels show the co-expression of GFAP and NeuN (neuronal nuclei) within an enlarged section of a damaged region in the TBI mice. The dashed line denotes lesion border following exposure to the traumatic brain injury.

As shown in FIG. 6, anti-FAM19A5 antibody 1-65, but not the control HCI antibody, markedly reduced, reversed, and/or prevented the onset of reactive gliosis in the penumbra areas after traumatic brain injury, as evidenced by less GFAP-positive staining near the lesion border (indicated by the dashed lines). Similar results were observed with anti-FAM19A5 antibodies 13B4, 13F7, 15A9, P2-A03, P2-F11, and P1-A03. See FIGS. 20A-20E. And as shown in FIG. 7, immunostaining of GFAP and NeuN in injury core and penumbra showed that the anti-FAM19A5 antibodies can also promote the survival of neurons in the penumbra regions surrounding the damaged area.

Example 12 Efficacy of Anti-FAM19A5 for the Treatment of Spinal Core Injury

To examine whether the anti-FAM19A5 antibodies can improve the functional locomotor activity of the injured animals, a spinal cord injury (SCI) animal model was employed. Adult male Sprague Dawley rats (DaeHan Bio-Link Co., Ltd, Korea) were anesthetized with chloral hydrate (500 mg/kg), and the eighth or tenth thoracic vertebra was exposed. To simulate human spinal cord injury, an NYU impactor (Routes, Sciteck Korea Inc.), which is designed to compute the intensity of the injury as a numerical value, was employed. A 10-g weight was dropped from a height of 25 mm on the ninth thoracic spinal cord, which was exposed through laminectomy without disrupting the dura. The computed data from the NYU impactor confirmed that the injury was delivered uniformly within the error range, and the wound was sutured. After application of povidone iodine to the wounded area, the rats were housed two per cage, and their bladders were massaged three times a day for seven weeks to facilitate urination. Each of the animals then received intravenously one of the following antibodies: (i) anti-FAM19A5 antibody 1-65 (60 µg), (ii) anti-FAM19A5 polyclonal Ab (60 µg), or (iii) normal rabbit IgG (60 µg) in PBS. Motor function of SCI animals was evaluated using the BBB locomotor score. The BBB scale ranges from 0 points for no movement of the hindlimb to 21 points for normal movement. Animals were allowed to freely roam on an open field while observed by two blinded observers. Any animal with a BBB score greater than 1 at 1 day after SCI was removed from the study. Scores were monitored for 40 days. Data were quantified as the mean±SEM of the two hind limb scores, compiled and graphed. FIG. 8 (left panel) shows that the single administration of FAM19A5 antibody 1-65 (C, circle) significantly improve the locomotor activity from 21 day-post injury (dpi) compared to that of vehicle treated rat (A, diamond). Treatment with anti-FAM19A5 polyclonal Ab (B, square) also improved the locomotor activity from 35 dpi compared to that of vehicle treated rat (A, diamond). In addition, the incline test was performed weekly until 6 weeks (FIG. 8 right panel). For the inclined plane test, rats were placed on an adjustable inclined plane. The maximum angle of the inclined plane at which each animal maintained a stable position for at least 5 seconds was evaluated by two observers who were blinded to the animal groups, and the average angle was recorded. Incline test also showed improved functional activity of the animals treated with FAM19A5 antibody 1-65 (C, circle) or anti-FAM19A5 polyclonal Ab (B, square) compared to control group (A, diamond).

It is to be appreciated that the Detailed Description section, and not the Summary and Abstract sections, is intended to be used to interpret the claims. The Summary and Abstract sections can set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

What is claimed is:

1. An isolated antibody, or antigen-binding portion thereof, which specifically binds to human family with sequence similarity 19, member A5 ("FAM19A5") protein ("anti-FAM19A5 antibody") comprising a heavy chain variable region (VH) comprising the amino acid sequence set forth in SEQ ID NO: 5 and a light chain variable region (VL) comprising the amino acid sequence set forth in SEQ ID NO: 6.

2. An isolated antibody, or antigen-binding portion thereof, which specifically binds to human family with sequence similarity 19, member A5 ("FAM19A5") protein ("anti-FAM19A5 antibody") comprising a heavy chain CDR1, CDR2, and CDR3 and a light chain CDR1, CDR2, and CDR3,
   (i) wherein the heavy chain CDR3 comprises the amino acid sequence set forth in SEQ ID NO: 9;
   (ii) wherein the heavy chain CDR1 comprises the amino acid sequence set forth in SEQ ID NO: 7;
   (iii) wherein the heavy chain CDR2 comprises the amino acid sequence set forth in SEQ ID NO: 8;
   (iv) wherein the light chain CDR1 comprises the amino acid sequence set forth in SEQ ID NO: 10;
   (v) wherein the light chain CDR2 comprises the amino acid sequence set forth in SEQ ID NO: 11; and
   (vi) wherein the light chain CDR3 comprises the amino acid sequence set forth in SEQ ID NO: 12.

3. The anti-FAM19A5 antibody of claim 2, which comprises a heavy chain variable region (VH) and a light chain variable region (VL), wherein the VH comprises an amino acid sequence which is at least about 80% identical to the amino acid sequence set forth in SEQ ID NO: 5 and/or wherein the VL comprises an amino acid sequence which is at least about 80% identical to the amino acid sequence set forth in SEQ ID NO: 6.

4. The anti-FAM19A5 antibody of claim 2, which is a chimeric antibody or a humanized antibody.

5. The anti-FAM19A5 antibody of claim 2, which comprises a heavy chain (HC) and a light chain (LC), wherein the HC comprises the amino acid sequence set forth in SEQ ID NO: 27, and/or wherein the LC comprises the amino acid sequence set forth in SEQ ID NO: 28.

6. The anti-FAM19A5 antibody of claim 2, which exhibits one or more of the following properties:
   (a) binds to soluble human FAM19A5 with a $K_D$ of 10 nM or less as measured by enzyme-linked immunosorbent assay (ELISA);
   (b) binds to membrane bound human FAM19A5 with a $K_D$ of 10 nM or less as measured by ELISA;
   (c) reduces, reverses, delays, and/or prevents an onset of reactive gliosis;
   (d) suppresses an excessive proliferation of reactive astrocytes;
   (e) decreases expression of chondroitin sulfate proteoglycans including neurocan and neuron-glial antigen 2 (NG2);
   (f) increases expression of c-fos and pERK in the nucleus of neurons;
   (g) promotes survival of neurons;
   (h) increases expression of GAP43 in neurons; and
   (i) promotes regrowth of an axon.

7. A composition comprising the anti-FAM19A5 antibody of claim 2 and a carrier.

8. A method of treating a traumatic brain injury, spinal cord injury, or both in a subject in need thereof comprising administering to the subject the anti-FAM19A5 antibody of claim 2.

9. A method of treating a traumatic brain injury, spinal cord injury, or both in a subject in need thereof comprising administering to the subject the anti-FAM19A5 antibody of claim 1.

10. A composition comprising the anti-FAM19A5 antibody of claim 1 and a carrier.

11. The anti-FAM19A5 antibody of claim 2, which comprises a heavy chain constant region selected from the group consisting of an IgG1, an IgG2, an IgG3, an IgG4, and a variant thereof.

12. The anti-FAM19A5 antibody of claim 1, which comprises a heavy chain constant region selected from the group consisting of an IgG1, an IgG2, an IgG3, an IgG4, and a variant thereof.

13. The anti-FAM19A5 antibody of claim 1, which is a chimeric antibody or a humanized antibody.

14. The anti-FAM19A5 antibody of claim 1, which comprises a heavy chain (HC) and a light chain (LC), wherein the HC comprises the amino acid sequence set forth in SEQ ID NO: 27, and/or wherein the LC comprises the amino acid sequence set forth in SEQ ID NO: 28.

15. A bispecific molecule comprising the anti-FAM19A5 antibody of claim 1.

16. A bispecific molecule comprising the anti-FAM19A5 antibody of claim 2.

17. The anti-FAM19A5 antibody of claim 1, wherein the antigen-binding portion thereof comprises a Fab, Fab', F(ab')2, Fv fragment, single chain Fv (scFv), single domain antibody (sdAb), or combinations thereof.

18. The anti-FAM19A5 antibody of claim 2, wherein the antigen-binding portion thereof comprises a Fab, Fab', F(ab')2, Fv fragment, single chain Fv (scFv), single domain antibody (sdAb), or combinations thereof.

19. An immunoconjugate comprising the anti-FAM19A5 antibody of claim 1 linked to an agent.

20. An immunoconjugate comprising the anti-FAM19A5 antibody of claim 2 linked to an agent.

* * * * *

SEQUENCE LISTING

```
<160> NUMBER OF SEQ ID NOS: 166

<210> SEQ ID NO 1
<211> LENGTH: 132
<212> TYPE: PRT
<213> ORGANISM: Homo Sapiens

<400> SEQUENCE: 1

Met Ala Pro Ser Pro Arg Thr Gly Ser Arg Gln Asp Ala Thr Ala Leu
1               5                   10                  15
```

```
Pro Ser Met Ser Ser Thr Phe Trp Ala Phe Met Ile Leu Ala Ser Leu
            20                  25                  30

Leu Ile Ala Tyr Cys Ser Gln Leu Ala Ala Gly Thr Cys Glu Ile Val
         35                  40                  45

Thr Leu Asp Arg Asp Ser Ser Gln Pro Arg Arg Thr Ile Ala Arg Gln
     50                  55                  60

Thr Ala Arg Cys Ala Cys Arg Lys Gly Gln Ile Ala Gly Thr Thr Arg
 65                  70                  75                  80

Ala Arg Pro Ala Cys Val Asp Ala Arg Ile Ile Lys Thr Lys Gln Trp
                 85                  90                  95

Cys Asp Met Leu Pro Cys Leu Glu Gly Glu Gly Cys Asp Leu Leu Ile
            100                 105                 110

Asn Arg Ser Gly Trp Thr Cys Thr Gln Pro Gly Gly Arg Ile Lys Thr
        115                 120                 125

Thr Thr Val Ser
    130

<210> SEQ ID NO 2
<211> LENGTH: 20
<212> TYPE: PRT
<213> ORGANISM: Artificial Sequence
<220> FEATURE:
<223> OTHER INFORMATION: Epitope F5

<400> SEQUENCE: 2

Cys Asp Met Leu Pro Cys Leu Glu Gly Glu Gly Cys Asp Leu Leu Ile
1               5                   10                  15

Asn Arg Ser Gly
            20

<210> SEQ ID NO 3
<211> LENGTH: 1501
<212> TYPE: DNA
<213> ORGANISM: Homo Sapiens

<400> SEQUENCE: 3
ggcggcggag gatggcgcgc gcggggcccg cacgtggagg ccggcgcggg ggcgcgggca      60
gggccggctg ctgagacgcg ctgctgcccc ccgcgcgggc gccgcggctt caatggcgcc     120
atcgcccagg accggcagcc ggcaagatgc gaccgccctg cccagcatgt cctcaacttt     180
ctgggcgttc atgatcctgg ccagcctgct catcgcctac tgcagtcagc tggccgccgg     240
cacctgtgag attgtgacct ggaccgggga cagcagccag cctcggagga cgatcgcccg     300
gcagaccgcc cgctgtgcgt gtagaaaggg gcagatcgcc ggcaccacga gcccggcc      360 cgcctgtgtg gacgcaagaa tcatcaagac caagcagtgg tgtgacatgc ttccgtgtct     420
ggagggggaa ggctgcgact tgttaatcaa ccggtcaggc tggacgtgca cgcagcccgg     480
cgggaggata aagaccacca cggtctcctg acaaacacag cccctgaggg ggccccggga     540
gtggccttgg ctccctggag agcccacgtc tcagccacag ttctccactc gcctcggact     600
tcacccgttc tctgccgccc gcccactccg tttccctgtg gtccgtgaag acggcctca     660 ggccttggca tcctgagctt cggtctgtcc agccgacccg aggaggccgg actcagacac     720
ataggcgggg ggcggcacct ggcatcagca atacgcagtc tgtgggagcc cggccgcgcc     780
cagcccccgc cgaccgtggc gttggccctg ctgtcctcag aggaggagga ggaggagca     840 gctccggcag ccacagaagg ctgcagccca gcccgcctga cacgacgc ctgccccagg     900 ggactgtcag gcacagaagc ggcctcctcc cgtgcccag actgtccgaa ttgcttttat     960
```

```
tttcttatac tttcagtata ctccatagac caaagagcaa aatctatctg aacctggacg    1020
caccctcact gtcagggtcc ctggggtcgc ttgtgcgggc gggagggcaa tggtggcaga    1080
gacatgctgg tggccccggc ggagcggaga gggcggccgt ggtggaggcc tccaccccag    1140
gagcaccccg cacaccctcg gaggacgggc ttcggctgcg cggaggccgt ggcacacctg    1200
cgggaggcag cgacggcccc cacgcagacg ccgggaacgc aggccgcttt attcctctgt    1260
acttagatca acttgaccgt actaaaatcc ctttctgttt taaccagtta acatgcctc     1320 ttctacagct ccattttga tagttggata atccagtatc tgccaagagc atgttgggtc    1380
tcccgtgact gctgcctcat cgataccca tttagctcca gaaagcaaag aaaactcgag    1440
taacacttgt ttgaaagaga tcattaaatg tattttgcaa agcccaaaaa aaaaaaaaa    1500 a                                                                  1501
```

<210> SEQ ID NO 4
<211> LENGTH: 125
<212> TYPE: PRT
<213> ORGANISM: Homo Sapiens

<400> SEQUENCE: 4

```
Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Arg
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Asp Met Leu Pro Cys Leu
                85                  90                  95

Glu Gly Glu Gly Cys Asp Leu Leu Ile Asn Arg Ser Gly Trp Thr Cys
            100                 105                 110

Thr Gln Pro Gly Gly Arg Ile Lys Thr Thr Thr Val Ser
        115                 120                 125
```

<210> SEQ ID NO 5
<211> LENGTH: 122
<212> TYPE: PRT
<213> ORGANISM: Artificial Sequence
<220> FEATURE:
<223> OTHER INFORMATION: 1-65 Antibody VH

<400> SEQUENCE: 5

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Gln Met Gly Trp Val Arg Gln Ala Pro Gly Lys Gly Leu Glu Trp Val
        35                  40                  45

Gly Val Ile Asn Lys Ser Gly Ser Asp Thr Ser Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Phe Cys
```

```
                85                  90                  95
Ala Lys Gly Ser Ala Ser Tyr Ile Thr Ala Ala Thr Ile Asp Ala Trp
            100                 105                 110

Gly His Gly Thr Glu Val Ile Val Ser Ser
        115                 120

<210> SEQ ID NO 6
<211> LENGTH: 110
<212> TYPE: PRT
<213> ORGANISM: Artificial Sequence
<220> FEATURE:
<223> OTHER INFORMATION: 1-65 Antibody VL

<400> SEQUENCE: 6

Ala Leu Thr Gln Pro Ser Ser Val Ser Ala Asn Pro Gly Glu Thr Val
1               5                   10                  15

Lys Ile Thr Cys Ser Gly Gly Ser Ser Gly Tyr Gly Tyr Gly Trp
            20                  25                  30

Tyr Gln Gln Lys Ser Pro Ser Ala Pro Leu Thr Val Ile Tyr Trp
        35                  40                  45

Asn Asp Lys Arg Pro Ser Asp Ile Pro Ser Arg Phe Ser Gly Ser Lys
    50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu
            100                 105                 110

<210> SEQ ID NO 7
<211> LENGTH: 5
<212> TYPE: PRT
<213> ORGANISM: Artificial Sequence
<220> FEATURE:
<223> OTHER INFORMATION: 1-65 Antibody VH-CDR1

<400> SEQUENCE: 7

Ser Tyr Gln Met Gly
1               5

<210> SEQ ID NO 8
<211> LENGTH: 10
<212> TYPE: PRT
<213> ORGANISM: Artificial Sequence
<220> FEATURE:
<223> OTHER INFORMATION: 1-65 Antibody VH-CDR2

<400> SEQUENCE: 8

Val Ile Asn Lys Ser Gly Ser Asp Thr Ser
1               5                   10

<210> SEQ ID NO 9
<211> LENGTH: 13
<212> TYPE: PRT
<213> ORGANISM: Artificial Sequence
<220> FEATURE:
<223> OTHER INFORMATION: 1-65 Antibody VH-CDR3

<400> SEQUENCE: 9

Gly Ser Ala Ser Tyr Ile Thr Ala Ala Thr Ile Asp Ala
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: 1-65 Antibody VL-CDR1

<400> SEQUENCE: 10

Ser Gly Gly Gly Ser Ser Gly Tyr Gly Tyr Gly
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 1-65 Antibody VL-CDR2

<400> SEQUENCE: 11

Trp Asn Asp Lys Arg Pro Ser
1               5

<210> SEQ ID NO 12
<211> LENGTH: 14
<212> TYPE: PRT
<213> ORGANISM: Artificial Sequence
<220> FEATURE:
<223> OTHER INFORMATION: 1-65 Antibody VL-CDR3

<400> SEQUENCE: 12

Gly Asn Asp Asp Tyr Ser Ser Asp Ser Gly Tyr Val Gly Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Epitope F1

<400> SEQUENCE: 13

Gln Leu Ala Ala Gly Thr Cys Glu Ile Val Thr Leu Asp Arg
1               5                   10

<210> SEQ ID NO 14
<211> LENGTH: 20
<212> TYPE: PRT
<213> ORGANISM: Artificial Sequence
<220> FEATURE:
<223> OTHER INFORMATION: Epitope F2

<400> SEQUENCE: 14

Thr Leu Asp Arg Asp Ser Ser Gln Pro Arg Arg Thr Ile Ala Arg Gln
1               5                   10                  15

Thr Ala Arg Cys
            20

<210> SEQ ID NO 15
<211> LENGTH: 20
<212> TYPE: PRT
<213> ORGANISM: Artificial Sequence
<220> FEATURE:
<223> OTHER INFORMATION: Epitope F3

<400> SEQUENCE: 15

Thr Ala Arg Cys Ala Cys Arg Lys Gly Gln Ile Ala Gly Thr Thr Arg
1               5                   10                  15
```

-continued

Ala Arg Pro Ala
            20

<210> SEQ ID NO 16
<211> LENGTH: 20
<212> TYPE: PRT
<213> ORGANISM: Artificial Sequence
<220> FEATURE:
<223> OTHER INFORMATION: Epitope F4

<400> SEQUENCE: 16

Ala Arg Pro Ala Cys Val Asp Ala Arg Ile Ile Lys Thr Lys Gln Trp
1               5                   10                  15

Cys Asp Met Leu
            20

<210> SEQ ID NO 17
<211> LENGTH: 20
<212> TYPE: PRT
<213> ORGANISM: Artificial Sequence
<220> FEATURE:
<223> OTHER INFORMATION: Epitope F6

<400> SEQUENCE: 17

Asn Arg Ser Gly Trp Thr Cys Thr Gln Pro Gly Gly Arg Ile Lys Thr
1               5                   10                  15

Thr Thr Val Ser
            20

<210> SEQ ID NO 18
<211> LENGTH: 366
<212> TYPE: DNA
<213> ORGANISM: Artificial Sequence
<220> FEATURE:
<223> OTHER INFORMATION: 1-65 Antibody VH

<400> SEQUENCE: 18
gccgtgacac tggacgaatc tgggggaggg ctgcagactc caggcggagc tctgagcctg      60
gtgtgcaagg catccgggtt caccttagc tcctaccaga tgggatgggt gcggcaggca     120
ccagggaagg gcctggagtg gtcggagtg atcaacaaat ctgggagtga cacaagctac     180
ggcagcgccg tgaagggaag ggccaccatc agcaggaca atggccagag taccgtgcgg     240
ctgcagctga caatctgcg cgctgaggac actggcacct acttctgtgc taagggatca     300
gcaagctata tcacagccgc tactattgat gcatggggac acgggacaga agtcatcgtg     360
tctagt                                                                366

<210> SEQ ID NO 19
<211> LENGTH: 330
<212> TYPE: DNA
<213> ORGANISM: Artificial Sequence
<220> FEATURE:
<223> OTHER INFORMATION: 1-65 Antibody VL

<400> SEQUENCE: 19
gccctgactc agccctcttc cgtgtcagcc aaccctggag aaactgtgaa gatcacctgc      60
agcggaggag ggagctccgg atacggatat gggtggtatc agcagaaatc ccatctagt     120 gcccccctga ctgtgatcta ttggaacgac aagaggccta gtgatattcc atcaagattc     180
agtggatcaa aaagcgggtc cactcacacc ctgacaatca ctggcgtgca ggcagaggac     240
gaagccgtct acttctgcgg aaatgacgat tactcaagcg attctggcta tgtgggcgtc     300
tttggcgcag gaaccacact gacagtgctg         330

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26
<211> LENGTH: 53
<212> TYPE: PRT
<213> ORGANISM: Homo Sapiens

<400> SEQUENCE: 26

Met Tyr His His Arg Glu Trp Pro Ala Arg Ile Ile Lys Thr Lys Gln
1               5                   10                  15

Trp Cys Asp Met Leu Pro Cys Leu Glu Gly Glu Gly Cys Asp Leu Leu
            20                  25                  30

Ile Asn Arg Ser Gly Trp Thr Cys Thr Gln Pro Gly Gly Arg Ile Lys
        35                  40                  45

Thr Thr Thr Val Ser
    50

<210> SEQ ID NO 27
<211> LENGTH: 452
<212> TYPE: PRT
<213> ORGANISM: Artificial Sequence
<220> FEATURE:
<223> OTHER INFORMATION: 1-65 Antibody HC

<400> SEQUENCE: 27

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr

```
                20                  25                  30
Gln Met Gly Trp Val Arg Gln Ala Pro Gly Lys Gly Leu Glu Trp Val
            35                  40                  45
Gly Val Ile Asn Lys Ser Gly Ser Asp Thr Ser Tyr Gly Ser Ala Val
        50                  55                  60
Lys Gly Arg Ala Thr Ile Ser Arg Asp Asn Gly Gln Ser Thr Val Arg
65                  70                  75                  80
Leu Gln Leu Asn Asn Leu Arg Ala Glu Asp Thr Gly Thr Tyr Phe Cys
                85                  90                  95
Ala Lys Gly Ser Ala Ser Tyr Ile Thr Ala Ala Thr Ile Asp Ala Trp
            100                 105                 110
Gly His Gly Thr Glu Val Ile Val Ser Ser Ala Ser Thr Lys Gly Pro
        115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
```

-continued

```
Ser Pro Gly Lys
    450

<210> SEQ ID NO 28
<211> LENGTH: 217
<212> TYPE: PRT
<213> ORGANISM: Artificial Sequence
<220> FEATURE:
<223> OTHER INFORMATION: 1-65 Antibody LC

<400> SEQUENCE: 28

Ala Leu Thr Gln Pro Ser Ser Val Ser Ala Asn Pro Gly Glu Thr Val
1               5                   10                  15

Lys Ile Thr Cys Ser Gly Gly Ser Ser Gly Tyr Gly Tyr Gly Trp
            20                  25                  30

Tyr Gln Gln Lys Ser Pro Ser Ser Ala Pro Leu Thr Val Ile Tyr Trp
        35                  40                  45

Asn Asp Lys Arg Pro Ser Asp Ile Pro Ser Arg Phe Ser Gly Ser Lys
    50                  55                  60

Ser Gly Ser Thr His Thr Leu Thr Ile Thr Gly Val Gln Ala Glu Asp
65                  70                  75                  80

Glu Ala Val Tyr Phe Cys Gly Asn Asp Asp Tyr Ser Ser Asp Ser Gly
                85                  90                  95

Tyr Val Gly Val Phe Gly Ala Gly Thr Thr Leu Thr Val Leu Arg Ser
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 29
<211> LENGTH: 5
<212> TYPE: PRT
<213> ORGANISM: Artificial Sequence
<220> FEATURE:
<223> OTHER INFORMATION: P2-C12  antibody VH CDR1

<400> SEQUENCE: 29

Thr Tyr Ala Val Thr
1               5

<210> SEQ ID NO 30
<211> LENGTH: 16
<212> TYPE: PRT
<213> ORGANISM: Artificial Sequence
<220> FEATURE:
<223> OTHER INFORMATION: P2-C12 antibody VH CDR2

<400> SEQUENCE: 30
```

Tyr Ile Asn Trp Arg Gly Gly Thr Ser Tyr Ala Asn Trp Ala Lys Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: P2-C12 antibody VH CDR3

<400> SEQUENCE: 31

Asp Ala Ser Ser Gly Ala Ala Phe Gly Ser Tyr Gly Met Asp Pro
1               5                   10                  15

<210> SEQ ID NO 32
<211> LENGTH: 11
<212> TYPE: PRT
<213> ORGANISM: Artificial Sequence
<220> FEATURE:
<223> OTHER INFORMATION: P2-C12 antibody VL CDR1

<400> SEQUENCE: 32

Gln Ala Ser Gln Ser Ile Ser Ser Tyr Leu Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: P2-C12 antibody VL CDR2

<400> SEQUENCE: 33

Glu Ala Ser Lys Leu Ala Ser
1               5

<210> SEQ ID NO 34
<211> LENGTH: 12
<212> TYPE: PRT
<213> ORGANISM: Artificial Sequence
<220> FEATURE:
<223> OTHER INFORMATION: P2-C12 antibody VL CDR3

<400> SEQUENCE: 34

Gln Gln Gly Tyr Ser Ser Thr Asn Val Trp Asn Ala
1               5                   10

<210> SEQ ID NO 35
<211> LENGTH: 6
<212> TYPE: PRT
<213> ORGANISM: Artificial Sequence
<220> FEATURE:
<223> OTHER INFORMATION: 13B4 antibody VH CDR1

<400> SEQUENCE: 35

Ser Ser Asn Trp Trp Ser
1               5

<210> SEQ ID NO 36
<211> LENGTH: 16
<212> TYPE: PRT
<213> ORGANISM: Artificial Sequence
<220> FEATURE:
<223> OTHER INFORMATION: 13B4 antibody VH CDR2

<400> SEQUENCE: 36

Glu Ile Tyr His Gly Gly Thr Thr Asn Tyr Asn Pro Ser Leu Lys Gly
1               5                   10                  15

-continued

```
1               5                   10                  15
```

<210> SEQ ID NO 37
<211> LENGTH: 9
<212> TYPE: PRT
<213> ORGANISM: Artificial Sequence
<220> FEATURE:
<223> OTHER INFORMATION: 13B4 antibody VH CDR3

<400> SEQUENCE: 37

Trp Gln Leu Val Gly Gly Leu Asp Val
1               5

<210> SEQ ID NO 38
<211> LENGTH: 11
<212> TYPE: PRT
<213> ORGANISM: Artificial Sequence
<220> FEATURE:
<223> OTHER INFORMATION: 13B4 antibody VL CDR1

<400> SEQUENCE: 38

Ser Gly Asp Lys Leu Gly Asn Val Tyr Ala Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: 13B4 antibody VL CDR2

<400> SEQUENCE: 39

Gln Asp Asn Lys Arg Pro Ser
1               5

<210> SEQ ID NO 40
<211> LENGTH: 9
<212> TYPE: PRT
<213> ORGANISM: Artificial Sequence
<220> FEATURE:
<223> OTHER INFORMATION: 13B4 antibody VL CDR3

<400> SEQUENCE: 40

Gln Ala Trp Asp Ser Ser Thr Ala Val
1               5

<210> SEQ ID NO 41
<211> LENGTH: 5
<212> TYPE: PRT
<213> ORGANISM: Artificial Sequence
<220> FEATURE:
<223> OTHER INFORMATION: 13F7 antibody VH CDR1

<400> SEQUENCE: 41

Gly Tyr Ser Trp Thr
1               5

<210> SEQ ID NO 42
<211> LENGTH: 16
<212> TYPE: PRT
<213> ORGANISM: Artificial Sequence
<220> FEATURE:
<223> OTHER INFORMATION: 13F7 antibody VH CDR2

<400> SEQUENCE: 42

Glu Ile Ser His Phe Gly Ser Ala Asn Tyr Asn Pro Ser Leu Lys Ser
1               5                   10                  15

```
<210> SEQ ID NO 43
<211> LENGTH: 15
<212> TYPE: PRT
<213> ORGANISM: Artificial Sequence
<220> FEATURE:
<223> OTHER INFORMATION: 13F7 antibody VH CDR3

<400> SEQUENCE: 43

Ala Leu Arg Gly Thr Tyr Ser Arg Phe Tyr Tyr Gly Met Asp Val
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: 13F7 antibody VL CDR1

<400> SEQUENCE: 44

Arg Ser Ser Gln Ser Leu Leu His Ser Asn Gly Tyr Asn Tyr Leu Asp
1               5                   10                  15

<210> SEQ ID NO 45
<211> LENGTH: 7
<212> TYPE: PRT
<213> ORGANISM: Artificial Sequence
<220> FEATURE:
<223> OTHER INFORMATION: 13F7 antibody VL CDR2

<400> SEQUENCE: 45

Leu Gly Ser Asn Arg Ala Ser
1               5

<210> SEQ ID NO 46
<211> LENGTH: 9
<212> TYPE: PRT
<213> ORGANISM: Artificial Sequence
<220> FEATURE:
<223> OTHER INFORMATION: 13F7 antibody VL CDR3

<400> SEQUENCE: 46

Met Gln Ala Arg Gln Thr Pro Leu Thr
1               5

<210> SEQ ID NO 47
<211> LENGTH: 5
<212> TYPE: PRT
<213> ORGANISM: Artificial Sequence
<220> FEATURE:
<223> OTHER INFORMATION: 15A9 antibody VH CDR1

<400> SEQUENCE: 47

Ser Tyr Tyr Trp Ser
1               5

<210> SEQ ID NO 48
<211> LENGTH: 16
<212> TYPE: PRT
<213> ORGANISM: Artificial Sequence
<220> FEATURE:
<223> OTHER INFORMATION: 15A9 antibody VH CDR2

<400> SEQUENCE: 48

Tyr Ile Tyr Pro Ser Gly Ser Thr Asn Tyr Asn Pro Ser Leu Lys Ser
1               5                   10                  15
```

<210> SEQ ID NO 49
<211> LENGTH: 12
<212> TYPE: PRT
<213> ORGANISM: Artificial Sequence
<220> FEATURE:
<223> OTHER INFORMATION: 15A9 antibody VH CDR3

<400> SEQUENCE: 49

Val Asn Pro Phe Gly Tyr Tyr Tyr Ala Met Asp Val
1               5                   10

<210> SEQ ID NO 50
<211> LENGTH: 11
<212> TYPE: PRT
<213> ORGANISM: Artificial Sequence
<220> FEATURE:
<223> OTHER INFORMATION: 15A9 antibody VL CDR1

<400> SEQUENCE: 50

Arg Ala Ser Gln Ser Ile Ser Thr Ser Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: 15A9 antibody VL CDR2

<400> SEQUENCE: 51

Gly Ala Ser Thr Leu Gln Ser
1               5

<210> SEQ ID NO 52
<211> LENGTH: 9
<212> TYPE: PRT
<213> ORGANISM: Artificial Sequence
<220> FEATURE:
<223> OTHER INFORMATION: 15A9 antibody VL CDR3

<400> SEQUENCE: 52

Gln Glu Ser Ala Ser Ile Pro Arg Thr
1               5

<210> SEQ ID NO 53
<211> LENGTH: 5
<212> TYPE: PRT
<213> ORGANISM: Artificial Sequence
<220> FEATURE:
<223> OTHER INFORMATION: P1-A03 antibody VH CDR1

<400> SEQUENCE: 53

Ser Asp Tyr Met Ser
1               5

<210> SEQ ID NO 54
<211> LENGTH: 16
<212> TYPE: PRT
<213> ORGANISM: Artificial Sequence
<220> FEATURE:
<223> OTHER INFORMATION: P1-A03 antibody VH CDR2

<400> SEQUENCE: 54

Ile Ile Tyr Pro Ser Thr Thr Thr Tyr Tyr Ala Ser Trp Ala Lys Gly
1               5                   10                  15

```
<210> SEQ ID NO 55
<211> LENGTH: 10
<212> TYPE: PRT
<213> ORGANISM: Artificial Sequence
<220> FEATURE:
<223> OTHER INFORMATION: P1-A03 antibody VH CDR3

<400> SEQUENCE: 55

Gly Ser Asn Trp Ser Ser Gly Met Asn Leu
1               5                   10

<210> SEQ ID NO 56
<211> LENGTH: 11
<212> TYPE: PRT
<213> ORGANISM: Artificial Sequence
<220> FEATURE:
<223> OTHER INFORMATION: P1-A03 antibody VL CDR1

<400> SEQUENCE: 56

Leu Ala Ser Glu Asp Ile Tyr Ser Gly Ile Ser
1               5                   10

<210> SEQ ID NO 57
<211> LENGTH: 7
<212> TYPE: PRT
<213> ORGANISM: Artificial Sequence
<220> FEATURE:
<223> OTHER INFORMATION: P1-A03 antibody VL CDR2

<400> SEQUENCE: 57

Gly Ala Ser Asn Leu Glu Ser
1               5

<210> SEQ ID NO 58
<211> LENGTH: 12
<212> TYPE: PRT
<213> ORGANISM: Artificial Sequence
<220> FEATURE:
<223> OTHER INFORMATION: P1-A03 antibody VL CDR3

<400> SEQUENCE: 58

Leu Gly Gly Tyr Ser Tyr Ser Ser Thr Gly Leu Thr
1               5                   10

<210> SEQ ID NO 59
<211> LENGTH: 5
<212> TYPE: PRT
<213> ORGANISM: Artificial Sequence
<220> FEATURE:
<223> OTHER INFORMATION: P1-A08 antibody VH CDR1

<400> SEQUENCE: 59

Thr Tyr Tyr Met Ser
1               5

<210> SEQ ID NO 60
<211> LENGTH: 16
<212> TYPE: PRT
<213> ORGANISM: Artificial Sequence
<220> FEATURE:
<223> OTHER INFORMATION: P1-A08 antibody VH CDR2

<400> SEQUENCE: 60

Ile Val Tyr Pro Ser Gly Thr Thr Tyr Tyr Ala Asn Trp Ala Lys Gly
1               5                   10                  15

<210> SEQ ID NO 61
```

```
<211> LENGTH: 8
<212> TYPE: PRT
<213> ORGANISM: Artificial Sequence
<220> FEATURE:
<223> OTHER INFORMATION: P1-A08 antibody VH CDR3

<400> SEQUENCE: 61

Gly Asp Ser Phe Gly Tyr Gly Leu
1               5

<210> SEQ ID NO 62
<211> LENGTH: 11
<212> TYPE: PRT
<213> ORGANISM: Artificial Sequence
<220> FEATURE:
<223> OTHER INFORMATION: P1-A08 antibody VL CDR1

<400> SEQUENCE: 62

Thr Ala Asp Thr Leu Ser Arg Ser Tyr Ala Ser
1               5                   10

<210> SEQ ID NO 63
<211> LENGTH: 7
<212> TYPE: PRT
<213> ORGANISM: Artificial Sequence
<220> FEATURE:
<223> OTHER INFORMATION: P1-A08 antibody VL CDR2

<400> SEQUENCE: 63

Arg Asp Thr Ser Arg Pro Ser
1               5

<210> SEQ ID NO 64
<211> LENGTH: 13
<212> TYPE: PRT
<213> ORGANISM: Artificial Sequence
<220> FEATURE:
<223> OTHER INFORMATION: P1-A08 antibody VL CDR3

<400> SEQUENCE: 64

Ala Thr Ser Asp Gly Ser Gly Ser Asn Tyr Gln Tyr Val
1               5                   10

<210> SEQ ID NO 65
<211> LENGTH: 5
<212> TYPE: PRT
<213> ORGANISM: Artificial Sequence
<220> FEATURE:
<223> OTHER INFORMATION: P1-F02 antibody VH CDR1

<400> SEQUENCE: 65

Asn Tyr Tyr Met Gly
1               5

<210> SEQ ID NO 66
<211> LENGTH: 16
<212> TYPE: PRT
<213> ORGANISM: Artificial Sequence
<220> FEATURE:
<223> OTHER INFORMATION: P1-F02 antibody VH CDR2

<400> SEQUENCE: 66

Ile Ile Tyr Ala Ser Gly Ser Thr Tyr Tyr Ala Ser Trp Ala Lys Gly
1               5                   10                  15

<210> SEQ ID NO 67
<211> LENGTH: 17
```

```
<212> TYPE: PRT
<213> ORGANISM: Artificial Sequence
<220> FEATURE:
<223> OTHER INFORMATION: P1-F02 antibody VH CDR3

<400> SEQUENCE: 67

Ile Asp Ile Gly Val Gly Asp Tyr Gly Trp Ala Tyr Asp Arg Leu Asp
1               5                   10                  15
Leu

<210> SEQ ID NO 68
<211> LENGTH: 11
<212> TYPE: PRT
<213> ORGANISM: Artificial Sequence
<220> FEATURE:
<223> OTHER INFORMATION: P1-F02 antibody VL CDR1

<400> SEQUENCE: 68

Leu Ala Ser Glu Asp Ile Tyr Ser Gly Ile Ser
1               5                   10

<210> SEQ ID NO 69
<211> LENGTH: 7
<212> TYPE: PRT
<213> ORGANISM: Artificial Sequence
<220> FEATURE:
<223> OTHER INFORMATION: P1-F02 antibody VL CDR2

<400> SEQUENCE: 69

Gly Ala Ser Asn Leu Glu Ser
1               5

<210> SEQ ID NO 70
<211> LENGTH: 10
<212> TYPE: PRT
<213> ORGANISM: Artificial Sequence
<220> FEATURE:
<223> OTHER INFORMATION: P1-F02 antibody VL CDR3

<400> SEQUENCE: 70

Leu Gly Gly Tyr Ser Tyr Ser Ser Ile Thr
1               5                   10

<210> SEQ ID NO 71
<211> LENGTH: 5
<212> TYPE: PRT
<213> ORGANISM: Artificial Sequence
<220> FEATURE:
<223> OTHER INFORMATION: P2-A01 antibody VH CDR1

<400> SEQUENCE: 71

Gly Tyr Tyr Met Ser
1               5

<210> SEQ ID NO 72
<211> LENGTH: 16
<212> TYPE: PRT
<213> ORGANISM: Artificial Sequence
<220> FEATURE:
<223> OTHER INFORMATION: P2-A01 antibody VH CDR2

<400> SEQUENCE: 72

Ile Ile Tyr Pro Ser Gly Ser Thr Asp Tyr Ala Ser Trp Ala Lys Gly
1               5                   10                  15

<210> SEQ ID NO 73
```

-continued

```
<211> LENGTH: 15
<212> TYPE: PRT
<213> ORGANISM: Artificial Sequence
<220> FEATURE:
<223> OTHER INFORMATION: P2-A01 antibody VH CDR3

<400> SEQUENCE: 73

Val Ala Gly Tyr Val Gly Tyr Gly Tyr Glu Thr Phe Phe Asp Ile
1               5                   10                  15

<210> SEQ ID NO 74
<211> LENGTH: 11
<212> TYPE: PRT
<213> ORGANISM: Artificial Sequence
<220> FEATURE:
<223> OTHER INFORMATION: P2-A01 antibody VL CDR1

<400> SEQUENCE: 74

Leu Ala Ser Glu Asp Ile Tyr Ser Gly Ile Ser
1               5                   10

<210> SEQ ID NO 75
<211> LENGTH: 7
<212> TYPE: PRT
<213> ORGANISM: Artificial Sequence
<220> FEATURE:
<223> OTHER INFORMATION: P2-A01 antibody VL CDR2

<400> SEQUENCE: 75

Gly Ala Ser Asn Leu Glu Ser
1               5

<210> SEQ ID NO 76
<211> LENGTH: 14
<212> TYPE: PRT
<213> ORGANISM: Artificial Sequence
<220> FEATURE:
<223> OTHER INFORMATION: P2-A01 antibody VL CDR3

<400> SEQUENCE: 76

Leu Gly Gly Val Thr Tyr Ser Ser Thr Gly Thr His Leu Thr
1               5                   10

<210> SEQ ID NO 77
<211> LENGTH: 5
<212> TYPE: PRT
<213> ORGANISM: Artificial Sequence
<220> FEATURE:
<223> OTHER INFORMATION: P2-A03 antibody VH CDR1

<400> SEQUENCE: 77

Asn Tyr Asp Met Ser
1               5

<210> SEQ ID NO 78
<211> LENGTH: 16
<212> TYPE: PRT
<213> ORGANISM: Artificial Sequence
<220> FEATURE:
<223> OTHER INFORMATION: P2-A03 antibody VH CDR2

<400> SEQUENCE: 78

Phe Met Asp Thr Asp Gly Ser Ala Tyr Tyr Ala Thr Trp Ala Lys Gly
1               5                   10                  15

<210> SEQ ID NO 79
<211> LENGTH: 11
```

```
<212> TYPE: PRT
<213> ORGANISM: Artificial Sequence
<220> FEATURE:
<223> OTHER INFORMATION: P2-A03 antibody VH CDR3

<400> SEQUENCE: 79

Arg Gly Ser Ser Tyr Tyr Gly Gly Ile Asp Ile
1               5                   10

<210> SEQ ID NO 80
<211> LENGTH: 11
<212> TYPE: PRT
<213> ORGANISM: Artificial Sequence
<220> FEATURE:
<223> OTHER INFORMATION: P2-A03 antibody VL CDR1

<400> SEQUENCE: 80

Gln Ala Ser Gln Ser Ile Gly Gly Asn Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: P2-A03 antibody VL CDR2

<400> SEQUENCE: 81

Arg Ala Ser Thr Leu Ala Ser
1               5

<210> SEQ ID NO 82
<211> LENGTH: 14
<212> TYPE: PRT
<213> ORGANISM: Artificial Sequence
<220> FEATURE:
<223> OTHER INFORMATION: P2-A03 antibody VL CDR3

<400> SEQUENCE: 82

Gln Ser Pro Ala Tyr Asp Pro Ala Ala Tyr Val Gly Asn Ala
1               5                   10

<210> SEQ ID NO 83
<211> LENGTH: 5
<212> TYPE: PRT
<213> ORGANISM: Artificial Sequence
<220> FEATURE:
<223> OTHER INFORMATION: P2-F07 antibody VH CDR1

<400> SEQUENCE: 83

Ser Tyr Tyr Met Asn
1               5

<210> SEQ ID NO 84
<211> LENGTH: 16
<212> TYPE: PRT
<213> ORGANISM: Artificial Sequence
<220> FEATURE:
<223> OTHER INFORMATION: P2-F07 antibody VH CDR2

<400> SEQUENCE: 84

Ile Ile Tyr Pro Ser Gly Thr Thr Tyr Tyr Ala Gly Trp Ala Lys Gly
1               5                   10                  15

<210> SEQ ID NO 85
<211> LENGTH: 8
<212> TYPE: PRT
```

<213> ORGANISM: Artificial Sequence
<220> FEATURE:
<223> OTHER INFORMATION: P2-F07 antibody VH CDR3

<400> SEQUENCE: 85

Thr Val Ser Gly Tyr Phe Asp Ile
1               5

<210> SEQ ID NO 86
<211> LENGTH: 11
<212> TYPE: PRT
<213> ORGANISM: Artificial Sequence
<220> FEATURE:
<223> OTHER INFORMATION: P2-F07 antibody VL CDR1

<400> SEQUENCE: 86

Leu Ala Ser Glu Asp Ile Tyr Ser Ala Leu Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: P2-F07 antibody VL CDR2

<400> SEQUENCE: 87

Gly Thr Ser Asn Leu Glu Ser
1               5

<210> SEQ ID NO 88
<211> LENGTH: 9
<212> TYPE: PRT
<213> ORGANISM: Artificial Sequence
<220> FEATURE:
<223> OTHER INFORMATION: P2-F07 antibody VL CDR3

<400> SEQUENCE: 88

Gln Gly Tyr Ser Ser Tyr Pro Leu Thr
1               5

<210> SEQ ID NO 89
<211> LENGTH: 5
<212> TYPE: PRT
<213> ORGANISM: Artificial Sequence
<220> FEATURE:
<223> OTHER INFORMATION: P2-F11 antibody VH CDR1

<400> SEQUENCE: 89

Ser Tyr Gly Val Ser
1               5

<210> SEQ ID NO 90
<211> LENGTH: 16
<212> TYPE: PRT
<213> ORGANISM: Artificial Sequence
<220> FEATURE:
<223> OTHER INFORMATION: P2-F11 antibody VH CDR2

<400> SEQUENCE: 90

Tyr Ile Ala Asn Asn Tyr Asn Pro His Tyr Ala Ser Trp Ala Lys Gly
1               5                   10                  15

<210> SEQ ID NO 91
<211> LENGTH: 7
<212> TYPE: PRT
<213> ORGANISM: Artificial Sequence

```
<220> FEATURE:
<223> OTHER INFORMATION: P2-F11 antibody VH CDR3

<400> SEQUENCE: 91

Asp Asn Tyr Gly Met Asp Pro
1               5

<210> SEQ ID NO 92
<211> LENGTH: 13
<212> TYPE: PRT
<213> ORGANISM: Artificial Sequence
<220> FEATURE:
<223> OTHER INFORMATION: P2-F11 antibody VL CDR1

<400> SEQUENCE: 92

Gln Ala Ser Gln Ser Val Tyr Asn Asn Lys Asn Leu Ala
1               5                  10

<210> SEQ ID NO 93
<211> LENGTH: 7
<212> TYPE: PRT
<213> ORGANISM: Artificial Sequence
<220> FEATURE:
<223> OTHER INFORMATION: P2-F11 antibody VL CDR2

<400> SEQUENCE: 93

Ala Ala Ser Thr Leu Ala Ser
1               5

<210> SEQ ID NO 94
<211> LENGTH: 13
<212> TYPE: PRT
<213> ORGANISM: Artificial Sequence
<220> FEATURE:
<223> OTHER INFORMATION: P2-F11 antibody VL CDR3

<400> SEQUENCE: 94

Gln Gly Glu Phe Ser Cys Ser Ser Ala Asp Cys Asn Ala
1               5                  10

<210> SEQ ID NO 95
<211> LENGTH: 100
<212> TYPE: PRT
<213> ORGANISM: Artificial Sequence
<220> FEATURE:
<223> OTHER INFORMATION: M1 mutant

<400> SEQUENCE: 95

Gln Phe Leu Lys Glu Gly Gln Leu Ala Ala Gly Thr Cys Glu Val Ile
1               5                   10                  15

Ala Ala His Arg Asp Ser Ser Gln Pro Arg Arg Thr Ile Ala Arg Gln
                20                  25                  30

Thr Ala Arg Cys Ala Cys Arg Lys Gly Gln Ile Ala Gly Thr Thr Arg
            35                  40                  45

Ala Arg Pro Ala Cys Val Asp Ala Arg Ile Ile Lys Thr Lys Gln Trp
        50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100
```

```
<210> SEQ ID NO 96
<211> LENGTH: 100
<212> TYPE: PRT
<213> ORGANISM: Artificial Sequence
<220> FEATURE:
<223> OTHER INFORMATION: M2 mutant

<400> SEQUENCE: 96

Gln Phe Leu Lys Glu Gly Gln Leu Ala Ala Gly Thr Cys Glu Ile Val
1               5                   10                  15

Thr Leu Asp Arg Cys Cys Asn Lys Asn Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 97
<211> LENGTH: 100
<212> TYPE: PRT
<213> ORGANISM: Artificial Sequence
<220> FEATURE:
<223> OTHER INFORMATION: M3 mutant

<400> SEQUENCE: 97

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Ile Glu Glu Arg Ser Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 98
<211> LENGTH: 100
<212> TYPE: PRT
<213> ORGANISM: Artificial Sequence
<220> FEATURE:
<223> OTHER INFORMATION: M4 mutant

<400> SEQUENCE: 98

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Val Lys Cys Ser Cys Phe Pro Gly Gln Ile Ala Gly Thr Thr Arg
        35                  40                  45
```

```
Ala Arg Pro Ala Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 99
<211> LENGTH: 100
<212> TYPE: PRT
<213> ORGANISM: Artificial Sequence
<220> FEATURE:
<223> OTHER INFORMATION: M5 mutant

<400> SEQUENCE: 99

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Asn Lys Pro Ser Cys Val Asp Ala Arg Ile Ile Lys Thr Lys Gln Trp
    50                  55                  60

Cys Asp Met Leu Pro Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 100
<211> LENGTH: 100
<212> TYPE: PRT
<213> ORGANISM: Artificial Sequence
<220> FEATURE:
<223> OTHER INFORMATION: M6 mutant

<400> SEQUENCE: 100

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Leu Gln Arg Trp Trp
    50                  55                  60

Cys Gln Met Glu Leu Cys Leu Glu Gly Glu Gly Cys Asp Leu Leu Ile
65                  70                  75                  80

Asn Arg Ser Gly Trp Thr Cys Thr Gln Pro Gly Gly Arg Ile Lys Thr
                85                  90                  95

Thr Thr Val Ser
            100

<210> SEQ ID NO 101
<211> LENGTH: 100
<212> TYPE: PRT
```

```
<213> ORGANISM: Artificial Sequence
<220> FEATURE:
<223> OTHER INFORMATION: M7 mutant

<400> SEQUENCE: 101

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
50                  55                  60

Cys Asp Met Leu Pro Cys Leu Glu Gly Glu Glu Cys Lys Thr Leu Pro
65                  70                  75                  80

Asp Asn Ser Gly Trp Thr Cys Thr Gln Pro Gly Gly Arg Ile Lys Thr
                85                  90                  95

Thr Thr Val Ser
            100

<210> SEQ ID NO 102
<211> LENGTH: 101
<212> TYPE: PRT
<213> ORGANISM: Artificial Sequence
<220> FEATURE:
<223> OTHER INFORMATION: M8 mutant

<400> SEQUENCE: 102

Gln Phe Leu Lys Glu Gly Gln Leu Ala Ala Gly Thr Cys Glu Ile Val
1               5                   10                  15

Thr Leu Asp Arg Asp Ser Ser Gln Pro Arg Arg Thr Ile Ala Arg Gln
            20                  25                  30

Thr Ala Arg Cys Ala Cys Arg Lys Gly Gln Ile Ala Gly Thr Thr Arg
        35                  40                  45

Ala Arg Pro Ala Cys Val Asp Ala Arg Ile Ile Lys Thr Lys Gln Trp
50                  55                  60

Cys Asp Met Leu Pro Cys Leu Glu Gly Glu Gly Cys Asp Leu Leu Ile
65                  70                  75                  80

Asn Arg Ser Gly Trp Thr Cys Ser Cys Ser Ser Gly Asn Lys Ile Lys
                85                  90                  95

Thr Thr Thr Val Ser
            100

<210> SEQ ID NO 103
<211> LENGTH: 121
<212> TYPE: PRT
<213> ORGANISM: Artificial Sequence
<220> FEATURE:
<223> OTHER INFORMATION: P2-C12 antibody VH

<400> SEQUENCE: 103

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
        35                  40                  45

Tyr Ile Asn Trp Arg Gly Gly Thr Ser Tyr Ala Asn Trp Ala Lys Gly
50                  55                  60
```

```
Arg Phe Thr Ile Ser Lys Thr Ser Thr Thr Val Asp Leu Lys Met
 65                  70                  75                  80

Thr Ser Pro Thr Thr Glu Asp Thr Ala Thr Tyr Phe Cys Ala Arg Asp
                 85                  90                  95

Ala Ser Ser Gly Ala Ala Phe Gly Ser Tyr Gly Met Asp Pro Trp Gly
            100                 105                 110

Pro Gly Thr Leu Val Thr Val Ser Ser
        115                 120
```

<210> SEQ ID NO 104
<211> LENGTH: 118
<212> TYPE: PRT
<213> ORGANISM: Artificial Sequence
<220> FEATURE:
<223> OTHER INFORMATION: 13B4 antibody VH

<400> SEQUENCE: 104

```
Gln Val Gln Leu Gln Glu Ser Gly Pro Gly Leu Val Lys Pro Ser Gly
  1               5                  10                  15

Thr Leu Ser Leu Asn Cys Ala Val Ser Gly Gly Ser Ile Ser Ser Ser
             20                  25                  30

Asn Trp Trp Ser Trp Val Arg Gln Pro Pro Gly Lys Gly Leu Glu Trp
         35                  40                  45

Ile Gly Glu Ile Tyr His Gly Gly Thr Thr Asn Tyr Asn Pro Ser Leu
     50                  55                  60

Lys Gly Arg Val Thr Met Ser Val Asp Lys Thr Lys Asn Gln Phe Ser
 65                  70                  75                  80

Leu Arg Leu Ser Ser Val Thr Ala Val Asp Thr Ala Val Tyr Tyr Cys
                 85                  90                  95

Ala Arg Trp Gln Leu Val Gly Gly Leu Asp Val Trp Gly Gln Gly Thr
            100                 105                 110

Thr Val Thr Val Ser Ser
        115
```

<210> SEQ ID NO 105
<211> LENGTH: 123
<212> TYPE: PRT
<213> ORGANISM: Artificial Sequence
<220> FEATURE:
<223> OTHER INFORMATION: 13F7 antibody VH

<400> SEQUENCE: 105

```
Gln Val Gln Leu Gln Glu Trp Gly Ala Gly Leu Leu Lys Pro Ser Glu
  1               5                  10                  15

Thr Leu Ser Leu Thr Cys Ala Ile Asn Ala Glu Ser Phe Asn Gly Tyr
             20                  25                  30

Ser Trp Thr Trp Ile Arg Gln Thr Pro Gly Lys Gly Leu Glu Trp Ile
         35                  40                  45

Gly Glu Ile Ser His Phe Gly Ser Ala Asn Tyr Asn Pro Ser Leu Lys
     50                  55                  60

Ser Arg Ala Thr Ile Ser Ala Asp Lys Ser Lys Asn Gln Phe Ser Leu
 65                  70                  75                  80

Lys Leu Thr Ser Val Thr Ala Val Asp Thr Ala Val Tyr Tyr Cys Ala
                 85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser
```

<210> SEQ ID NO 106
<211> LENGTH: 120
<212> TYPE: PRT
<213> ORGANISM: Artificial Sequence
<220> FEATURE:
<223> OTHER INFORMATION: 15A9 antibody VH

<400> SEQUENCE: 106

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
            100                 105                 110

Gly Thr Thr Val Thr Val Ser Ser
        115                 120

<210> SEQ ID NO 107
<211> LENGTH: 116
<212> TYPE: PRT
<213> ORGANISM: Artificial Sequence
<220> FEATURE:
<223> OTHER INFORMATION: P1-A03 antibody VH

<400> SEQUENCE: 107

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Tyr
            20                  25                  30

Met Ser Trp Val Arg Gln Ala Pro Gly Glu Gly Leu Glu Trp Ile Gly
        35                  40                  45

Ile Ile Tyr Pro Ser Thr Thr Thr Tyr Tyr Ala Ser Trp Ala Lys Gly
    50                  55                  60

Arg Phe Thr Ile Ser Lys Thr Ser Ser Thr Thr Val Glu Leu Lys Met
65                  70                  75                  80

Thr Ser Leu Thr Thr Glu Asp Thr Ala Thr Tyr Phe Cys Ala Arg Gly
                85                  90                  95

Ser Asn Trp Ser Ser Gly Met Asn Leu Trp Gly Pro Gly Thr Leu Val
            100                 105                 110

Thr Val Ser Ser
        115

<210> SEQ ID NO 108
<211> LENGTH: 113
<212> TYPE: PRT
<213> ORGANISM: Artificial Sequence
<220> FEATURE:
<223> OTHER INFORMATION: P1-A08 antibody VH

<400> SEQUENCE: 108

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Val Tyr Pro Ser Gly Thr Thr Tyr Tyr Ala Asn Trp Ala Lys Gly
    50                  55                  60

Arg Phe Thr Ile Ser Thr Ala Ser Thr Thr Val Asp Leu Met Ile Thr
65              70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
            100                 105                 110

Ser

<210> SEQ ID NO 109
<211> LENGTH: 122
<212> TYPE: PRT
<213> ORGANISM: Artificial Sequence
<220> FEATURE:
<223> OTHER INFORMATION: P1-F02 antibody VH

<400> SEQUENCE: 109

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Tyr Tyr
            20                  25                  30

Met Gly Trp Val Arg Gln Ala Pro Gly Glu Gly Leu Glu Trp Ile Gly
        35                  40                  45

Ile Ile Tyr Ala Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Met Thr
65              70                  75                  80

Ser Leu Thr Thr Glu Asp Thr Ala Thr Tyr Phe Cys Ala Arg Ile Asp
                85                  90                  95

Ile Gly Val Gly Asp Tyr Gly Trp Ala Tyr Asp Arg Leu Asp Leu Trp
            100                 105                 110

Gly Gln Gly Thr Leu Val Thr Val Ser Ser
        115                 120

<210> SEQ ID NO 110
<211> LENGTH: 121
<212> TYPE: PRT
<213> ORGANISM: Artificial Sequence
<220> FEATURE:
<223> OTHER INFORMATION: P2-A01 antibody VH

<400> SEQUENCE: 110

Gln Glu Gln Leu Val Glu Ser Gly Gly Arg Leu Val Thr Pro Gly Thr
1               5                   10                  15

Pro Leu Thr Leu Ser Cys Thr Ala Ser Gly Phe Phe Leu Ser Gly Tyr
            20                  25                  30

Tyr Met Ser Trp Val Arg Gln Ala Pro Gly Lys Gly Leu Glu Trp Ile
        35                  40                  45

Gly Ile Ile Tyr Pro Ser Gly Ser Thr Asp Tyr Ala Ser Trp Ala Lys
    50                  55                  60
```

```
Gly Arg Phe Thr Ile Ser Lys Thr Ser Thr Val Asp Leu Lys Ile
65                  70                  75                  80

Thr Thr Pro Thr Thr Glu Asp Thr Ala Thr Tyr Phe Cys Ala Arg Val
                85                  90                  95

Ala Gly Tyr Val Gly Tyr Gly Tyr Glu Thr Phe Phe Asp Ile Trp Gly
            100                 105                 110

Pro Gly Thr Leu Val Thr Val Ser Leu
        115                 120

<210> SEQ ID NO 111
<211> LENGTH: 116
<212> TYPE: PRT
<213> ORGANISM: Artificial Sequence
<220> FEATURE:
<223> OTHER INFORMATION: P2-A03 antibody VH

<400> SEQUENCE: 111

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
                20                  25                  30

Met Ser Trp Val Arg Gln Ala Pro Gly Lys Gly Leu Glu Tyr Ile Gly
            35                  40                  45

Phe Met Asp Thr Asp Gly Ser Ala Tyr Tyr Ala Thr Trp Ala Lys Gly
        50                  55                  60

Arg Phe Thr Ile Ser Arg Thr Ser Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
            100                 105                 110

Thr Val Ser Leu
        115

<210> SEQ ID NO 112
<211> LENGTH: 113
<212> TYPE: PRT
<213> ORGANISM: Artificial Sequence
<220> FEATURE:
<223> OTHER INFORMATION: P2-F07 antibody VH

<400> SEQUENCE: 112

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
                20                  25                  30

Met Asn Trp Val Arg Gln Ala Pro Gly Lys Gly Leu Glu Trp Ile Gly
            35                  40                  45

Ile Ile Tyr Pro Ser Gly Thr Thr Tyr Tyr Ala Gly Trp Ala Lys Gly
        50                  55                  60

Arg Phe Thr Ile Ser Lys Thr Ser Thr Val Asp Leu Lys Ile Thr
65                  70                  75                  80

Ser Pro Thr Ser Glu Asp Thr Ala Thr Tyr Phe Cys Ala Arg Thr Val
                85                  90                  95

Ser Gly Tyr Phe Asp Ile Trp Gly Pro Gly Thr Leu Val Thr Val Ser
            100                 105                 110

Leu
```

```
<210> SEQ ID NO 113
<211> LENGTH: 114
<212> TYPE: PRT
<213> ORGANISM: Artificial Sequence
<220> FEATURE:
<223> OTHER INFORMATION: P2-F11 antibody VH

<400> SEQUENCE: 113

Gln Glu Gln Leu Val Glu Ser Gly Gly Arg Leu Val Thr Pro Gly Thr
1               5                   10                  15

Thr Leu Thr Leu Thr Cys Thr Val Ser Gly Phe Ser Leu Ser Ser Tyr
            20                  25                  30

Gly Val Ser Trp Val Arg Gln Ala Pro Gly Lys Gly Leu Glu Trp Ile
        35                  40                  45

Gly Tyr Ile Ala Asn Asn Tyr Asn Pro His Tyr Ala Ser Trp Ala Lys
    50                  55                  60

Gly Arg Phe Thr Ile Ser Lys Thr Ser Ser Thr Thr Val Asp Leu Lys
65                  70                  75                  80

Met Thr Ser Leu Thr Thr Glu Asp Thr Ala Thr Tyr Phe Cys Ala Arg
                85                  90                  95

Asp Asn Tyr Gly Met Asp Pro Trp Gly Pro Gly Thr Leu Val Thr Val
            100                 105                 110

Ser Ser

<210> SEQ ID NO 114
<211> LENGTH: 110
<212> TYPE: PRT
<213> ORGANISM: Artificial Sequence
<220> FEATURE:
<223> OTHER INFORMATION: P2-C12 antibody VL

<400> SEQUENCE: 114

Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Ser Thr Asn
                85                  90                  95

Val Trp Asn Ala Phe Gly Gly Thr Asn Val Glu Ile Lys
            100                 105                 110

<210> SEQ ID NO 115
<211> LENGTH: 106
<212> TYPE: PRT
<213> ORGANISM: Artificial Sequence
<220> FEATURE:
<223> OTHER INFORMATION: 13B4 antibody VL

<400> SEQUENCE: 115

Ser Tyr Glu Leu Thr Gln Pro Leu Ser Val Ser Val Ser Pro Gly Gln
1               5                   10                  15

Thr Ala Ser Ile Thr Cys Ser Gly Asp Lys Leu Gly Asn Val Tyr Ala
```

```
                      20                  25                  30

Ser Trp Tyr Gln Gln Lys Pro Gly Gln Ser Pro Thr Leu Val Ile Tyr
            35                  40                  45

Gln Asp Asn Lys Arg Pro Ser Gly Ile Pro Glu Arg Phe Ser Gly Ser
    50                  55                  60

Asn Ser Gly Lys Thr Ala Thr Leu Thr Ile Ser Gly Thr Gln Ala Leu
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 116
<211> LENGTH: 112
<212> TYPE: PRT
<213> ORGANISM: Artificial Sequence
<220> FEATURE:
<223> OTHER INFORMATION: 13F7 antibody VL

<400> SEQUENCE: 116

Asp Ile Val Met Thr Gln Thr Pro Leu Ser Leu Pro Val Ala Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Val Gln Lys Pro Gly Gln Pro
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Arg Gln Thr Pro Leu Thr Phe Gly Gly Gly Thr Lys Val Glu Ile Lys
            100                 105                 110

<210> SEQ ID NO 117
<211> LENGTH: 107
<212> TYPE: PRT
<213> ORGANISM: Artificial Sequence
<220> FEATURE:
<223> OTHER INFORMATION: 15A9 antibody VL

<400> SEQUENCE: 117

Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys
            100                 105
```

<210> SEQ ID NO 118
<211> LENGTH: 110
<212> TYPE: PRT
<213> ORGANISM: Artificial Sequence
<220> FEATURE:
<223> OTHER INFORMATION: P1-A03 antibody VL

<400> SEQUENCE: 118

Glu Leu Val Met Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Glu Lys Pro Thr Leu Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Thr Gly Leu Thr Phe Gly Ala Gly Thr Asn Val Glu Ile Lys
            100                 105                 110

<210> SEQ ID NO 119
<211> LENGTH: 110
<212> TYPE: PRT
<213> ORGANISM: Artificial Sequence
<220> FEATURE:
<223> OTHER INFORMATION: P1-A08 antibody VL

<400> SEQUENCE: 119

Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Asn
                85                  90                  95

Tyr Gln Tyr Val Phe Gly Gly Gly Thr Gln Leu Thr Val Thr
            100                 105                 110

<210> SEQ ID NO 120
<211> LENGTH: 108
<212> TYPE: PRT
<213> ORGANISM: Artificial Sequence
<220> FEATURE:
<223> OTHER INFORMATION: P1-F02 antibody VL

<400> SEQUENCE: 120

Glu Leu Asp Met Thr Gln Thr Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile

```
                35                  40                  45
Tyr Gly Ala Ser Asn Leu Glu Ser Gly Val Pro Pro Arg Phe Ser Gly
         50                  55                  60
Ser Gly Ser Gly Thr Asp Tyr Thr Leu Thr Ile Gly Gly Val Gln Ala
 65                  70                  75                  80
Glu Asp Ala Ala Thr Tyr Tyr Cys Leu Gly Gly Tyr Ser Tyr Ser Ser
                 85                  90                  95
Ile Thr Phe Gly Ala Gly Thr Asn Val Glu Ile Lys
            100                 105
```

<210> SEQ ID NO 121
<211> LENGTH: 112
<212> TYPE: PRT
<213> ORGANISM: Artificial Sequence
<220> FEATURE:
<223> OTHER INFORMATION: P2-A01 antibody VL

<400> SEQUENCE: 121

```
Glu Leu Val Met Thr Gln Thr Pro Pro Ser Leu Ser Ala Ser Val Gly
 1               5                  10                  15
Glu Thr Val Arg Ile Arg Cys Leu Ala Ser Glu Asp Ile Tyr Ser Gly
             20                  25                  30
Ile Ser Trp Tyr Gln Gln Lys Pro Gly Lys Pro Thr Leu Leu Ile
         35                  40                  45
Tyr Gly Ala Ser Asn Leu Glu Ser Gly Val Pro Pro Arg Phe Ser Gly
         50                  55                  60
Ser Gly Ser Gly Ser Asp Tyr Thr Leu Thr Ile Gly Gly Val Gln Ala
 65                  70                  75                  80
Glu Asp Ala Ala Thr Tyr Tyr Cys Leu Gly Gly Val Thr Tyr Ser Ser
                 85                  90                  95
Thr Gly Thr His Leu Thr Phe Gly Ala Gly Thr Asn Val Glu Ile Lys
            100                 105                 110
```

<210> SEQ ID NO 122
<211> LENGTH: 112
<212> TYPE: PRT
<213> ORGANISM: Artificial Sequence
<220> FEATURE:
<223> OTHER INFORMATION: P2-A03 antibody VL

<400> SEQUENCE: 122

```
Glu Leu Asp Leu Thr Gln Thr Pro Ala Ser Val Ser Glu Pro Val Gly
 1               5                  10                  15
Gly Thr Val Thr Ile Lys Cys Gln Ala Ser Gln Ser Ile Gly Gly Asn
             20                  25                  30
Leu Ala Trp Tyr Gln Gln Lys Pro Gly Gln Pro Pro Lys Leu Leu Ile
         35                  40                  45
Tyr Arg Ala Ser Thr Leu Ala Ser Gly Val Pro Ser Arg Phe Lys Gly
         50                  55                  60
Ser Gly Ser Gly Thr Asp Phe Thr Leu Thr Ile Ser Asp Leu Glu Cys
 65                  70                  75                  80
Ala Asp Ala Ala Thr Tyr Tyr Cys Gln Ser Pro Ala Tyr Asp Pro Ala
                 85                  90                  95
Ala Tyr Val Gly Asn Ala Phe Gly Gly Gly Thr Glu Leu Glu Ile Leu
            100                 105                 110
```

<210> SEQ ID NO 123
<211> LENGTH: 107

```
<212> TYPE: PRT
<213> ORGANISM: Artificial Sequence
<220> FEATURE:
<223> OTHER INFORMATION: P2-F07 antibody VL

<400> SEQUENCE: 123

Glu Leu Asp Leu Thr Gln Thr Pro Pro Ser Leu Ser Ala Ser Val Gly
1               5                   10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Thr Leu Leu Ile
        35                  40                  45

Ser Gly Thr Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys
                100                 105

<210> SEQ ID NO 124
<211> LENGTH: 113
<212> TYPE: PRT
<213> ORGANISM: Artificial Sequence
<220> FEATURE:
<223> OTHER INFORMATION: P2-F11 antibody VL

<400> SEQUENCE: 124

Glu Leu Asp Leu Thr Gln Thr Pro Ser Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Gln Gly Glu Phe Ser Cys
                85                  90                  95

Ser Ser Ala Asp Cys Asn Ala Phe Gly Gly Gly Thr Glu Leu Glu Ile
                100                 105                 110

Leu

<210> SEQ ID NO 125
<211> LENGTH: 20
<212> TYPE: PRT
<213> ORGANISM: Artificial Sequence
<220> FEATURE:
<223> OTHER INFORMATION: F5

<400> SEQUENCE: 125

Ser Asp Met Leu Pro Ser Leu Glu Gly Glu Ser Asp Leu Leu Ile
1               5                   10                  15

Asn Arg Ser Gly
            20

<210> SEQ ID NO 126
```

```
<211> LENGTH: 20
<212> TYPE: PRT
<213> ORGANISM: Artificial Sequence
<220> FEATURE:
<223> OTHER INFORMATION: F5-1 (#1)

<400> SEQUENCE: 126

Ser Asp Met Leu Pro Ser Leu Glu Gly Glu Ala Ser Asp Leu Leu Ile
1               5                   10                  15

Asn Arg Ser Gly
            20

<210> SEQ ID NO 127
<211> LENGTH: 20
<212> TYPE: PRT
<213> ORGANISM: Artificial Sequence
<220> FEATURE:
<223> OTHER INFORMATION: F5-2 (#2)

<400> SEQUENCE: 127

Ser Asp Met Leu Pro Ser Leu Glu Gly Glu Gly Ser Ala Leu Leu Ile
1               5                   10                  15

Asn Arg Ser Gly
            20

<210> SEQ ID NO 128
<211> LENGTH: 20
<212> TYPE: PRT
<213> ORGANISM: Artificial Sequence
<220> FEATURE:
<223> OTHER INFORMATION: F5-3 (#3)

<400> SEQUENCE: 128

Ser Asp Met Leu Pro Ser Leu Glu Gly Glu Gly Ser Asp Ala Leu Ile
1               5                   10                  15

Asn Arg Ser Gly
            20

<210> SEQ ID NO 129
<211> LENGTH: 20
<212> TYPE: PRT
<213> ORGANISM: Artificial Sequence
<220> FEATURE:
<223> OTHER INFORMATION: F5-4 (#4)

<400> SEQUENCE: 129

Ser Asp Met Leu Pro Ser Leu Glu Gly Glu Gly Ser Asp Leu Leu Ala
1               5                   10                  15

Asn Arg Ser Gly
            20

<210> SEQ ID NO 130
<211> LENGTH: 20
<212> TYPE: PRT
<213> ORGANISM: Artificial Sequence
<220> FEATURE:
<223> OTHER INFORMATION: F5-5 (#5)

<400> SEQUENCE: 130

Ser Asp Met Leu Pro Ser Leu Ala Gly Glu Gly Ser Asp Leu Leu Ile
1               5                   10                  15

Asn Arg Ser Gly
            20
```

-continued

```
<210> SEQ ID NO 131
<211> LENGTH: 20
<212> TYPE: PRT
<213> ORGANISM: Artificial Sequence
<220> FEATURE:
<223> OTHER INFORMATION: F5-6 (#6)

<400> SEQUENCE: 131

Ser Asp Met Leu Pro Ser Leu Glu Gly Ala Gly Ser Asp Leu Leu Ile
1               5                   10                  15

Asn Arg Ser Gly
            20

<210> SEQ ID NO 132
<211> LENGTH: 20
<212> TYPE: PRT
<213> ORGANISM: Artificial Sequence
<220> FEATURE:
<223> OTHER INFORMATION: F5-7 (#7)

<400> SEQUENCE: 132

Ser Asp Met Leu Pro Ser Leu Glu Gly Glu Gly Ser Asp Leu Leu Ile
1               5                   10                  15

Ala Arg Ser Gly
            20

<210> SEQ ID NO 133
<211> LENGTH: 20
<212> TYPE: PRT
<213> ORGANISM: Artificial Sequence
<220> FEATURE:
<223> OTHER INFORMATION: F5-8 (#8)

<400> SEQUENCE: 133

Ser Asp Met Leu Pro Ser Leu Glu Gly Glu Gly Ser Asp Leu Leu Ile
1               5                   10                  15

Asn Ala Ser Gly
            20

<210> SEQ ID NO 134
<211> LENGTH: 5
<212> TYPE: PRT
<213> ORGANISM: Artificial Sequence
<220> FEATURE:
<223> OTHER INFORMATION: EP1 Epitope

<400> SEQUENCE: 134

Ile Val Thr Leu Asp
1               5

<210> SEQ ID NO 135
<211> LENGTH: 5
<212> TYPE: PRT
<213> ORGANISM: Artificial Sequence
<220> FEATURE:
<223> OTHER INFORMATION: EP2 Epitope

<400> SEQUENCE: 135

Asp Ser Ser Gln Pro
1               5

<210> SEQ ID NO 136
<211> LENGTH: 5
<212> TYPE: PRT
<213> ORGANISM: Artificial Sequence
<220> FEATURE:
```

```
<223> OTHER INFORMATION: EP3 Epitope

<400> SEQUENCE: 136

Arg Thr Ile Ala Arg
1               5

<210> SEQ ID NO 137
<211> LENGTH: 7
<212> TYPE: PRT
<213> ORGANISM: Artificial Sequence
<220> FEATURE:
<223> OTHER INFORMATION: EP4 Epitope

<400> SEQUENCE: 137

Ala Arg Cys Ala Cys Arg Lys
1               5

<210> SEQ ID NO 138
<211> LENGTH: 4
<212> TYPE: PRT
<213> ORGANISM: Artificial Sequence
<220> FEATURE:
<223> OTHER INFORMATION: EP5 Epitope

<400> SEQUENCE: 138

Ala Arg Pro Ala
1

<210> SEQ ID NO 139
<211> LENGTH: 9
<212> TYPE: PRT
<213> ORGANISM: Artificial Sequence
<220> FEATURE:
<223> OTHER INFORMATION: EP6 Epitope

<400> SEQUENCE: 139

Lys Thr Lys Gln Trp Cys Asp Met Leu
1               5

<210> SEQ ID NO 140
<211> LENGTH: 8
<212> TYPE: PRT
<213> ORGANISM: Artificial Sequence
<220> FEATURE:
<223> OTHER INFORMATION: EP7 Epitope

<400> SEQUENCE: 140

Gly Cys Asp Leu Leu Ile Asn Arg
1               5

<210> SEQ ID NO 141
<211> LENGTH: 8
<212> TYPE: PRT
<213> ORGANISM: Artificial Sequence
<220> FEATURE:
<223> OTHER INFORMATION: EP8 Epitope

<400> SEQUENCE: 141

Thr Cys Thr Gln Pro Gly Gly Arg
1               5

<210> SEQ ID NO 142
<211> LENGTH: 100
<212> TYPE: PRT
<213> ORGANISM: Artificial Sequence
<220> FEATURE:
<223> OTHER INFORMATION: Wild-type FAM19A5 Isoform 2 (no signal peptide)
```

<400> SEQUENCE: 142

| Gln | Phe | Leu | Lys | Glu | Gly | Gln | Leu | Ala | Ala | Gly | Thr | Cys | Glu | Ile | Val |
|---|---|---|---|---|---|---|---|---|---|---|---|---|---|---|---|
| 1 | | | | 5 | | | | | 10 | | | | | 15 | |

| Thr | Leu | Asp | Arg | Asp | Ser | Ser | Gln | Pro | Arg | Arg | Thr | Ile | Ala | Arg | Gln |
|---|---|---|---|---|---|---|---|---|---|---|---|---|---|---|---|
| | | | 20 | | | | | 25 | | | | | 30 | | |

| Thr | Ala | Arg | Cys | Ala | Cys | Arg | Lys | Gly | Gln | Ile | Ala | Gly | Thr | Thr | Arg |
|---|---|---|---|---|---|---|---|---|---|---|---|---|---|---|---|
| | | 35 | | | | | 40 | | | | | 45 | | | |

| Ala | Arg | Pro | Ala | Cys | Val | Asp | Ala | Arg | Ile | Ile | Lys | Thr | Lys | Gln | Trp |
|---|---|---|---|---|---|---|---|---|---|---|---|---|---|---|---|
| | 50 | | | | | 55 | | | | | 60 | | | | |

| Cys | Asp | Met | Leu | Pro | Cys | Leu | Glu | Gly | Glu | Gly | Cys | Asp | Leu | Leu | Ile |
|---|---|---|---|---|---|---|---|---|---|---|---|---|---|---|---|
| 65 | | | | 70 | | | | | 75 | | | | | 80 | |

| Asn | Arg | Ser | Gly | Trp | Thr | Cys | Thr | Gln | Pro | Gly | Gly | Arg | Ile | Lys | Thr |
|---|---|---|---|---|---|---|---|---|---|---|---|---|---|---|---|
| | | | | 85 | | | | | 90 | | | | | 95 | |

| Thr | Thr | Val | Ser |
|---|---|---|---|
| | | | 100 |

<210> SEQ ID NO 143
<211> LENGTH: 363
<212> TYPE: DNA
<213> ORGANISM: Artificial Sequence
<220> FEATURE:
<223> OTHER INFORMATION: P2-C12 anitbody VH

<400> SEQUENCE: 143

```
cagtcgctgg aggagtccgg gggtcgcctg gtcacgcctg ggacacccct gacactcacc      60
tgcaccgtct ctggattctc cctcagtacc tatgcagtga cctgggtccg ccaggctcca     120
gggaaggggc tggaatggat cggatacatt aattggcgtg gtgggacatc ctacgcgaac     180
tgggcgaaag gccgattcac catctccaaa acctcgtcga ccacggtgga tctgaaaatg     240
accagtccga caaccgagga cacggccacc tatttctgtg ccagagatgc tagtagtggt     300
gctgcttttg gtcttacgg catggacccc tggggcccag gaccctcgt caccgtctct     360
tca                                                                  363
```

<210> SEQ ID NO 144
<211> LENGTH: 330
<212> TYPE: DNA
<213> ORGANISM: Artificial Sequence
<220> FEATURE:
<223> OTHER INFORMATION: P2-C12 anitbody VH

<400> SEQUENCE: 144

```
gagctcgata tgacccagac tccatcctcc gtgtctgcag ctgtgggagg cacagtcacc      60
atcaagtgcc aggccagtca gagcattagt agctacttat cctggtatca gcagaaacca     120
gggcagcctc ccaagctcct gatctatgaa gcatccaaac tggcctctgg ggtcccatcg     180
cggttcagcg gcagtggata tgggacagag ttcactctca ccatcagcga cctggagtgt     240
gccgatgctg ccacttacta ctgtcaacag ggttatagta gtactaatgt ttggaatgct     300
ttcggcggag gcaccaatgt ggaaatcaaa                                      330
```

<210> SEQ ID NO 145
<211> LENGTH: 451
<212> TYPE: PRT
<213> ORGANISM: Artificial Sequence
<220> FEATURE:
<223> OTHER INFORMATION: P2-C12 HC

<400> SEQUENCE: 145

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Val Thr Trp Val Arg Gln Ala Pro Gly Lys Gly Leu Glu Trp Ile Gly
            35                  40                  45

Tyr Ile Asn Trp Arg Gly Gly Thr Ser Tyr Ala Asn Trp Ala Lys Gly
        50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Asp
                85                  90                  95

Ala Ser Ser Gly Ala Ala Phe Gly Ser Tyr Gly Met Asp Pro Trp Gly
                100                 105                 110

Pro Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 146
<211> LENGTH: 448
<212> TYPE: PRT
<213> ORGANISM: Artificial Sequence
<220> FEATURE:
<223> OTHER INFORMATION: 13B4 HC

<400> SEQUENCE: 146

Gln Val Gln Leu Gln Glu Ser Gly Pro Gly Leu Val Lys Pro Ser Gly
1               5                   10                  15

Thr Leu Ser Leu Asn Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Gly Gly Thr Thr Asn Tyr Asn Pro Ser Leu
    50                  55                  60

Lys Gly Arg Val Thr Met Ser Val Asp Lys Thr Lys Asn Gln Phe Ser
65                  70                  75                  80

Leu Arg Leu Ser Ser Val Thr Ala Val Asp Thr Ala Val Tyr Tyr Cys
                85                  90                  95

Ala Arg Trp Gln Leu Val Gly Gly Leu Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

```
<210> SEQ ID NO 147
<211> LENGTH: 453
<212> TYPE: PRT
<213> ORGANISM: Artificial Sequence
<220> FEATURE:
<223> OTHER INFORMATION: 13F7 HC

<400> SEQUENCE: 147

Gln Val Gln Leu Gln Glu Trp Gly Ala Gly Leu Leu Lys Pro Ser Glu
1               5                   10                  15

Thr Leu Ser Leu Thr Cys Ala Ile Asn Ala Glu Ser Phe Asn Gly Tyr
            20                  25                  30

Ser Trp Thr Trp Ile Arg Gln Thr Pro Gly Lys Gly Leu Glu Trp Ile
        35                  40                  45

Gly Glu Ile Ser His Phe Gly Ser Ala Asn Tyr Asn Pro Ser Leu Lys
    50                  55                  60

Ser Arg Ala Thr Ile Ser Ala Asp Lys Ser Lys Asn Gln Phe Ser Leu
65                  70                  75                  80

Lys Leu Thr Ser Val Thr Ala Val Asp Thr Ala Val Tyr Tyr Cys Ala
                85                  90                  95

Arg Ala Leu Arg Gly Thr Tyr Ser Arg Phe Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
            450

<210> SEQ ID NO 148
<211> LENGTH: 450
<212> TYPE: PRT
<213> ORGANISM: Artificial Sequence
<220> FEATURE:
<223> OTHER INFORMATION: 15A9 HC

<400> SEQUENCE: 148

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Pro Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Lys Ser Val Thr Ala Val Asp Thr Ala Val Tyr Tyr Cys Ala
                85                  90                  95

Arg Val Asn Pro Phe Gly Tyr Tyr Tyr Ala Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 149
<211> LENGTH: 446
<212> TYPE: PRT
<213> ORGANISM: Artificial Sequence
<220> FEATURE:
<223> OTHER INFORMATION: P1-A03 HC

<400> SEQUENCE: 149

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asp Tyr
            20                  25                  30

Met Ser Trp Val Arg Gln Ala Pro Gly Glu Gly Leu Glu Trp Ile Gly
        35                  40                  45
```

Ile Ile Tyr Pro Ser Thr Thr Thr Tyr Tyr Ala Ser Trp Ala Lys Gly
 50                  55                  60

Arg Phe Thr Ile Ser Lys Thr Ser Ser Thr Thr Val Glu Leu Lys Met
 65                  70                  75                  80

Thr Ser Leu Thr Thr Glu Asp Thr Ala Thr Tyr Phe Cys Ala Arg Gly
                 85                  90                  95

Ser Asn Trp Ser Ser Gly Met Asn Leu Trp Gly Pro Gly Thr Leu Val
             100                 105                 110

Thr Val Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 150
<211> LENGTH: 443
<212> TYPE: PRT

<210> ORGANISM: Artificial Sequence
<220> FEATURE:
<223> OTHER INFORMATION: P1-A08 HC

<400> SEQUENCE: 150

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Thr Tyr Tyr
            20                  25                  30

Met Ser Trp Val Arg Gln Ala Pro Gly Lys Gly Leu Glu Trp Ile Gly
        35                  40                  45

Ile Val Tyr Pro Ser Gly Thr Thr Tyr Tyr Ala Asn Trp Ala Lys Gly
    50                  55                  60

Arg Phe Thr Ile Ser Thr Ala Ser Thr Thr Val Asp Leu Met Ile Thr
65                  70                  75                  80

Ser Pro Thr Thr Glu Asp Thr Ala Thr Tyr Phe Cys Ala Arg Gly Asp
                85                  90                  95

Ser Phe Gly Tyr Gly Leu Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe

```
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
                435                 440

<210> SEQ ID NO 151
<211> LENGTH: 452
<212> TYPE: PRT
<213> ORGANISM: Artificial Sequence
<220> FEATURE:
<223> OTHER INFORMATION: P1-F02 HC

<400> SEQUENCE: 151

Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Asn Tyr Tyr
                20                  25                  30
Met Gly Trp Val Arg Gln Ala Pro Gly Glu Gly Leu Glu Trp Ile Gly
                35                  40                  45
Ile Ile Tyr Ala Ser Gly Ser Thr Tyr Tyr Ala Ser Trp Ala Lys Gly
    50                  55                  60
Arg Phe Thr Ile Ser Lys Thr Ser Thr Thr Val Asp Leu Lys Met Thr
65                  70                  75                  80
Ser Leu Thr Thr Glu Asp Thr Ala Thr Tyr Phe Cys Ala Arg Ile Asp
                85                  90                  95
Ile Gly Val Gly Asp Tyr Gly Trp Ala Tyr Asp Arg Leu Asp Leu Trp
                100                 105                 110
Gly Gln Gly Thr Leu Val Thr Val Ser Ser Ala Ser Thr Lys Gly Pro
                115                 120                 125
Ser Val Phe Pro Leu Ala Pro Ser Ser Lys Ser Thr Ser Gly Gly Thr
                130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Lys Val Glu Pro Lys Ser
                210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
                290                 295                 300
Tyr Arg Val Val Ser Val Leu Thr Val Leu His Gln Asp Trp Leu Asn
```

```
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Arg Glu Glu Met Thr Lys Asn Gln Val
                355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly Lys
    450

<210> SEQ ID NO 152
<211> LENGTH: 451
<212> TYPE: PRT
<213> ORGANISM: Artificial Sequence
<220> FEATURE:
<223> OTHER INFORMATION: P2-A01 HC

<400> SEQUENCE: 152

Gln Glu Gln Leu Val Glu Ser Gly Gly Arg Leu Val Thr Pro Gly Thr
1               5                   10                  15
Pro Leu Thr Leu Ser Cys Thr Ala Ser Gly Phe Phe Leu Ser Gly Tyr
                20                  25                  30
Tyr Met Ser Trp Val Arg Gln Ala Pro Gly Lys Gly Leu Glu Trp Ile
                35                  40                  45
Gly Ile Ile Tyr Pro Ser Gly Ser Thr Asp Tyr Ala Ser Trp Ala Lys
    50                  55                  60
Gly Arg Phe Thr Ile Ser Lys Thr Ser Thr Thr Val Asp Leu Lys Ile
65                  70                  75                  80
Thr Thr Pro Thr Thr Glu Asp Thr Ala Thr Tyr Phe Cys Ala Arg Val
                85                  90                  95
Ala Gly Tyr Val Gly Tyr Gly Tyr Glu Thr Phe Phe Asp Ile Trp Gly
                100                 105                 110
Pro Gly Thr Leu Val Thr Val Ser Leu Ala Ser Thr Lys Gly Pro Ser
                115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Lys Val Glu Pro Lys Ser Cys
```

-continued

```
            210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 153
<211> LENGTH: 446
<212> TYPE: PRT
<213> ORGANISM: Artificial Sequence
<220> FEATURE:
<223> OTHER INFORMATION: P2-A03 HC

<400> SEQUENCE: 153

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Asp
                20                  25                  30

Met Ser Trp Val Arg Gln Ala Pro Gly Lys Gly Leu Glu Tyr Ile Gly
            35                  40                  45

Phe Met Asp Thr Asp Gly Ser Ala Tyr Tyr Ala Thr Trp Ala Lys Gly
        50                  55                  60

Arg Phe Thr Ile Ser Arg Thr Ser Thr Val Asp Leu Lys Met Thr
65                  70                  75                  80

Ser Pro Thr Thr Glu Asp Thr Ala Thr Tyr Phe Cys Ala Arg Arg Gly
                85                  90                  95

Ser Ser Tyr Tyr Gly Gly Ile Asp Ile Trp Gly Pro Gly Thr Pro Val
                100                 105                 110

Thr Val Ser Leu Ala Ser Thr Lys Gly Pro Ser Val Phe Pro Leu Ala
```

115                 120                 125
Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 154
<211> LENGTH: 443
<212> TYPE: PRT
<213> ORGANISM: Artificial Sequence
<220> FEATURE:
<223> OTHER INFORMATION: P2-F07 HC

<400> SEQUENCE: 154

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly

```
                35                  40                  45
Ile Ile Tyr Pro Ser Gly Thr Thr Tyr Ala Gly Trp Ala Lys Gly
 50                  55                  60

Arg Phe Thr Ile Ser Lys Thr Ser Thr Val Asp Leu Lys Ile Thr
 65                  70                  75                  80

Ser Pro Thr Ser Glu Asp Thr Ala Thr Tyr Phe Cys Ala Arg Thr Val
                 85                  90                  95

Ser Gly Tyr Phe Asp Ile Trp Gly Pro Gly Thr Leu Val Thr Val Ser
                100                 105                 110

Leu Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
                195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
                275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 155
```

```
<211> LENGTH: 444
<212> TYPE: PRT
<213> ORGANISM: Artificial Sequence
<220> FEATURE:
<223> OTHER INFORMATION: P2-F11 HC

<400> SEQUENCE: 155
```

| Gln | Glu | Gln | Leu | Val | Glu | Ser | Gly | Gly | Arg | Leu | Val | Thr | Pro | Gly | Thr |
|---|---|---|---|---|---|---|---|---|---|---|---|---|---|---|---|
| 1 | | | | 5 | | | | | 10 | | | | | 15 | |

| Thr | Leu | Thr | Leu | Thr | Cys | Thr | Val | Ser | Gly | Phe | Ser | Leu | Ser | Ser | Tyr |
|---|---|---|---|---|---|---|---|---|---|---|---|---|---|---|---|
| | | | 20 | | | | | 25 | | | | | 30 | | |

| Gly | Val | Ser | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Tyr | Ile | Ala | Asn | Asn | Tyr | Asn | Pro | His | Tyr | Ala | Ser | Trp | Ala | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Lys | Thr | Ser | Thr | Thr | Val | Asp | Leu | Lys |
|---|---|---|---|---|---|---|---|---|---|---|---|---|---|---|
| 65 | | | | | 70 | | | | | 75 | | | | 80 |

| Met | Thr | Ser | Leu | Thr | Thr | Glu | Asp | Thr | Ala | Thr | Tyr | Phe | Cys | Ala | Arg |
|---|---|---|---|---|---|---|---|---|---|---|---|---|---|---|---|
| | | | | 85 | | | | | 90 | | | | | 95 | |

| Asp | Asn | Tyr | Gly | Met | Asp | Pro | Trp | Gly | Pro | Gly | Thr | Leu | Val | Thr | Val |
|---|---|---|---|---|---|---|---|---|---|---|---|---|---|---|---|
| | | | 100 | | | | | 105 | | | | | 110 | | |

| Ser | Ser | Ala | Ser | Thr | Lys | Gly | Pro | Ser | Val | Phe | Pro | Leu | Ala | Pro | Ser |
|---|---|---|---|---|---|---|---|---|---|---|---|---|---|---|---|
| | | 115 | | | | | 120 | | | | | 125 | | | |

| Ser | Lys | Ser | Thr | Ser | Gly | Gly | Thr | Ala | Ala | Leu | Gly | Cys | Leu | Val | Lys |
|---|---|---|---|---|---|---|---|---|---|---|---|---|---|---|---|
| | 130 | | | | | 135 | | | | | 140 | | | | |

| Asp | Tyr | Phe | Pro | Glu | Pro | Val | Thr | Val | Ser | Trp | Asn | Ser | Gly | Ala | Leu |
|---|---|---|---|---|---|---|---|---|---|---|---|---|---|---|---|
| 145 | | | | | 150 | | | | | 155 | | | | | 160 |

| Thr | Ser | Gly | Val | His | Thr | Phe | Pro | Ala | Val | Leu | Gln | Ser | Ser | Gly | Leu |
|---|---|---|---|---|---|---|---|---|---|---|---|---|---|---|---|
| | | | | 165 | | | | | 170 | | | | | 175 | |

| Tyr | Ser | Leu | Ser | Ser | Val | Val | Thr | Val | Pro | Ser | Ser | Ser | Leu | Gly | Thr |
|---|---|---|---|---|---|---|---|---|---|---|---|---|---|---|---|
| | | | 180 | | | | | 185 | | | | | 190 | | |

| Gln | Thr | Tyr | Ile | Cys | Asn | Val | Asn | His | Lys | Pro | Ser | Asn | Thr | Lys | Val |
|---|---|---|---|---|---|---|---|---|---|---|---|---|---|---|---|
| | | 195 | | | | | 200 | | | | | 205 | | | |

| Asp | Lys | Lys | Val | Glu | Pro | Lys | Ser | Cys | Asp | Lys | Thr | His | Thr | Cys | Pro |
|---|---|---|---|---|---|---|---|---|---|---|---|---|---|---|---|
| | 210 | | | | | 215 | | | | | 220 | | | | |

| Pro | Cys | Pro | Ala | Pro | Glu | Leu | Leu | Gly | Gly | Pro | Ser | Val | Phe | Leu | Phe |
|---|---|---|---|---|---|---|---|---|---|---|---|---|---|---|---|
| 225 | | | | | 230 | | | | | 235 | | | | | 240 |

| Pro | Pro | Lys | Pro | Lys | Asp | Thr | Leu | Met | Ile | Ser | Arg | Thr | Pro | Glu | Val |
|---|---|---|---|---|---|---|---|---|---|---|---|---|---|---|---|
| | | | | 245 | | | | | 250 | | | | | 255 | |

| Thr | Cys | Val | Val | Val | Asp | Val | Ser | His | Glu | Asp | Pro | Glu | Val | Lys | Phe |
|---|---|---|---|---|---|---|---|---|---|---|---|---|---|---|---|
| | | | | 260 | | | | | 265 | | | | | 270 | |

| Asn | Trp | Tyr | Val | Asp | Gly | Val | Glu | Val | His | Asn | Ala | Lys | Thr | Lys | Pro |
|---|---|---|---|---|---|---|---|---|---|---|---|---|---|---|---|
| | | 275 | | | | | 280 | | | | | 285 | | | |

| Arg | Glu | Glu | Gln | Tyr | Asn | Ser | Thr | Tyr | Arg | Val | Val | Ser | Val | Leu | Thr |
|---|---|---|---|---|---|---|---|---|---|---|---|---|---|---|---|
| | 290 | | | | | 295 | | | | | 300 | | | | |

| Val | Leu | His | Gln | Asp | Trp | Leu | Asn | Gly | Lys | Glu | Tyr | Lys | Cys | Lys | Val |
|---|---|---|---|---|---|---|---|---|---|---|---|---|---|---|---|
| 305 | | | | | 310 | | | | | 315 | | | | | 320 |

| Ser | Asn | Lys | Ala | Leu | Pro | Ala | Pro | Ile | Glu | Lys | Thr | Ile | Ser | Lys | Ala |
|---|---|---|---|---|---|---|---|---|---|---|---|---|---|---|---|
| | | | | 325 | | | | | 330 | | | | | 335 | |

| Lys | Gly | Gln | Pro | Arg | Glu | Pro | Gln | Val | Tyr | Thr | Leu | Pro | Pro | Ser | Arg |
|---|---|---|---|---|---|---|---|---|---|---|---|---|---|---|---|
| | | | 340 | | | | | 345 | | | | | 350 | | |

| Glu | Glu | Met | Thr | Lys | Asn | Gln | Val | Ser | Leu | Thr | Cys | Leu | Val | Lys | Gly |
|---|---|---|---|---|---|---|---|---|---|---|---|---|---|---|---|
| | | | 355 | | | | | 360 | | | | | 365 | | |

| Phe | Tyr | Pro | Ser | Asp | Ile | Ala | Val | Glu | Trp | Glu | Ser | Asn | Gly | Gln | Pro |
|---|---|---|---|---|---|---|---|---|---|---|---|---|---|---|---|
| | 370 | | | | | 375 | | | | | 380 | | | | |

```
Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 156
<211> LENGTH: 217
<212> TYPE: PRT
<213> ORGANISM: Artificial Sequence
<220> FEATURE:
<223> OTHER INFORMATION: P2-C12 LC

<400> SEQUENCE: 156

Glu Leu Asp Met Thr Gln Thr Pro Ser Ser Val Ser Ala Ala Val Gly
1               5                   10                  15

Gly Thr Val Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gln Gly Tyr Ser Ser Thr Asn
                85                  90                  95

Val Trp Asn Ala Phe Gly Gly Gly Thr Asn Val Glu Ile Lys Arg Ser
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 157
<211> LENGTH: 213
<212> TYPE: PRT
<213> ORGANISM: Artificial Sequence
<220> FEATURE:
<223> OTHER INFORMATION: 13B4 LC

<400> SEQUENCE: 157

Ser Tyr Glu Leu Thr Gln Pro Leu Ser Val Ser Val Ser Pro Gly Gln
1               5                   10                  15

Thr Ala Ser Ile Thr Cys Ser Gly Asp Lys Leu Gly Asn Val Tyr Ala
```

```
                20                  25                  30
Ser Trp Tyr Gln Gln Lys Pro Gly Gln Ser Pro Thr Leu Val Ile Tyr
            35                  40                  45
Gln Asp Asn Lys Arg Pro Ser Gly Ile Pro Glu Arg Phe Ser Gly Ser
        50                  55                  60
Asn Ser Gly Lys Thr Ala Thr Leu Thr Ile Ser Gly Thr Gln Ala Leu
65                  70                  75                  80
Asp Glu Ala Asp Tyr Tyr Cys Gln Ala Trp Asp Ser Ser Thr Ala Val
                85                  90                  95
Phe Gly Gly Gly Thr Lys Leu Thr Val Leu Arg Ser Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 158
<211> LENGTH: 219
<212> TYPE: PRT
<213> ORGANISM: Artificial Sequence
<220> FEATURE:
<223> OTHER INFORMATION: 13F7 LC

<400> SEQUENCE: 158

Asp Ile Val Met Thr Gln Thr Pro Leu Ser Leu Pro Val Ala Pro Gly
1               5                   10                  15
Glu Pro Ala Ser Ile Ser Cys Arg Ser Ser Gln Ser Leu Leu His Ser
            20                  25                  30
Asn Gly Tyr Asn Tyr Leu Asp Trp Tyr Val Gln Lys Pro Gly Gln Pro
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Arg Gln Thr Pro Leu Thr Phe Gly Gly Gly Thr Lys Val Glu Ile Lys
            100                 105                 110
Arg Ser Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
```

```
                    165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 159
<211> LENGTH: 214
<212> TYPE: PRT
<213> ORGANISM: Artificial Sequence
<220> FEATURE:
<223> OTHER INFORMATION: 15A9 LC

<400> SEQUENCE: 159

```
Asp Ile Gln Met Thr Gln Ser Pro Ser Ser Leu Ser Ala Ser Val Gly
1               5                   10                  15

Asp Arg Ile Thr Ile Ser Cys Arg Ala Ser Gln Ser Ile Ser Thr Ser
            20                  25                  30

Leu Asn Trp Tyr Gln Gln Thr Pro Gly Lys Ala Pro Arg Leu Leu Ile
        35                  40                  45

Tyr Gly Ala Ser Thr Leu Gln Ser Gly Val Pro Ser Arg Phe Ser Gly
    50                  55                  60

Gly Gly Ser Gly Thr Asp Phe Ser Leu Thr Ile Thr Ser Leu Gln Pro
65                  70                  75                  80

Glu Asp Phe Ala Thr Tyr Tyr Cys Gln Glu Ser Ala Ser Ile Pro Arg
                85                  90                  95

Thr Phe Gly Gln Gly Thr Lys Leu Asp Ile Lys Arg Ser Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 217
<212> TYPE: PRT
<213> ORGANISM: Artificial Sequence
<220> FEATURE:
<223> OTHER INFORMATION: P1-A03 LC

<400> SEQUENCE: 160

```
Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30
```

```
Ile Ser Trp Tyr Gln Gln Lys Pro Glu Lys Pro Thr Leu Leu Ile
        35                  40                  45

Ser Gly Ala Ser Asn Leu Glu Ser Gly Val Pro Pro Arg Phe Ser Gly
 50                  55                  60

Ser Gly Ser Gly Thr Asp Tyr Thr Leu Thr Ile Gly Gly Val Gln Ala
 65                  70                  75                  80

Glu Asp Ala Ala Thr Tyr Tyr Cys Leu Gly Gly Tyr Ser Tyr Ser Ser
                 85                  90                  95

Thr Gly Leu Thr Phe Gly Ala Gly Thr Asn Val Glu Ile Lys Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
        210                 215

<210> SEQ ID NO 161
<211> LENGTH: 217
<212> TYPE: PRT
<213> ORGANISM: Artificial Sequence
<220> FEATURE:
<223> OTHER INFORMATION: P1-A08 LC

<400> SEQUENCE: 161

Glu Leu Val Leu Thr Gln Ser Pro Ser Val Gln Val Asn Leu Gly Gln
1               5                   10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
 50                  55                  60

Ser Ser Gly Asn Thr Ala Thr Leu Thr Ile Ser Gly Ala Gln Ala Gly
 65                  70                  75                  80

Asp Glu Ala Asp Tyr Tyr Cys Ala Thr Ser Asp Gly Ser Gly Ser Asn
                 85                  90                  95

Tyr Gln Tyr Val Phe Gly Gly Gly Thr Gln Leu Thr Val Thr Arg Ser
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175
```

```
Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 162
<211> LENGTH: 215
<212> TYPE: PRT
<213> ORGANISM: Artificial Sequence
<220> FEATURE:
<223> OTHER INFORMATION: P1-F02 LC

<400> SEQUENCE: 162

Glu Leu Asp Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Thr Leu Leu Ile
        35                  40                  45

Tyr Gly Ala Ser Asn Leu Glu Ser Gly Val Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Tyr Cys Leu Gly Gly Tyr Ser Tyr Ser Ser
                85                  90                  95

Ile Thr Phe Gly Ala Gly Thr Asn Val Glu Ile Lys Arg Ser Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 163
<211> LENGTH: 219
<212> TYPE: PRT
<213> ORGANISM: Artificial Sequence
<220> FEATURE:
<223> OTHER INFORMATION: P2-A01 LC

<400> SEQUENCE: 163

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45
```

Tyr Gly Ala Ser Asn Leu Glu Ser Gly Val Pro Arg Phe Ser Gly
            50                  55                  60

Ser Gly Ser Gly Ser Asp Tyr Thr Leu Thr Ile Gly Gly Val Gln Ala
 65                  70                  75                  80

Glu Asp Ala Ala Thr Tyr Tyr Cys Leu Gly Gly Val Thr Tyr Ser Ser
                 85                  90                  95

Thr Gly Thr His Leu Thr Phe Gly Ala Gly Thr Asn Val Glu Ile Lys
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 164
<211> LENGTH: 219
<212> TYPE: PRT
<213> ORGANISM: Artificial Sequence
<220> FEATURE:
<223> OTHER INFORMATION: P2-A03 LC

<400> SEQUENCE: 164

Glu Leu Asp Leu Thr Gln Thr Pro Ala Ser Val Ser Glu Pro Val Gly
 1               5                  10                  15

Gly Thr Val Thr Ile Lys Cys Gln Ala Ser Gln Ser Ile Gly Gly Asn
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Asp Phe Thr Leu Thr Ile Ser Asp Leu Glu Cys
 65                  70                  75                  80

Ala Asp Ala Ala Thr Tyr Tyr Cys Gln Ser Pro Ala Tyr Asp Pro Ala
                 85                  90                  95

Ala Tyr Val Gly Asn Ala Phe Gly Gly Thr Glu Leu Glu Ile Leu
            100                 105                 110

Arg Ser Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 165
<211> LENGTH: 214
<212> TYPE: PRT
<213> ORGANISM: Artificial Sequence
<220> FEATURE:
<223> OTHER INFORMATION: P2-F07 LC

<400> SEQUENCE: 165

Glu Leu Asp Leu Thr Gln Thr Pro Ser Leu Ser Ala Ser Val Gly
1               5                   10                  15

Gly Thr Val Thr Ile Asn Cys Leu Ala Ser Glu Asp Ile Tyr Ser Ala
            20                  25                  30

Leu Ala Trp Tyr Gln Gln Lys Pro Gly Lys Pro Thr Leu Leu Ile
            35                  40                  45

Ser Gly Thr Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

Glu Asp Ala Ala Thr Tyr Phe Cys Gln Gly Tyr Ser Ser Tyr Pro Leu
                85                  90                  95

Thr Phe Gly Ala Gly Thr Asn Val Glu Ile Lys Arg Ser Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 166
<211> LENGTH: 220
<212> TYPE: PRT
<213> ORGANISM: Artificial Sequence
<220> FEATURE:
<223> OTHER INFORMATION: P2-F11 LC

<400> SEQUENCE: 166

Glu Leu Asp Leu Thr Gln Thr Pro Ser Val Ser Ala Ala Val Gly
1               5                   10                  15

Gly Thr Val Thr Ile Asn Cys Gln Ala Ser Gln Ser Val Tyr Asn Asn
            20                  25                  30

Lys Asn Leu Ala Trp Tyr Gln Gln Lys Pro Gly Gln Pro Pro Lys Leu
            35                  40                  45

Leu Ile Tyr Ala Ala Ser Thr Leu Ala Ser Gly Val Ser Ser Arg Phe
```

```
                        50                  55                  60
Lys Gly Ser Gly Ser Gly Thr Gln Phe Thr Leu Thr Ile Ser Asp Val
 65                      70                  75                  80

Gln Cys Asp Ala Ala Thr Tyr Tyr Cys Gln Gly Glu Phe Ser Cys
                 85                  90                  95

Ser Ser Ala Asp Cys Asn Ala Phe Gly Gly Thr Glu Leu Glu Ile
            100                 105                 110

Leu Arg Ser Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220
```